(12) United States Patent
Taylor et al.

(10) Patent No.: US 7,629,313 B2
(45) Date of Patent: Dec. 8, 2009

(54) IMMUNOMODULATORY POLYMERIC ANTIGENS FOR TREATING INFLAMMATORY PATHOLOGIES

(75) Inventors: Kathleen Ann Taylor, Fishers, IN (US); Larry Chris Blaszczak, Indianapolis, IN (US); Neil Thomas Blackburn, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/506,312

(22) PCT Filed: Mar. 7, 2003

(86) PCT No.: PCT/US03/05575

§ 371 (c)(1),
(2), (4) Date: Sep. 1, 2004

(87) PCT Pub. No.: WO03/075953

PCT Pub. Date: Sep. 18, 2003

(65) Prior Publication Data

US 2005/0119164 A1    Jun. 2, 2005

(51) Int. Cl.
*A61K 38/16*    (2006.01)
*A61K 31/739*    (2006.01)

(52) U.S. Cl. .......................... 514/8; 514/54; 424/278.1; 424/280.1

(58) Field of Classification Search .................. None
See application file for complete search history.

(56) References Cited

FOREIGN PATENT DOCUMENTS

WO    WO/0059515 A    10/2000

OTHER PUBLICATIONS

Freshney (Culture of Animal Cells, A Manual of Basic Technique, Alan R. Liss, Inc., 1983, New York).*
Dermer (Bio/Technology, 1994, vol. 12 p. 320).*
Tzianabos A. O., et al., *Journal of Biological Chemistry*, vol. 275, No. 10, Mar. 10, 2000, pp. 6733-6740; "T cells activated by zwitterionic molecules prevent abscesses induced by pathogenic bacteria".
International Search Report for WO 03/075953.
Rosenthal, Raoul and Roman Dziarski, "Isolation of Peptidoglycan and Soluble Peptidoglycan Fragments", Methods in Enzymology, Academic Press, Inc., 235:253-285 (1994).

* cited by examiner

*Primary Examiner*—Robert A Zeman
(74) *Attorney, Agent, or Firm*—David W. Maher; Tech Law LLP

(57) ABSTRACT

Provided are natural and synthetic immunomodulatory polymeric antigens (SPAs), compositions containing SPAs, and methods of using these natural and synthetic SPAs and compositions to prevent or treat inflammatory pathologies.

9 Claims, 8 Drawing Sheets

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: synthetic construct
<220> FEATURE:
<221> NAME/KEY: Peptide
<222> LOCATION: (2)..(2)
<223> OTHER INFORMATION: Xaa at position 2 is D-iso-Glu or D-iso-Gln
<220> FEATURE:
<221> NAME/KEY: Peptide
<222> LOCATION: (3)..(3)
<223> OTHER INFORMATION: Xaa at position 3 is Lys or Dpm
<220> FEATURE:
<221> NAME/KEY: Peptide
<222> LOCATION: (4)..(4)
<223> OTHER INFORMATION: Xaa at position 4 is D-Ala
<220> FEATURE:
<221> NAME/KEY: Peptide
<222> LOCATION: (5)..(5)
<223> OTHER INFORMATION: Xaa at position 5 is D-Ala

<400> SEQUENCE: 1

Ala Xaa Xaa Xaa Xaa
1               5
```

IMMUNOMODULATORY POLYMERIC ANTIGENS FOR TREATING INFLAMMATORY PATHOLOGIES

BACKGROUND OF THE INVENTION

1. Field of the Invention

The present invention relates to the field of immunology, and more particularly to immunomodulation. The present invention provides novel methods for preventing and treating inflammatory pathologies employing natural or synthetic polymeric antigens (N/S PAs) possessing immunomodulatory properties in these methods. The present invention also provides a process for preparing novel synthetic SPAs that can be used to induce the activity of T regulatory cells and the expression of interleukin 10 (IL10) in humans and other animals, affording protection against, and/or treatment for, a wide variety of inflammation-based pathologies.

2. Description of Related Art

Microbial antigens are the most powerful immunomodulators known. Among the most common examples are lipopolysaccharide (LPS) from Gram negative bacteria, and bacterial cell wall glycopeptides, also known as murein or peptidoglycan (PG), from both Gram negative and Gram positive bacteria. Bacterial PG is well established as a potent inflammatory agent (Wahl et al. (1986) *J. Exp. Med.* 165: 884). Many microbial antigens, including PG, are thought to exert their pro-inflammatory effects by activating one of the mammalian cell surface receptors known as Toll-like receptors (TLRs). The TLR then triggers an intracellular signaling pathway through transcription factor NF-κB, which in turn induces expression of genes coding for inflammatory mediators (chemokines and certain cytokines). PG itself is thought to activate through TLR2 (Hallman et al. (2001) *Pediatr. Res.* 50:315).

Recently, cDNA array technology has brought even higher resolution to our understanding of pro-inflammatory mediator induction by PG (Wang et al. (2000) *J. Biol. Chem.* 275: 20260). The most highly activated genes are those expressing chemokines (IL-8 and MIP-1β), and the second most highly activated genes are those expressing cytokines (TNF-α, IL1, and IL6). Regardless of mechanistic detail, the downstream effect of bacterial PG on the host is a potent inflammatory response. In fact, PG has long been used for induction of arthritis in animal models (Cromartie et al. (1977) *J. Exp. Med.* 146:1585). Partially purified PG from the bacterium *Streptococcus pyogenes* is now commercially available for such purpose (Lee Laboratories, Atlanta, Ga.). Fragments of PG, known collectively as muropeptides, also exhibit inflammatory effects in animals, and these effects are dependent on muropeptide structure (Tuomanen et al. (1993) *J. Clin. Invest.* 92:297). Even the very smallest fragments of PG, designated muramyl dipeptide (MDP), and glucosaminyl MDP (GMDP), as well as their derivatives, exhibit inflammatory effects in animals (Kohashi et al. (1980) *Infect. Immun.* 29:70).

Kasper and Tzianabos have demonstrated that certain polysaccharides purified from the surface of bacterial cells exhibit protective effects in vivo when tested in models of inflammation such as the formation of intraabdominal abscesses, intraabdominal sepsis, and post-surgical adhesions (U.S. Pat. Nos. 5,679,654 and 5,700,787; PCT International Publications WO 96/07427, WO 00/59515, and WO 02/45708). These investigators have demonstrated that when purified from whole capsule, certain polysaccharides derived from *Bacteroides fragilis, Staphylococcus aureus*, and *Streptococcus pneumoniae* have unique characteristics that set them apart from many polysaccharide antigens. The former molecules are high molecular weight, helical, and zwitterionic in nature (Wang et al. (2000) *Proc. Natl. Acad. Sci. USA* 97:13478-13481, and references 5-9 therein). Most bacterial polysaccharides are neutral or negatively charged, and are considered to be T cell-independent antigens (Abbas et al. (2000) *Cellular and Molecular Immunobiology*, W.B. Saunders, Philadelphia). Kasper and Tzianabos suggest that the zwitterionic nature of these polysaccharides plays a role in the interaction of these molecules with CD4+ T cells (Tzianabos et al. (1993) *Science* 262: 416-419; Tzianabos et al. (2001) *Proc. Natl. Acad. Sci. USA* 98:9365-9370). More recent work by this group suggests that some of these molecules may interact with antigen presenting cells (APCs) via their zwitterionic characteristics and further, that stimulation of CD4+ T cells by these polysaccharide antigens is dependent on MHC II-bearing APCs (Kalka-Moll et al. (2002) *J. Immunol.* 169:6149-6153). It has yet to be determined precisely how these interactions between zwitterionic polysaccharides and APCs may stimulate CD4+ T cells. These investigators have shown that zwitterionic polysaccharides activate CD4+ T cells in vitro as evidenced by the stimulation of proliferation and the production of the cytokines IL2, INFγ, and IL10, and that the protection is adoptively transferred by polysaccharide-stimulated T cells in vivo (PCT International Publication WO 00/59515; Kalka-Moll et al. (2000) *J. Immunol.* 164:719-724; Tzianabos et al. (2000) *J. Biol. Chem.* 275:6733-6738). In earlier studies by this group, stimulation of CD4+ cells did not necessarily depend on the presence of APCs, and the mitogenic properties of these molecules on T cells derived from rat and mouse species was different: rat splenocytes proliferated in response to CP1 treatment, while mouse splencocytes did not (Tzianabos et al. (1995) *J. Clin. Invest.* 96:2727-2731; Brubaker et al. (1999) *J. Immunol.* 162:2235-2242).

Overall, however, their observations led this group to hypothesize that the activation of CD4+ T cells by these polysaccharides leads to the production of cytokines such as IL2 or IL10 that protect against inflammatory responses (PCT International Publication WO 00/59515; Kalka-Moll et al. (2000) *J. Immunol.* 164:719-724; Tzianabos et al. (2000) *J. Biol. Chem.* 275:6733-6738; Tzianabos et al. (1999) *J. Immunol.* 163: 893-897). It remains unclear, however, exactly how these molecules activate T cells or how they exert their protective effects. Further complicating an understanding of these polysaccharides, this group has reported other studies indicating that the same zwitterionic polysaccharides can induce the formation of abscesses in the same in vivo model where protective effects of these molecules have been observed (Tzianabos et al. (1993) *Science* 262: 416-419; Tzianabos et al. (1994) *Infect. Immun.* 62:3590-3593). Therefore, from this body of literature, it is difficult to ascertain the mechanism whereby these zwitterionic polysaccharides act as modulators of the immune system.

Another group of investigators has described immunomodulatory effects of the exopolysaccharide (capsule-like) of *Paenibacillus jamilae*, a gram positive *bacillus* isolated from olive mill wastewaters (Ruiz-Bravo et al. (2001) *Clin. Diag. Lab. Immunol.* 8:706-710). Although the authors do not disclose the structural features of this polysaccharide, their results are similar to the work of Kasper and Tzianabos, summarized above. The molecule, referred to as CP-7, stimulates the proliferation of lymphocytes in culture, as well as significant expression of IFNγ and GMCSF. Further, this group reports that this compound renders mice resistant to *Listeria monocytogenes* infection. The investigators suggest that the mechanism may be through the stimulation of a Th1 response, which is in direct contrast to the invention disclosed herein.

In view of the confusing and sometimes contradictory effects reported in the literature for various immunomodulatory polysaccharides, there exists a need in the art for an understanding of the mechanism of action of protective, anti-inflammatory immunomodulatory molecules, including polysaccharides, as well as a need for additional therapeutic molecules that modulate the immune response in both a safe and effective manner. Such insight and additional molecules will facilitate the development of even more effective anti-inflammatory strategies and therapeutics.

SUMMARY OF THE INVENTION

Accordingly, in view of the need in the art for an understanding of the mechanism(s) by which immunomodulatory polysaccharide antigens induce protection against inflammation, as well as the need for additional molecules that can be used to modulate the immune response in humans and animals for anti-inflammatory therapeutic purposes, the present inventors have investigated the properties and effects of an immunomodulatory bacterial polysaccharide and a novel synthetic peptidoglycan on immune system function. They have discovered that the bacterial polysaccharide derived from the capsule of Streptococcus pneumoniae, referred to as CP1, as well as the novel synthetic peptidoglycan (PG) Compound 15 disclosed herein, which is a synthetic polymeric antigen, protect against the induction of inflammation in models of intraabdominal abscesses and post-surgical adhesions. They have also surprisingly discovered that when human peripheral blood mononuclear cells (PBMCs) are treated in vitro with an SPA as disclosed herein, the response is most notably the expression of IL10. Only minimal and early expression of IL2, IFN-γ, or TNF-α is observed. The stimulation of an anti-inflammatory response by the synthetic peptidoglycan polymer disclosed herein is completely novel and unexpected in view of the current body of evidence discussed above: while natural peptidoglycans are inflammatory, the presently disclosed synthetic peptidoglycan is anti-inflammatory. The inventors' surprising discovery of the in vitro anti-inflammatory activity of an SPA contrasts markedly with previously published observations on the activity of purified bacterial surface polysaccharides, and prompted them to test the activity of this SPA in an animal model of inflammation. The inventors observed that this SPA exhibits protective therapeutic effects in this animal model of inflammation-based pathology.

Accordingly, in one aspect, the present invention provides a synthetic polymeric antigen having the structure shown in Formula I:

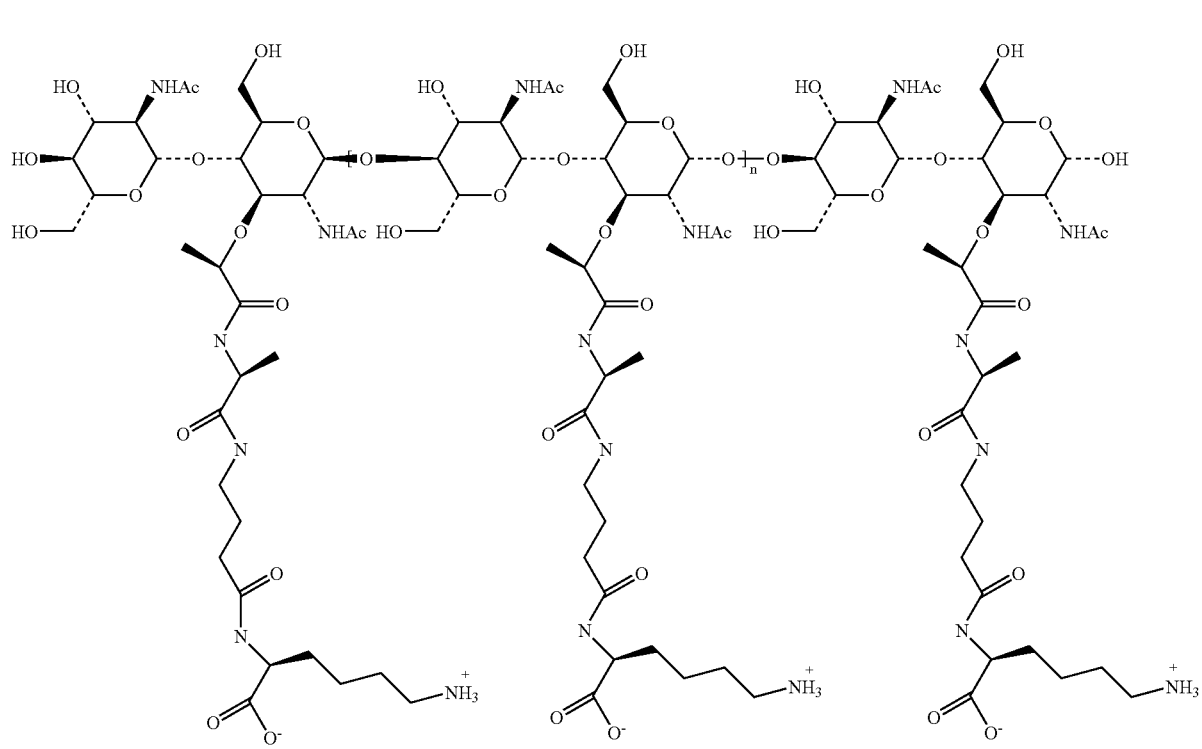

wherein n is an integral in the range of from about 375 to about 75, or a pharmaceutically acceptable salt thereof.

In another aspect, the present invention provides a composition, comprising the synthetic polymeric antigen or pharmaceutically acceptable salt thereof of Formula I, and a buffer, carrier, diluent, or excipient.

In another aspect, the present invention provides a pharmaceutical composition, comprising the synthetic polymeric antigen or pharmaceutically acceptable salt thereof of Formula I, and a pharmaceutically acceptable buffer, carrier, diluent, or excipient.

In another aspect, the present invention provides a method of inhibiting the maturation of an antigen presenting cell, comprising contacting in vitro said antigen presenting cell and an effective amount of a compound selected from the group consisting of CP1, Compound 15, and mixtures thereof, for a time and under conditions effective to inhibit maturation of said antigen presenting cell.

In another aspect, the present invention provides a method of inhibiting the maturation of an antigen presenting cell in a mammal, comprising administering to a mammal other than a rat or a mouse an effective amount of a compound selected from the group consisting of CP1, Compound 15, and mixtures thereof, and inhibiting maturation of said antigen presenting cell.

In another aspect, the present invention provides a method of inhibiting an inflammatory response in a mammal in need thereof other than a rat or a mouse, comprising:
(a) isolating peripheral blood mononuclear cells, or a monocyte-containing fraction thereof, from said mammal;
(b) contacting in vitro said isolated peripheral blood mononuclear cells or monocytes and a composition containing an effective amount of cytokines that differentiate monocytes to immature dendritic cells for a time and under conditions effective to generate immature monocyte-derived dendritic cells;
(c) contacting in vitro said immature monocyte-derived dendritic cells and an effective amount of a compound selected from the group consisting of CP1, Compound 15, and a mixture thereof for a time and under conditions effective to prevent maturation of said immature monocyte-derived dendritic cells; and
(d) administering said immature monocyte-derived dendritic cells to said mammal, reducing the ability of dendritic cells of said mammal to drive cognate interactions with T cells and inhibiting said inflammatory response in said mammal.

In this and the other ex vivo methods disclosed herein, administration of treated cells can be performed intravenously, intraperitoneally, or via intercardiac route.

Inflammatory responses that can be treated via the foregoing and following methods include abscesses and post-surgical adhesions, sepsis; rheumatoid arthritis; myesthenia gravis; inflammatory bowel disease; colitis; systemic lupus erythematosis; multiple sclerosis; coronary artery disease; diabetes; hepatic fibrosis; psoriasis; eczema; acute respiratory distress syndrome; acute inflammatory pancreatitis; endoscopic retrograde cholangiopancreatography-induced pancreatitis; burns; atherogenesis of coronary, cerebral, and peripheral arteries; appendicitis; cholecystitis; diverticulitis; visceral fibrotic disorders; wound healing; skin scarring disorders; granulomatous disorders; asthma; pyoderma gangrenosum; Sweet's syndrome; Behcet's disease; primary sclerosing cholangitis; and cell, tissue, or organ transplantation.

In yet another aspect, the present invention provides a method of inhibiting an inflammatory response in a mammal in need thereof other than a rat or a mouse, comprising:
administering to said mammal an effective amount of a compound selected from the group consisting of CP1, Compound 15, and mixtures thereof, preventing dendritic cells or other antigen presenting cells of said mammal from maturing and rendering them incapable of stimulating T cell activation,
thereby inhibiting said inflammatory response in said mammal.

In another aspect, the present invention provides a method of inhibiting an inflammatory response in a mammal in need thereof other than a rat or a mouse, comprising:

(a) isolating peripheral blood mononuclear cells, or a monocyte-containing fraction thereof, from said mammal;
(b) contacting in vitro said isolated peripheral blood mononuclear cells or monocytes and a composition containing an effective amount of cytokines that differentiate monocytes to immature dendritic cells for a time and under conditions effective to generate immature monocyte-derived dendritic cells;
(c) contacting in vitro said immature monocyte-derived dendritic cells and an effective amount of a compound selected from the group consisting of CP1, Compound 15, and mixtures thereof for a time and under conditions effective to prevent maturation of said immature monocyte-derived dendritic cells;
(d) contacting in vitro said immature dendritic cells and naïve T cells to generate T regulatory cells; and
(e) administering said T regulatory cells that suppress T effector cells to said mammal,
thereby suppressing said inflammatory response.

In a further aspect, the present invention provides a method of inhibiting an inflammatory response in a mammal in need thereof other than a rat or a mouse, comprising:
administering to said mammal an effective amount of a compound selected from the group consisting of CP1, Compound 15, and mixtures thereof,
generating T regulatory cells that suppress T effector cells and that inhibit said inflammatory response.

In another aspect, the present invention provides a method of measuring the immunological activity of CP1 or Compound 15 in a mammal, comprising:
administering CP1 or Compound 15 to said mammal;
administering Candin to said mammal; and
measuring the inhibition of delayed type hypersensitivity skin lesions elicited by said Candin,
wherein a reduction in lesion size in said mammal compared to lesion size in an untreated control mammal that has not received CP1 or Compound 15 indicates that said compounds are effective in inhibiting a localized inflammatory response.

Further scope of the applicability of the present invention will become apparent from the detailed description provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed description taken in conjunction with the accompanying drawings, all of which are given by way of illustration only, and are not limitative of the present invention, in which.

Figure 4:
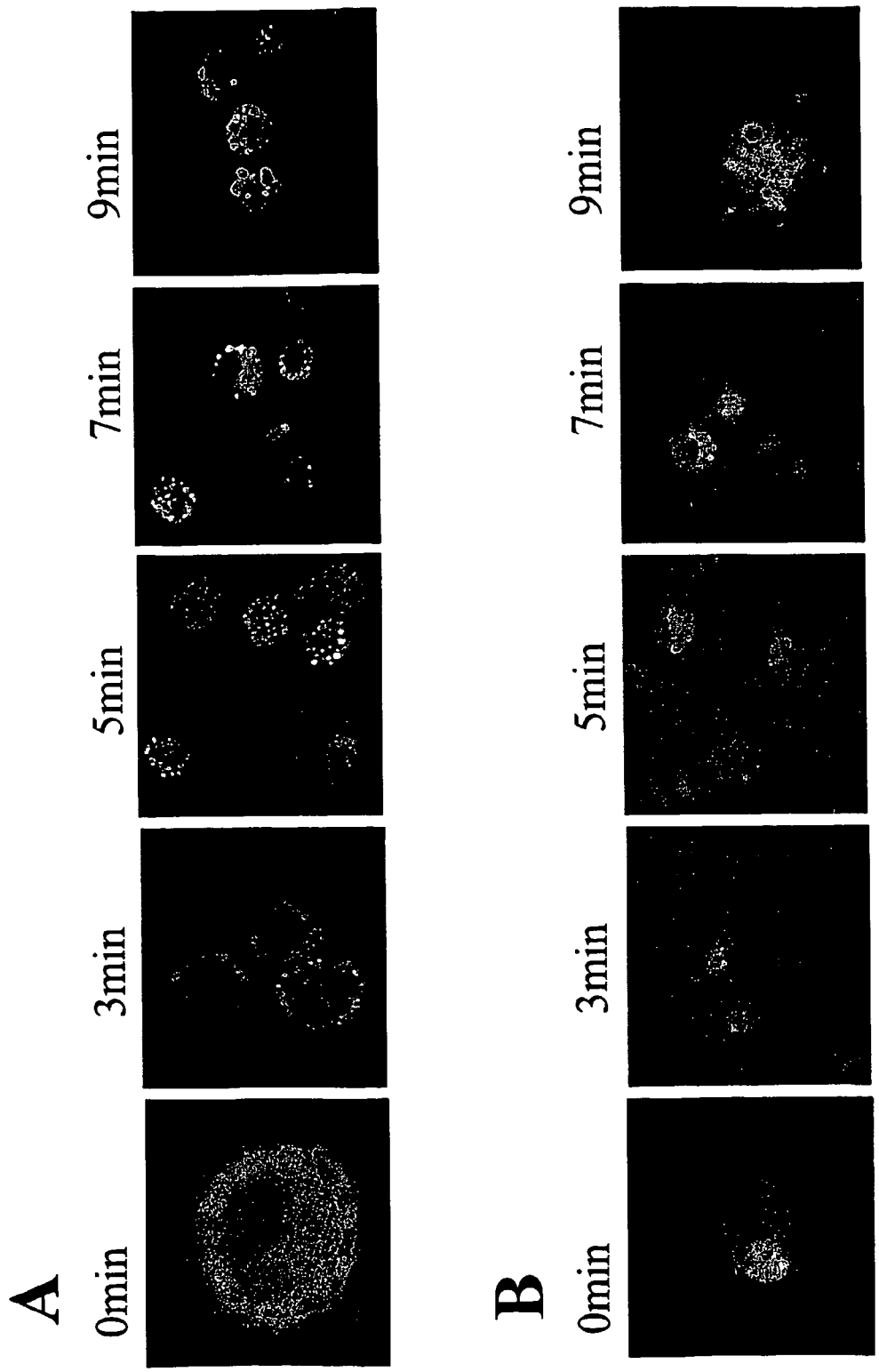

FIG. 4 shows Confocal microscope images of human iDCs treated with either FITC-Dextran (FITC-Dx, 40 kDa in size) or Oregon-green labeled Compound 15 (OG-PG, approx. 150 kDa in size) for two minutes. After incubation with the polymers, the cells are washed extensively to remove any external polymer and the internalized material followed at two-minute intervals. Localization of polymer in endocytic vacuoles can be seen using either compound, and fluorescence is visualized in the photographs as white punctate material within the dark field of the cells.

Figure 5:
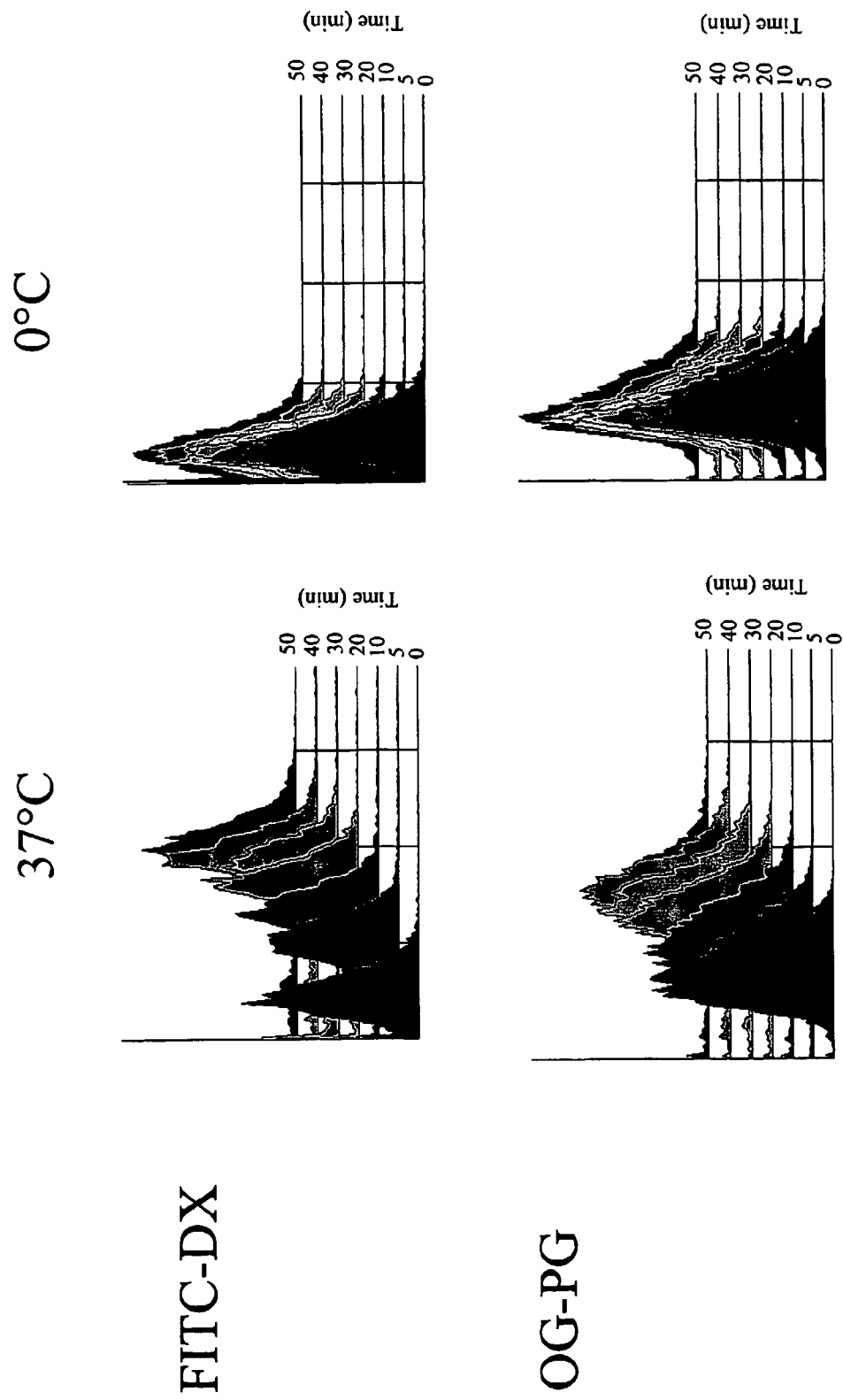

FIG. 5 shows flow cytometric analysis of uptake of either FITC-Dextran (panel A) or Oregon-green labeled Compound 15 (panel B) by human DC at 37° C. or 0° C., respectively. Each histogram shows the mean fluorescence intensity of fluorescent signal versus cell number at the time intervals indicated. The results show that the uptake of each molecule is similar, and that this uptake is inhibited when the cells are metabolically inactive at 0° C.

Figure 6:
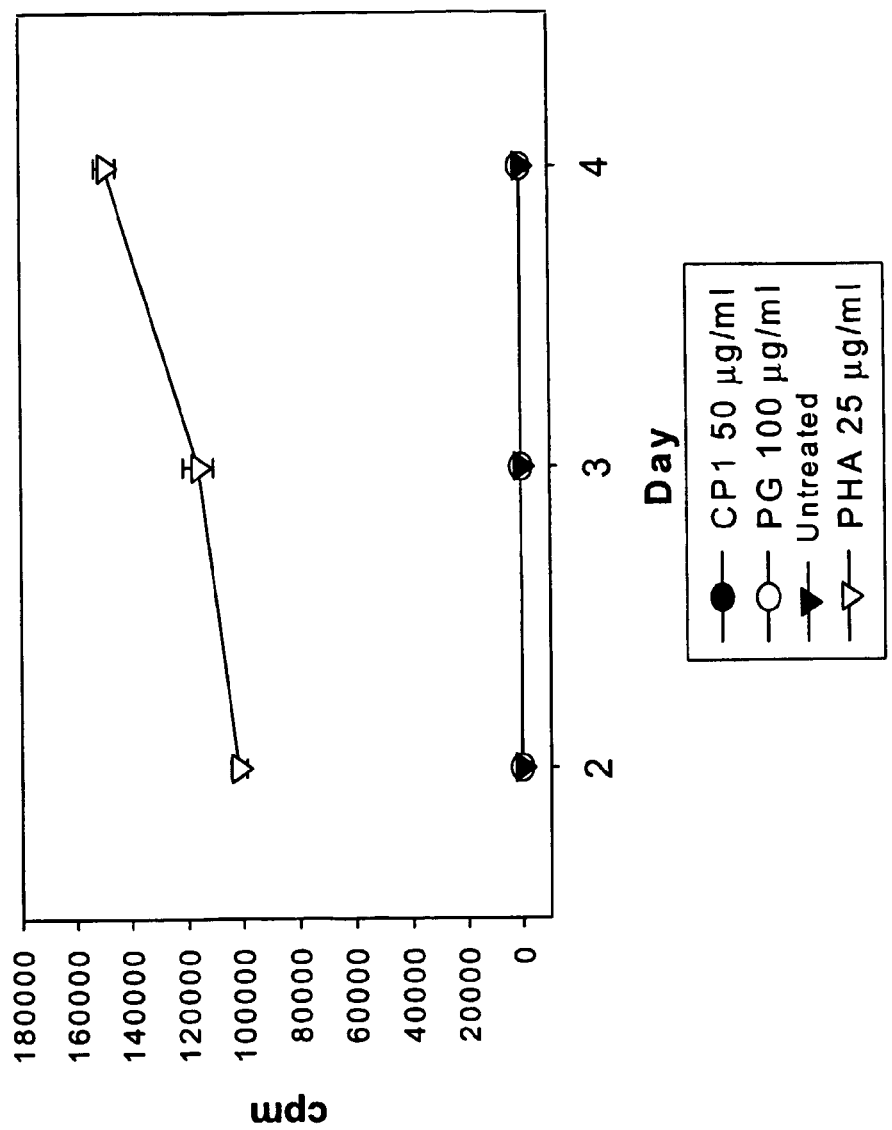

FIG. 6 shows that neither CP1 nor PG induces PBMCs to divide in culture. Isolated PBMCs are incubated with 50 μg/ml CP1 (●), 100 μg/ml pg (○), 25 μg/ml PHA (▽), or left untreated (▼) for the number of days indicated. Radioactive thymidine [$^3$H]-Thy is added to cultures 18 h prior to each time point and the amount of radiolabel incorporated by the cells is measured by scintillation counting. Radioactivity is measured as counts per minute.

Figure 7:
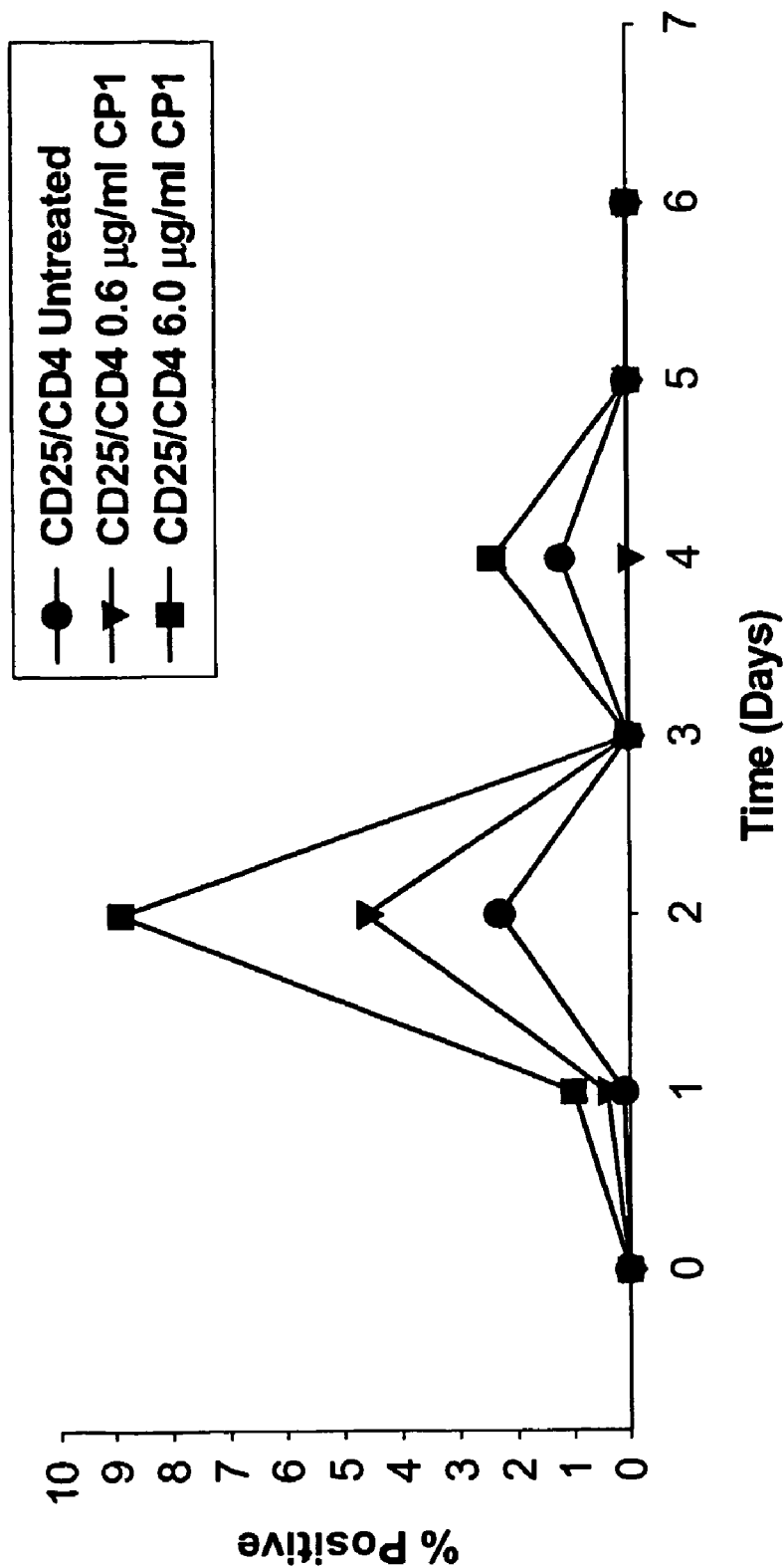

FIG. 7 shows that CP 1 induces an increase in the percent of CD4+CD25+ T regulatory cells in human PBMCs in a dose-dependent manner. Isolated PBMCs are incubated with CP1 at 0.6 micrograms/ml (closed triangle) or 6.0 micrograms/ml (closed square) for the number of days indicated. Untreated PBMCs (closed circle) are included as a measure of the base line number of CD4+CD25+ cells present in the culture.

Figure 8:
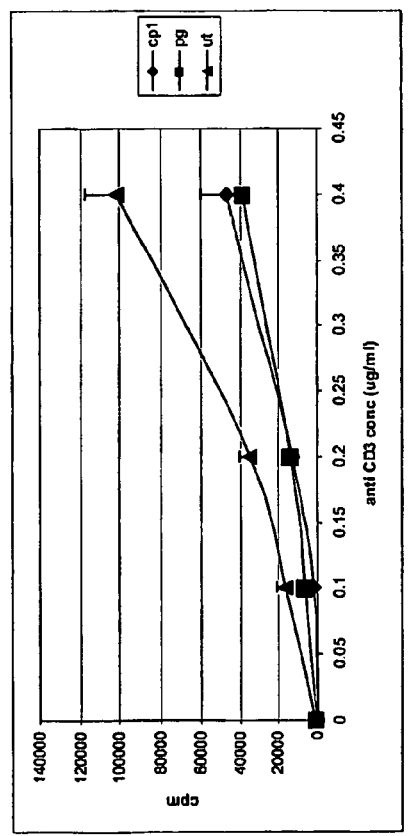
Figure 8:
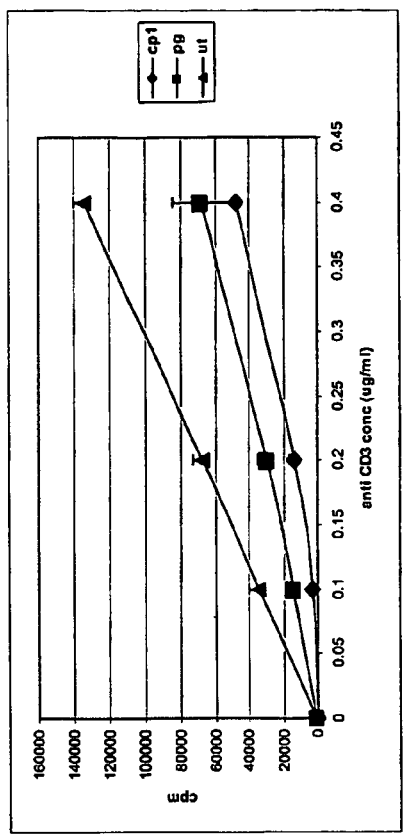

FIG. 8 shows that CP1 and synthetic PG Compound 15 inhibit anti-CD3 antibody-mediated proliferation of human PBMCs. PBMCs are pre-incubated for 24 hours with 50 mg/ml of CP 1 or 100 mg/ml of PG Compound 15 prior to incubation on tissue culture plates coated with varying concentrations of anti-CD3 antibody for 48 hours (panel A) or 72 hours (panel B). Cell proliferation is evaluated using a $^3$H-Thymidine incorporation assay followed by liquid scintillation counting.

DETAILED DESCRIPTION OF THE INVENTION

The following detailed description of the invention is provided to aid those skilled in the in practicing the present invention. Even so, the following detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

DEFINITIONS

As used herein, unless indicated otherwise, the following abbreviations shall be understood to have the following meanings:

| Abbreviation | Reagent or Fragment |
|---|---|
| h or hr | hour(s) |
| min. | minute(s) |

As used above, and throughout the description of the invention, the following terms, unless otherwise indicated, shall be understood to have the following meanings:

"Biomarker" means a marker of a specific activity that correlates with the administration of a drug. Non-limiting examples of biomarkers include a cell surface receptor, a soluble mediator, an mRNA message, or an in vivo response that is modulated and that can be measured.

"CP1" means a capsular polysaccharide obtainable from *Streptococcus pneumoniae* serotype 1. CP1 is used in the methods disclosed herein in a form isolated and purified as described below.

"Effective amount" refers to an amount of a compound or composition of the present invention effective to produce the desired or indicated immunologic or therapeutic effect.

"IL10" is an endogenous mediator that shifts equilibrium away from inflammation. Directed, endogenous generation of IL10 maximizes efficacy and minimizes toxic effects.

"Immune cell" means any cell capable of responding or mounting a response within the entirety of the host immune system. Generally these cells are referred to as "white blood cells" but are not necessarily limited to this category. Examples of immune cells include T and B cells, monocytes, macrophages, natural killer cells, dendritic cells, antigen presenting cells, and polymorphonuclear leukocytes.

"Modulate" means either an increase or a decrease in a selected parameter.

The terms "patient" or "subject" refer to mammals including humans and other primates, and companion, zoo, and farm animals, including, but not limited to, cats, dogs, rodents, horses, cows, sheep, pigs, goats, etc.

"Non-immune cell" means a cell that is not normally involved in immune responses but that may have the capacity to be modulated by products of the immune system.

"SPA" means "synthetic polymeric antigen." Compound 15 disclosed herein, which is a synthetic peptidoglycan (PG), is a particular SPA. SPAs can be produced by total synthesis.

"T regulatory cells" or "$T_{regs}$" refers to a unique lineage of immunoregulatory T cells that potently suppress inflammatory effector T cells in vitro and in vivo. $T_{regs}$ are characterized by expression of certain cell surface markers including, for example, CD4 and CD25 (CD4+/CD25+).

Natural and Synthetic Polymeric Antigens Useful as Immunomodulators

The structures of CP1, synthetic PG (Compound 15), and a generalized synthetic polymeric antigen (SPA) are shown below:

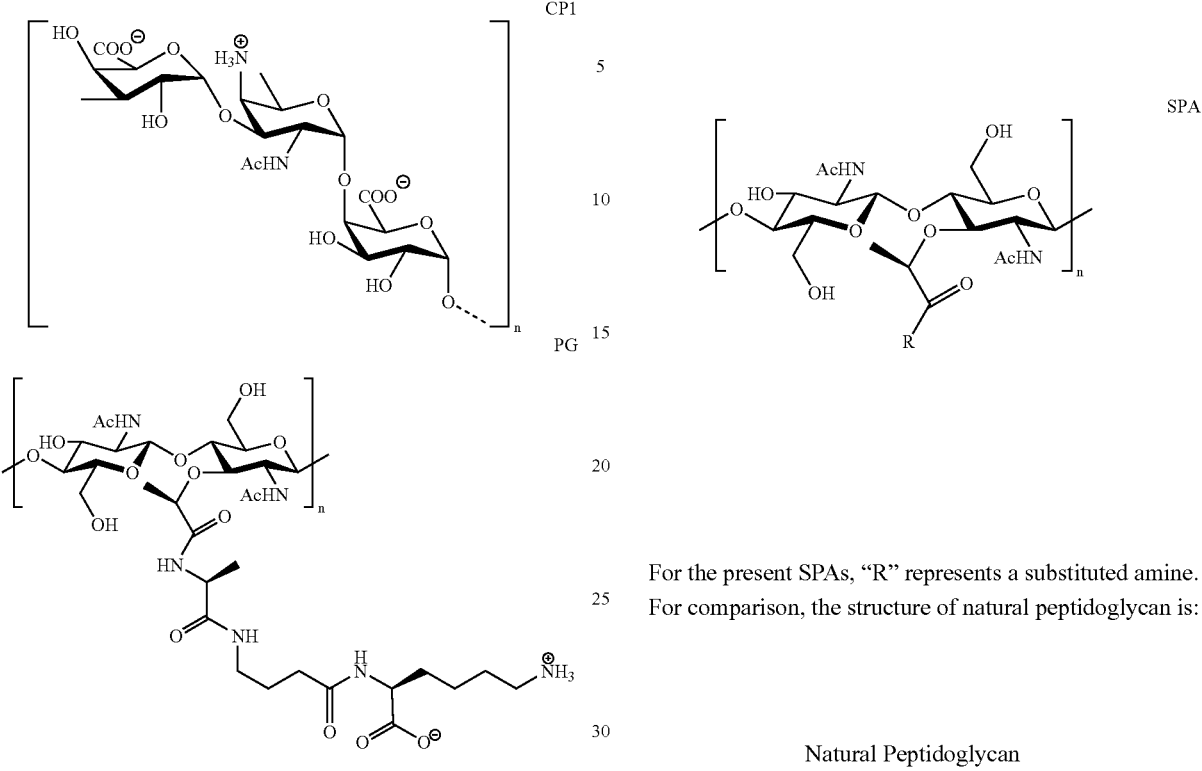
For the present SPAs, "R" represents a substituted amine.
For comparison, the structure of natural peptidoglycan is:
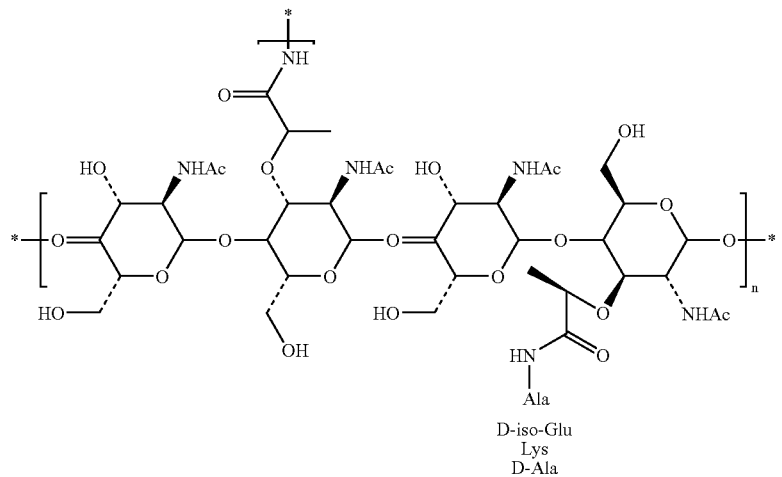
Natural Peptidoglycan

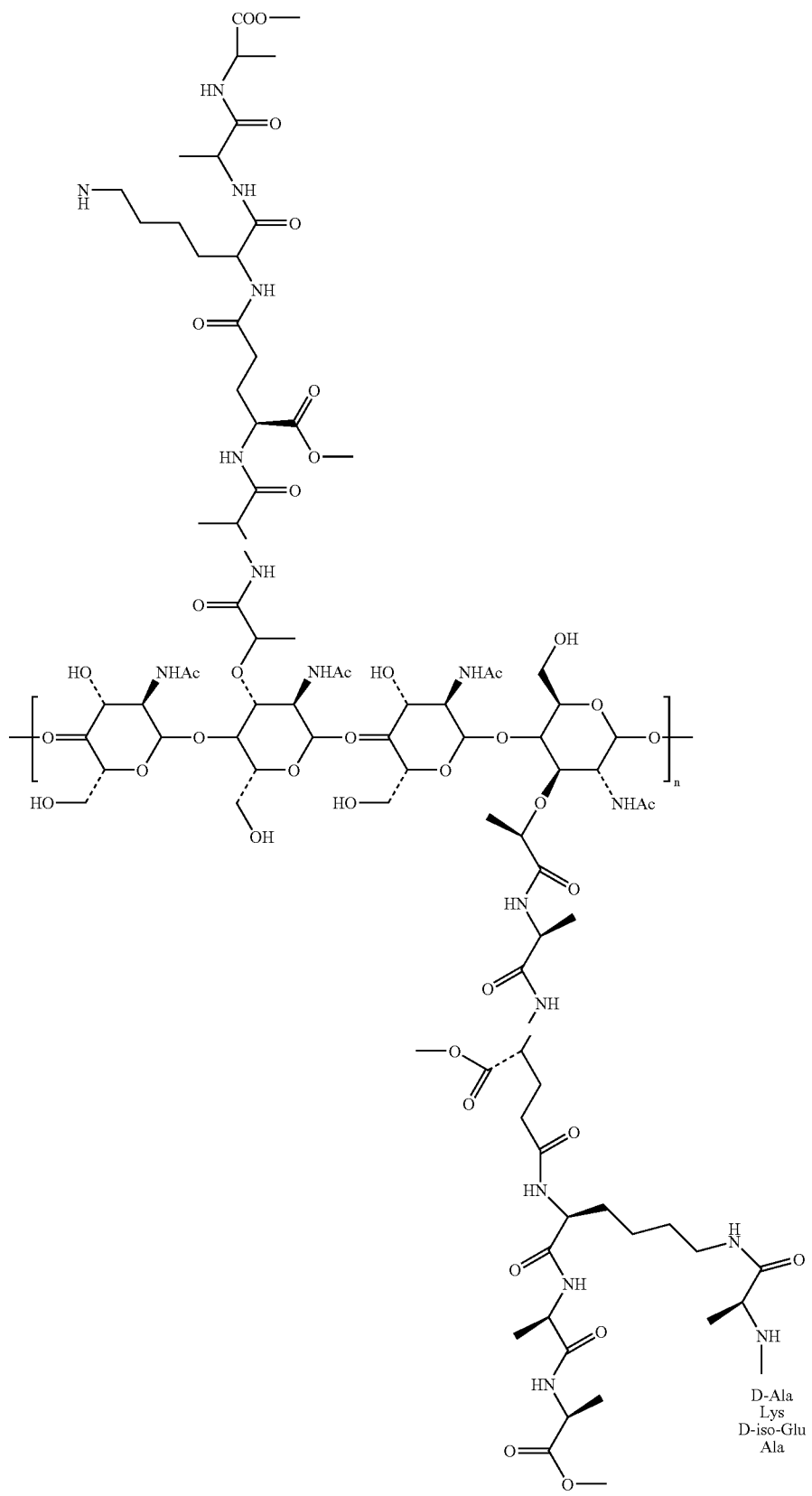

-continued

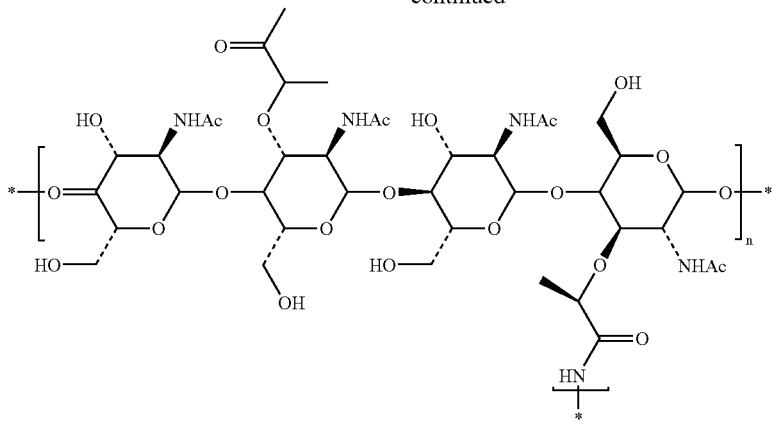

CP1 is a homopolymer of the indicated repeat unit (or one of its sequence isomers). It exists as a distribution of molecular weights centered around 270 kilodaltons as judged by size exclusion chromatography (dextran as standard). The material is isolated as a hygroscopic white powder that is soluble in water or saline.

SPAs are homopolymers of the indicated general repeat unit structure. These polymers resemble bacterial cell wall peptidoglycans, but are accessed through chemo-enzymatic total synthesis from N-acetylglucosamine.

Synthetic PG is an example of an SPA. It is a homopolymer of the indicated repeat unit, existing as a distribution of molecular weights centered around 150 kilodaltons. The polymer is a hygroscopic white powder that is soluble in water or saline.

Natural peptidoglycan in the bacterial cell wall is a single covalently closed macromolecule that precisely defines the shape of a bacterial cell throughout the cell cycle. It is composed of a rigid axis of parallel polymeric peptidoglycan glycan strands wherein the repeat unit is β-[1,4]-linked N-acetylglucosaminyl-β-[1,4]-N-acetylmuramylpentapeptide. The glycan strand is helical in shape with about four repeat units per complete turn of the helix. The more flexible pentapeptide axes extend N to C from the lactyl carboxyls of the muramic acid residues. The peptide is generally $H_2N$-Ala-D-iso-Glu(or iso-Gln)-Lys(or diaminopim-elate, DAP)-D-Ala-D-Ala-COOH (SEQ ID NO: 1). The peptides may be crosslinked between Lys(or DAP) from a donor strand to the carbonyl of the penultimate D-Ala of an acceptor strand. Although the diagram shows complete crosslinking for clarity, the actual degree of crosslinking in a living cell varies with genus and is always less than 100%.

In comparison, synthetic PG Compound 15 disclosed herein is linear, i.e., there is no crosslinking in the peptides. In addition, in amino acid position 2, GABA replaces the naturally occurring D-iso-Glu (D-iso-Gln) residues.

As described below in the method of preparation of CP1 (Example 2), the starting material for the preparation of CP1 as used herein is obtainable from the American Type Culture Collection (Manassas, Va.) as crude capsular material from *Streptococcus pneumoniae* (type 1), originally prepared for production of the Pneumovax vaccine (Merck Pharmaceuticals). As described above, CP1 as used in the present studies is highly purified, and consists solely of the CP1 polysaccharide, without the addition of any other stimulatory antigens or adjuvants. In contrast, Pneumovax vaccine contains more than 20 capsular type antigens, and is formulated with an adjuvant. The vaccine is designed to stimulate adaptive immunity and does so effectively. As such, the immune response to this vaccine is completely opposite from that observed when using the present isolated, purified CP1 (or Compound 15).

The present inventors have discovered that the bacterial polysaccharide derived from the capsule of *Streptococcus pneumoniae* (CP1), as well as the synthetic PG antigen Compound 15 disclosed herein, protect against the induction of inflammation in models of intraabdominal abscesses and post-surgical adhesions. As demonstrated in the examples presented below, investigations into the mechanism of protection induced by these molecules reveal that they appear to inhibit the maturation of dendritic cells, the most powerful antigen presenting cells (APCs) in the immune cell repertoire. Immature APCs are unable to activate T cells due to the their inability to signal T cells through co-stimulation. Treatment of human PBMCs with either molecule fails to stimulate activation or proliferation of T cells. This is completely unexpected in view of the literature on both zwitterionic polysaccharides and naturally occurring peptidoglycans, discussed earlier. Both of these classes of molecules have been reported to be mitogens for T cell activation (PCT International Publication WO 00/59515; Kalka-Moll et al. (2000) *J. Immunol.* 164:719-724; Tzianabos et al. (2000) *J. Biol. Chem.* 275: 6733-6738; Levinson et al. (1983) *Infect. Immun.* 39:290-296). Furthermore, CP1 and synthetic PG fail to stimulate Toll-like receptors in reporter cells in vitro, or to stimulate the expression of inflammatory cytokines in PBMC cultures, events that would be expected if maturation of APCs occurs through stimulation of TLR2 or other TLRs (Schwander et al. (1999) *J. Biol. Chem.* 274:17406-17409; Medzhitov et al. (2001) *Nat. Rev. Immunol.* 6: 135-145) with subsequent activation of T cells through the expected cognate interactions between the two cells types in the presence of antigen. The present inventors also observe an increase in the number of CD4+CD25+ cells present in PBMC cultures following treatment with CP1, suggesting that treatment with this molecule creates a population of immature APCs that drive the stimulation of T regulatory cells within the culture. This hypothesis is further supported by functional observations of suppression of proliferation of T cells in PBMC cultures stimulated with anti-CD3 antibodies following treatment with the natural or synthetic polymeric antigens. Finally, the inventors have also surprisingly discovered that when human PBMCs are treated in vitro with CP1 or synthetic PG Compound 15 as disclosed herein, the response is most notably the expression of IL10. Negligible expression of IL2, IFN-γ, TNF-α, IL6, or IL12 is observed. These results are in direct contrast to the body of literature on the recognition of bacterial polysaccharides by the immune system. Furthermore, the stimulation of an anti-inflammatory response by the synthetic peptidoglycan polymer disclosed herein is completely novel and unexpected in view of the current body of evidence regarding natural peptidoglycans, discussed above, indicating that bacterial peptidoglycan is a potent inflammatory agent. Thus, while natural peptidoglycans are inflammatory, the presently disclosed synthetic peptidoglycan Compound 15 is anti-inflammatory. The inventors' surprising discovery of the in vitro anti-inflammatory activity of this synthetic peptidoglycan contrasts markedly with previously published observations on the activity of purified bacterial peptidoglycans, and prompted them to test the activity of this SPA, as well as CP1, in animal models of inflammation. As demonstrated below, the inventors observe that both this synthetic peptidoglycan as well as CP1 exhibit protective therapeutic effects in this animal model of inflammation-based pathology.

Immunomodulatory Activities of Natural and Synthetic Polymeric Antigens (N/S PAs)

The N/S PAs of the present invention induce peripheral blood mononuclear cells (PBMCs) from animals and humans to secrete IL10. IL1 is a type 11 cytokine with pleomorphic effects (Moore et al. (2001) *Annu. Rev. Immunol.* 19:683-765). It has been shown to have potent anti-inflammatory activity, down-modulating inflammatory responses of T effector cells (Morel et al. (2002) *Immunol.* 106:229-236), dendritic cells (Martin et al. (2003) *Immunity* 18:155-167), and other antigen presenting cells (Williams et al. (2002) *J. Leuko. Biol.* 72:800-809). IL10 is produced by a variety of cell types, including T cells, dendritic cells, monocytes (Moore et al. (2001) *Annu. Rev. Immunol.* 19:683-765), and a specialized sub-set of T cells known as T regulatory (Treg) cells (Suri-Payor et al (2001) *J. Autoimmun.* 16:115-123). In many ways, this cytokine functions to help maintain a dynamic balance within the immune system. IL10 acts to tamp down unchecked inflammatory responses that could otherwise be deleterious to the host (Moore et al. (2001) *Annu. Rev. Immunol.* 19:683-765).

Interactions of Natural and Synthetic Polymeric Antigens with Dendritic Cells

Most microbial antigens signal the immune system through highly conserved structural motifs referred to as pathogen-associated microbial patterns (PAMPs) (Medzhitov (2001) *Nat. Rev. Immunol.* 135-145). PAMPs interact with Toll-like receptors (TLRs) present on a variety of antigen presenting cells to initiate a signaling cascade that results in the expression of pro-inflammatory cytokines such as IL12 and IL6, and a variety of chemokines (Janeway et al. (2002) *Annu. Rev. Immunol.* 20:197-216). Activation of antigen presenting cells through TLRs, in particular dendritic cells, leads to a maturation process that is characterized by increased expression of surface MHC II molecules and co-stimulatory molecules such as CD80 and CD86 (Chakraborty et al. (2000) *Clin. Immunol.* 94:88-98). This cascade is designed to marshal early defenders of the innate immune system to respond immediately to invasion, and forms the basis for the link to long-standing adaptive immunity through antigen presentation to T cells (Keller (2001) *Immunol. Lett.* 78:113-122). Since CP1 is derived from bacterial capsule and synthetic peptidoglycan Compound 15 is patterned after natural bacterial cell wall-derived peptidoglycan, one might expect that these polymers would possess PAMPs that could signal through TLRs. Indeed, natural peptidoglycan has been shown to be a ligand for TLR2 (Schwandner et al. (1999) *J. Biol. Chem.* 274:17406-17409). As surprisingly discovered by the present inventors, N/S PAs do not appear to activate TLR2 or any other TLR tested in either human or rodent cells. This is further evidenced by the lack of expression of IL12, IL6, or other pro-inflammatory cytokines in PBMC cultures stimulated with N/S PAs. In addition, human monocyte-derived dendritic cells are not driven to maturation by stimulation with N/S PAs. Following treatment with N/S PAs, immature dendritic cells do not demonstrate the characteristic upregulation in MHC II, CD80, or CD86 on their surface, despite the fact that these cells are considered to be the most potent of antigen presenting cells and avidly internalize these molecules and concentrate them in endocytic vacuoles.

Bacterial lipopolysaccharide (LPS) is a powerful TLR4 agonist (Beulter (2002) *Curr. Top Microbiol. Immunol.* 270:109-120.), and is commonly used as a maturation signal for immature dendritic cells (Ardavin et al. (2001) *Trends Immunol.* 22:691-700). LPS specifically upregulates co-stimulatory molecules such as CD80 and CD86 on dendritic cells (Michelsen et al. (2001) *J. Biol. Chem.* 276:25680-25686). These surface molecules are essential for signaling T cells to elaborate effector functions such as inflammatory responses. When immature dendritic cells are co-cultured with N/S PAs and LPS, CD80 and CD86 are not upregulated, suggesting that N/S PAs inhibit the maturation of dendritic cells.

Dendritic Cells

Figure 1:
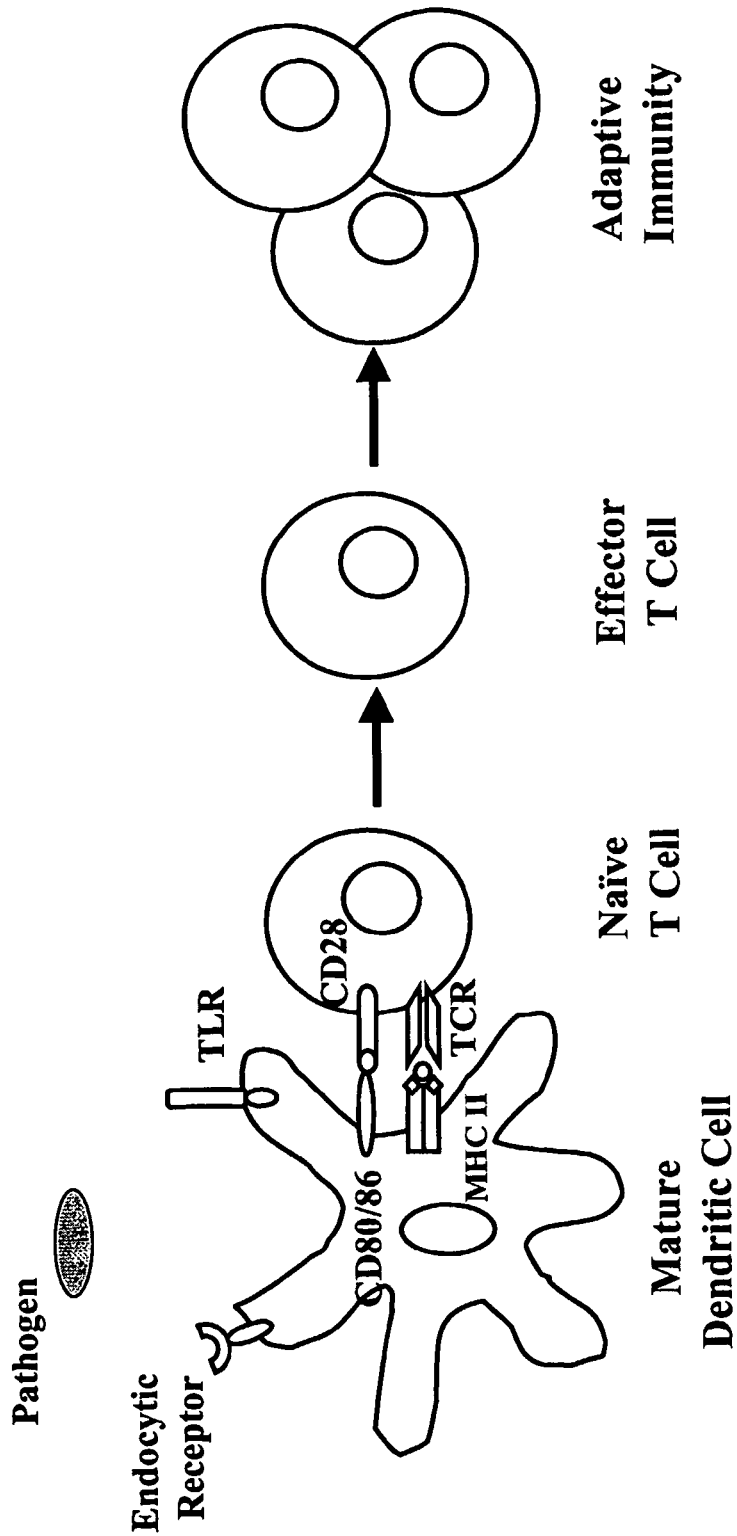
FIG. 1 is a schematic showing the normal events that occur when interactions between dendritic cells and T cells lead to inflammation or adaptive immunity

Dendritic cells (DCs) are a family of professional antigen presenting cells that are found in virtually every organ. Dendritic cell subtypes have been well defined, and it has been demonstrated that these cell types evolve through several levels of differentiation and maturation throughout their life span (Jonuleit et al. (2001) *Trends in Immunol.* 22:394-400). Immature dendritic cells are characterized by low expression of MHC II molecules, as well as limited expression of the co-stimulatory molecules CD80 and CD86. The expression of these surface molecules is dramatically upregulated in response to inflammatory stimuli such as IFNγ or ligation of TLR. Functionally, immature DCs in the periphery are especially adept at the capture and processing of antigens. Maturing DCs downregulate these activities, and significantly upregulate their ability to stimulate naïve T cells through the presentation of antigen via MHCII and co-stimulation through CD80/86 (Banchereau et al (2000) *Annu. Rev. Immunol.* 18:767-811). Summarized in FIG. 1.

In the absence of inflammation, most peripheral DCs are in an immature state, and it is thought that these cells play a major role in maintenance of peripheral T cell tolerance (recognition of self), induction of T cell anergy, and protection against autoimmunity (Jonuleit et al. (2001) *Trends in Immunol.* 22:394-400).

The present inventors have observed that treatment of immature dendritic cells with CP1 or synthetic polymeric antigen Compound 15 inhibits their ability to mature, despite the presence of a potent inflammatory stimulus (LPS). The consequences for immune regulation through immature or semi-mature (low CD80 and CD86 expression) dendritic cells are only beginning to be fully appreciated (Lutz et al. (2002) *Trends Immunol.* 23:445-449). It has been suggested that the induction of adaptive immunity versus tolerance or suppression of inflammation may be determined by the ratio of immature or semi-mature DCs to fully mature DCs in the periphery (Jonuleit et al. (2001) *Trends in Immunol.* 22:394-400; Garza et al. (2000) *J. Exp. Med.* 191:2021-2028). Chemotherapeutic maintenance of an immature DC population through treatment with N/S PAs may inhibit the cognate interactions between T cells and DCs, thus preventing the clonal expansion of antigen-specific effector T cells in response to inflammatory stimuli. In view of the entire body of evidence presented herein, however, it is more likely that the immature DCs generated by N/S PA treatment induce a T regulatory cell population that directly inhibits the activity of inflammatory effector T cells, thus affording protection against inflammatory pathologies. Evidence is mounting in the literature that immature DCs induce T regulatory cells in vivo, and further, T regulatory cells have been induced by immature DCs that specifically protect animals from influenza virus infection and prevent rejection in models of transplantation (Jonuleit et al. (2001) *Trends in Immunol.* 22:394-400; Dhodapkar et al. (2001) *J. Exp. Med.* 193:233-238; Thomson et al. (1999) *Transplant. Proc.* 31:2738-2739). In these studies, immature DCs were expanded ex vivo and then administered to animals. N/S PAs could provide a unique therapy in which autologous or immunologically compatible DCs are rendered chronically immature through ex vivo treatment and then reintroduced into patients to stimulate T regulatory activity.

T Regulatory Cells

Recent studies from several laboratories have demonstrated that the immature dendritic cell is a critical component in the generation of T regulatory cells (Tregs) (Jonuleit et al. (2001) *Trend Immunol.* 22:394-400). T regulatory cells function to maintain peripheral tolerance, protect against autoimmunity, and participate in modulating inflammation to allow for appropriate responses to microbial invasion or tissue damage while protecting the host from deleterious bystander effects (Maloy et al. (2001) *Nat. Immunol.* 2:816-822).

The most intensely studied Treg phenotype is characterized by the constitutive expression of the surface markers CD4 and CD25 (Shevach (2002) *Nat. Rev. Immunol.* 2:389-400). T regulatory cells with this phenotype have been identified both in vitro and in vivo in both rodents (Taylor et al. (2001) *J. Exp. Med.* 193:1311-1317) and man (Jonuleit et al. (2001) *J. Exp. Med.* 193:1285-1294). CD4+CD25+ T cells naturally occur in the peripheral circulation at a frequency of approximately 2-10% (Shevach (2002) *Nat. Rev. Immunol.* 2:389-400). During co-culture of CD4+CD25− target cells with CD4+CD25+ T regulatory cells, the T regulatory cells inhibit the proliferation of CD4+CD25− target cells despite the presence of potent proliferative signals such as antiCD3 antibodies or allogeneic APCs (Pasare et al. (2003) *Science* 299:1033-1036). To date, there have been no reports describing a definitive chemical means to generate T regulatory cells in vivo. Early studies reported in the literature indicated that CD4+CD25+ Treg cells expressed some IL10 in vitro (Shevach (2002) *Nat. Rev. Immunol.* 2:389-400). Furthermore, in inflammatory models, CD4+ CD25+ cells were unable to inhibit inflammation in IL10 knockout animals (Shevach (2002) *Nat. Rev. Immunol.* 2:389-400). These studies led to the widely held belief that the mechanism of T regulatory anti-inflammatory activity is via the expression of IL10. Elegant studies performed in several laboratories (Jonuleit et al. (2001) *J. Exp. Med.* 193:1285-1294; Levings et al. (2001) *J. Exp. Med.* 193:1295-1302; Dieckman et al. (2001) *J. Exp. Med.* 193:1303-1310) have shown that while CD4+CD25+ T cells do indeed express IL10 and/or other cytokines, the mechanism by which they suppress inflammatory T cells is dependent on cell-cell contact. In the initial interactions between CD4+CD25+ T cells and their targets, cytokine expression does not play a role. Recently, this seemingly paradoxical set of observations was clarified by the work of Diekman et al. ((2002) *J. Exp. Med.* 196:247-253). This group has also shown that CD4+CD25+ T cells interact with inflammatory T cells through cell-cell contact. Although the exact nature of the signals transduced by this contact is not yet known, these workers demonstrated that one important consequence of contact is that the target cells, i.e., CD4+CD25− T cells, become anergized, and begin to express high levels of IL10. Since T regulatory cells are relatively rare in the context of the entirety of the immune system, this provides a mechanism to amplify the anti-inflammatory effect, and explains the body of data indicating a role for IL10 in systemic anti-inflammation mediated by CD4+CD25+ T cells.

Human PBMC cultures treated with N/S PAs do not respond by proliferation when compared to control cultures treated with polyclonal mitogens such as phytohaemagglutinin (PHA) or superantigens such as *Staphylococcus aureus* enterotoxin A (SEA). N/S PAs do, however, stimulate an increase in the percentage of CD4+CD25+ cells present in the culture. Furthermore, when N/S PA-treated PBMC cultures are stimulated with αCD3 antibodies, there is a marked suppression in the proliferative capacity of the culture compared to that of untreated controls. Microarray analysis further reveals that PBMC cultures treated with N/S PAs and αCD3 antibodies selectively upregulate the expression of IL10 and IL19 (an IL10 paralogue) messages in the CD3+ T cell population while downregulating several inflammatory cytokine messages such as IL17 and TNFβ.

Taken together, the data disclosed herein suggest that N/S PAs inhibit the maturation of dendritic cells. Immature dendritic cells have a unique capacity to drive the generation of T regulatory cells. Treg cells may then participate in the inhibition of inflammatory responses through cell-cell signaling as well as through the stimulation of IL10 expression from anergized T cells at the sites of inflammation.

IL10

The concept of using recombinant IL10 as an immunotherapeutic is widely accepted (Madsen (2002) *Gastroenterol.* 123:2140-2144; Barnes (2001) *Curr. Opin. Allergy Clin. Immunol.* 1:555-560; Bremeanu et al (2001) *Int. Rev. Immunol.* 20:301-331; St. Clair (2000) *Curr. Dir. Autoimmun.* 2:126-149). There are numerous animal models of inflammation in which IL10 has been shown to be efficacious, e.g., inflammatory bowel disease (IBD), Crohn's disease, rheumatoid arthritis, autoimmune diabetes, and allergic disease (Madsen (2002) *Gastroenterol.* 123:2140-2144; Barnes (2001) *Curr. Opin. Allergy Clin. Immunol.* 1:555-560; Bremeanu et al (2001) *Int. Rev. Immunol.* 20:301-331; St. Clair (2000) *Curr. Dir. Autoimmun.* 2:126-149). Clinical trials using recombinant IL10 for the treatment of inflammatory bowel disease have, however, met with mixed results. Requirements for repeated high dose regimens, as well as some resulting toxicity, have hampered the success of these efforts. Harnessing an individual's immune system to selectively produce endogenous IL10 via T regulatory activity may provide a better route to immunotherapy. Expression of endogenous IL10, modulated by the host within the entirety of the immune system, may provide the appropriate context to achieve efficacy without the requirement for repeated dosing or the problems of cytokine toxicity. Furthermore, the selective enhancement of a cell population may prove to be the ideal delivery system for such a potent cytokine. Inherent in the immune cell repertoire is the ability to traffic within the body to sites of inflammation. An immune cell population that has been given a specific trafficking signal via a N/S PA-tolerized dendritic cell may populate specific sites and locally induce IL10 expression. This therapeutic approach would avoid the problems associated with systemic administration of potent cytokines and better mimic the naturally localized action of this immune mediator.

Intra-Abdominal Abscesses

The formation of intra-abdominal abscesses is the consequence of contamination of the peritoneal cavity with colonic bacteria. This usually occurs during trauma or surgical interventions. Bacteria stimulate a vigorous inflammatory response, resulting in the recruitment of macrophages, polymorphonuclear leukocytes (PMNs), and lymphocytes, and the release of a variety of inflammatory mediators such as IL1β, TNFα TNFβ, IL17, as well as a number of chemokines (Whal. et al. (1986) *J. Exp. Med.* 163:884-891; Tzianabos et al. (2002) *Curr. Opin. Micro.* 5:92-95). One possible outcome of this response is the encapsulation of invading bacteria by a variety of immune cells interlaced with deposits of fibrin. Once formed, the abscess is relatively resistant to antibiotic therapy, and patients often require surgical intervention to drain the abscess. Although prophylactic antibiotics are given to patients at risk, these interventions are not fully successful. A method to prevent the initial formation of an abscess by modulation of the host response through T regulatory cell activity and the expression of IL10 represents a better form of therapy that could become a standard of care for at risk surgical procedures.

Post-Surgical Adhesions

Post-surgical adhesions are a significant complication of abdominal, gynecologic, orthopedic, and cardiothoracic surgeries. In the abdomen and pelvic cavity, adhesions are associated with considerable morbidity and can be fatal. In preclinical models, exogenously administered IL10 has been shown to limit the formation of adhesions (Laan. et al. (1999). *J. Immunol.* 162:2347-2352; Chung et al. (2002). *J. Exp. Med.* 195:1471-1476). Current therapies in human medicine are, however, designed to interrupt the formation of adhesions after surgical insult. These products involve the introduction of gels or barrier products into the surgical site. These devices have met with only limited success due to enhanced infection rates, lack of efficacy, and relatively low rates of use within the medical community. Better methods to prevent the formation of adhesions are urgently needed.

Like abscess formation, current evidence suggests that the formation of adhesions also involves activation of inflammatory processes, most notably the consistent expression of the inflammatory mediator, IL17, and the deposition of fibrin and other matrix proteins. Together, these processes define a unique intersection between the immune system and pathways of fibrinogenesis and wound repair. Due to the unique nature of N/S PAs and the potential to manipulate the structures of synthetic PAs and thus their modulating activity, N/S PAs could prove to be useful tools to explore these interactions in greater detail. Specifically, N/S PAs may be useful in the identification and development of biomarkers that are indicative of specific immune or fibrinogenic responses.

Delayed Type Hypersensitivity Assay for Use as a Clinical Study Biomarker

In view of the observations that N/S PAs elicit their protective effects through the response of a T regulatory population to inflammatory stimuli, there is a need to develop a specific assay to measure this activity for clinical studies. Early phase clinical trials typically employ healthy volunteers for safety and dose response assessment, a scenario that does not necessarily include the induction or measurement of a specific inflammatory pathology. It is therefore necessary to develop a surrogate biomarker for the activity of these compounds. Delayed Type Hypersensitivity (DTH) reactions in the skin have been used for decades to assess exposure to *Mycobacterium tuberculosis* (TB) in humans, and more recently to determine the state of T cell responsiveness in the face of immunocompromise (Anderson et al. (1968) *Immunology* 15:405-409; Gray et al (1994) *Curr. Opin. Immunol.* 6:425-437; Kuby et al. (2000) Immunology, W. H. Freeman and Co.) Studies in the literature have demonstrated that the DTH response is primarily mediated by T cells and that the inflammatory activity can be adoptively transferred to naïve animals by DTH T cells alone (Elices et al. (1993) *Clin. Exp. Rheumatol.* 11:s77-s80). As disclosed herein, a Guinea pig model of DTH has been developed to assess the ability of N/S PAs to limit the localized inflammatory reaction in the skin. Direct measurements of the DTH response can be readily observed and measured in humans and Guinea pigs. Flares, wheals, and/or indurations can be observed and readily measured quantitatively on the surface of the skin. The antigen used to elicit inflammatory T cell activity in this assay, derived from *Candida albicans* (Candin), is currently being used clinically to measure immune competence in individuals undergoing transplant therapies or suffering from AIDs. This antigen is also considered to be safer for the general population than TB antigens. When tested in this model, CP1 demonstrates significant efficacy in preventing the characteristic skin lesions of DTH. Since it has been reported in the literature that CD4+CD25+ T regulatory cells are essential components of the memory and protective immunity to *C. albicans* (Montagnoli et al. (2002) *J. Immunol.* 169:6298-6308), these results provide further evidence that the protective effects of N/S PAs are derived from T regulatory activity.

Mechanism of Action of Naturally Occurring and Synthetic Polymeric Antigens: The T Regulatory Cell Hypothesis The present inventors have conducted detailed investigations into the mechanism(s) by which immunomodulatory molecules such as CP1 and the synthetic polymeric antigen Compound 15 direct and elicit anti-inflammatory effects in mammals, including the induction of T regulatory cell populations. From these studies, the following picture, summarized in FIG. 2, has emerged.

Figure 2:
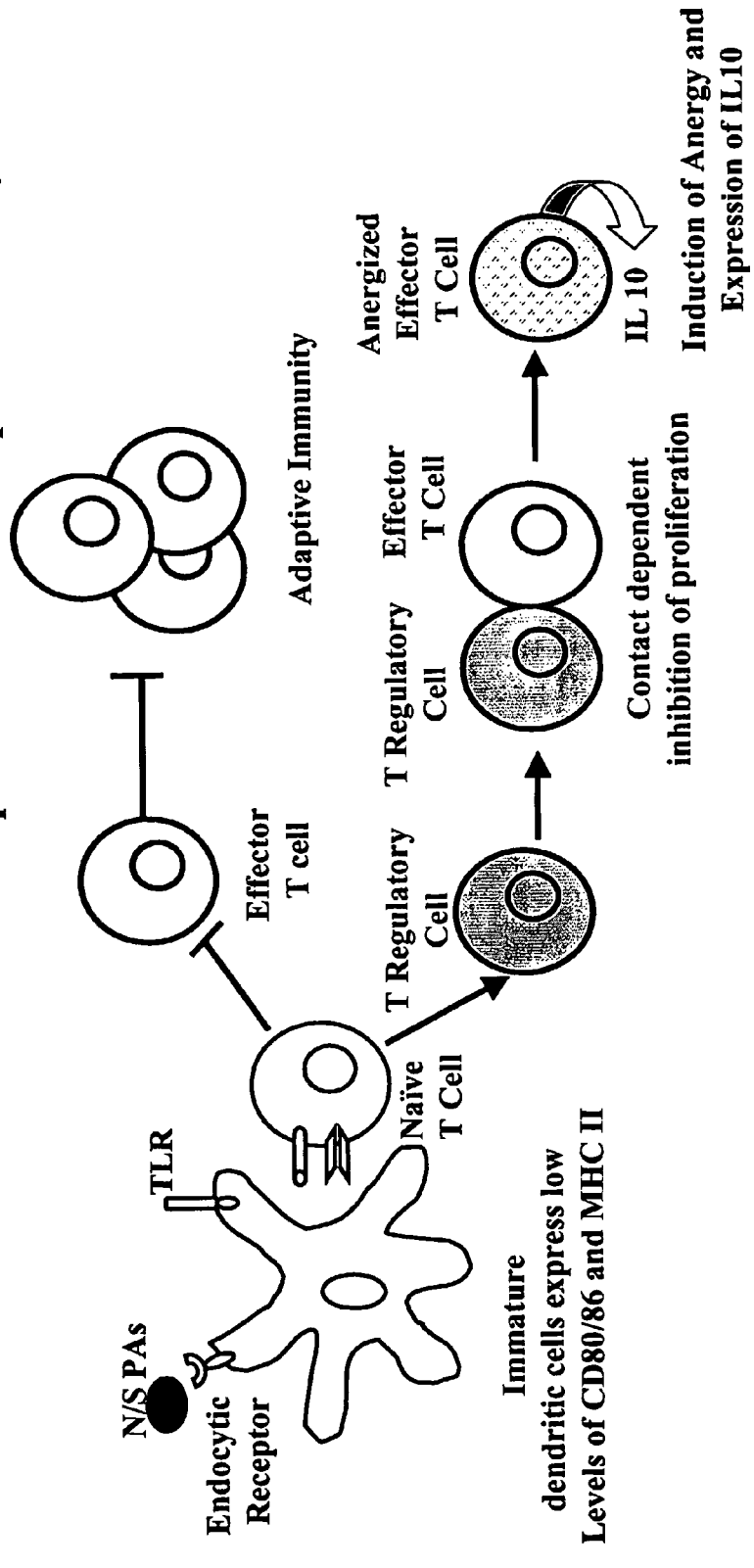
FIG. 2 is a schematic showing the T regulatory cell hypothesis of the present invention.

As depicted in FIG. 2, natural or synthetic immunomodulatory polymeric antigens inhibit the maturation of dendritic cells. Immature dendritic cells (iDCs) express low CD80 and CD86 co-stimulatory molecules. In this state, iDCs have the unique ability to interact with naïve T cells and induce the generation of CD4+CD25+ T regulatory cells (pathway B). In the face of an inflammatory response, T regulatory cells interact with T effector cells through cell-cell dependent contact and inhibit the proliferative capacity of these T inflammatory effector cells. Further, contact between T regulatory cells and T effector cells renders the effectors anergic and stimulates these cells to express large amounts of IL10. Elicitation of IL10 expression in the former inflammatory T cell effectors serves to amplify the suppressive effects of direct T regulatory cell contact and broadens the protection against an ongoing inflammatory process. The inhibition of maturation of dendritic cells observed by the present investigators could also inhibit the clonal expansion of T effector cells through the lack of cognate interactions between these two cell types (pathway A). However, the data presented herein more compellingly support the hypothesis that T regulatory cells are ultimately generated by the natural or synthetic polymeric antigens of the present invention and afford protection against inflammatory pathologies.

Pharmaceutical Compositions

The natural and synthetic immunomodulatory polymeric antigens disclosed herein can be used to prevent or treat inflammatory pathologies in humans and other mammals. Thus, in one aspect, the present invention provides pharmaceutical compositions for human and veterinary medical use comprising CP1 and the synthetic PG of the present invention, together with one or more pharmaceutically or physiologically acceptable carriers, excipients, or diluents, and optionally, other therapeutic agents. Thus, the present invention also relates to pharmaceutical compositions of the presently described immunomodulating polymers in combination with a antibacterial agent or other therapeutic agent, and a pharmaceutically acceptable carrier, excipient, or diluent.

The immunomodulatory polymers of the present invention can be delivered separately with another anti-bacterial antibiotic drug(s), or in the form of anti-bacterial antibiotic cocktails. An anti-bacterial antibiotic cocktail is a mixture of a molecule of the present invention and an anti-bacterial antibiotic drug and/or supplementary potentiating agent. The use of antibiotics in the treatment of bacterial infection is routine in the art. In this embodiment, a common administration vehicle (e.g., tablet, implant, injectable solution, etc.) can contain both a natural or synthetic polymeric antigen and the anti-bacterial antibiotic drug and/or supplementary potentiating agent. Alternatively, the anti-bacterial antibiotic drug can be separately dosed.

Non-limiting examples of anti-bacterial antibiotic drugs useful in the present invention include: penicillin G, penicillin V, ampicillin, arnoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefinenoxine, ceftriaxone, moxalactam, cefotetan, cefoperazone, ceftazidme, imipenem, clavulanate, timentin, sulbactam, neomycin, oritavancin, erythromycin, metronidazole, chloramphenicol, clindamycin, lincomycin, vancomycin, trimethoprim-sulfamethoxazole, aminoglycosides, quinolones, tetracyclines, and rifampin. Note *Goodman & Gilman's The Pharmacological Basis of Therapeutics*, Ninth Edition, Hardman et al., Eds., McGraw-Hill, New York, (1996) in this regard. The precise amounts of the therapeutic agent used in combination with the immunomodulatory polymers of the present invention will depend upon a variety of factors, including the polymer itself, the dose and dose timing selected, the mode of administration, the nature of any surgery that may be contemplated, and certain characteristics of the subject. Where local administration is carried out, it will be understood that very small amounts may be required (nanograms, or possibly picograms). The precise amounts selected can be determined without undue experimentation, particularly since a threshold amount will be any amount that will favorably enhances the desired immune response. A dose in the range of from about one picogram to about one milligram may be efficacious, depending upon the mode of delivery; a dose in the range of from about one nanogram to about one microgram may also be useful.

Dosing Treatment Regimen, and Administration

The compounds of the present invention can be administered in an effective amount for inducing protection against a wide variety of different inflammation-based pathologies, including post-surgical adhesions and intra-abdominal abscesses associated with bacterial infection. For such purposes, an effective amount is that amount of a compound of the present invention that will, alone or together with further doses or additional therapeutic compounds, inhibit, ameliorate, or prevent the inflammation-based pathology. The dose range can be from about one picogram/kilogram bodyweight to about one milligram/kilogram bodyweight, or from about one nanogram/kilogram bodyweight to about one microgram/kilogram bodyweight. The absolute amount will depend upon a variety of factors, including the nature of the inflammatory pathology to be treated, whether the administration is in conjunction with elective surgery or emergency surgery, concurrent treatment, the number of doses, individual patient parameters including age, physical condition, size and weight, and the severity of the inflammation-based pathology, and can be determined by the medical practitioner with no more than routine experimentation. It is generally preferred that a maximum dose be used, that is, the highest safe dose according to sound medical judgment. Multiple doses of the pharmaceutical compositions of the invention are contemplated.

Determination of the optimal amount of compound to be administered to human or animal patients in need of prevention or treatment of an inflammation-based pathology, as well as methods of administering therapeutic or pharmaceutical compositions comprising such compounds, is well within the skill of those in the pharmaceutical, medical, and veterinary arts. Dosing of a human or animal patient is dependent on the nature of inflammation-based pathology, the patient's condition, body weight, general health, sex, diet, time, duration, and route of administration, rates of absorption, distribution, metabolism, and excretion of the compound, combination with other drugs, severity of the inflammation-based pathology, and the responsiveness of the disease state being treated, and can readily be optimized to obtain the desired level of effectiveness. The course of treatment can last from several days to several weeks or several months, or until a cure is effected or an acceptable diminution or prevention of the disease state is achieved. Optimal dosing schedules can be calculated from measurements of drug accumulation in the body of the patient in conjunction with the effectiveness of the treatment. Persons of ordinary skill can easily determine optimum dosages, dosing methodologies, and repetition rates. Optimum dosages can vary depending on the potency of the immunomodulatory polymeric compound, and can generally be estimated based on $ED_{50}$ values found to be effective in in vitro and in vivo animal models. Effective amounts of the present compounds for the treatment or prevention of inflammation-based pathologies, delivery vehicles containing these compounds, agonists, and treatment protocols, can be determined by conventional means. For example, the medical or veterinary practitioner can commence treatment with a low dose of the compound in a subject or patient in need thereof, and then increase the dosage, or systematically vary the dosage regimen, monitor the effects thereof on the patient or subject, and adjust the dosage or treatment regimen to maximize the desired therapeutic effect. Further discussion of optimization of dosage and treatment regimens can be found in Benet et al., in *Goodman & Gilman's The Pharmacological Basis of Therapeutics*, Ninth Edition, Hardman et al., Eds., McGraw-Hill, New York, (1996), *Chapter 1*, pp. 3-27, and L. A. Bauer, in *Pharmacotherapy, A Pathophysiologic Approach*, Fourth Edition, DiPiro et al., Eds., Appleton & Lange, Stamford, Conn., (1999), *Chapter 3*, pp. 21-43, and the references cited therein, to which the reader is referred.

In the context of the present invention, the terms "treatment," "therapeutic use," or "treatment regimen" as used herein are meant to encompass prophylactic, palliative, and therapeutic modalities of administration of the immunomodulatory polymers of the present invention, and include any and all uses of the presently claimed compounds that remedy a disease state, condition, symptom, sign, or disorder caused by an inflammation-based pathology, or which prevents, hinders, retards, or reverses the progression of symptoms, signs, conditions, or disorders associated therewith. Thus, any prevention, amelioration, alleviation, reversal, or complete elimination of an undesirable disease state, symptom, condition, sign, or disorder associated with an inflammation-based pathology is encompassed by the present invention.

A particular treatment regimen can last for a period of time which may vary depending upon the nature of the particular inflammation-based pathology, its severity, and the overall condition of the patient, and may involve administration of compound-containing compositions from once to several times daily for several days, weeks, months, or longer. Following treatment, the patient is monitored for changes in his/her condition and for alleviation of the symptoms, signs, or conditions of the disorder or disease state. The dosage of the composition can either be increased in the event the patient does not respond significantly to current dosage levels, or the dose can be decreased if an alleviation of the symptoms of the disorder or disease state is observed, or if the disorder or disease state has been ablated.

An optimal dosing schedule is used to deliver a therapeutically effective amount of the compounds of the present invention. For the purposes of the present invention, the terms "effective amount" or "therapeutically effective amount" with respect to the compounds disclosed herein refers to an amount of compound that is effective to achieve an intended purpose, preferably without undesirable side effects such as toxicity, irritation, or allergic response. Although individual patient needs may vary, determination of optimal ranges for effective amounts of pharmaceutical compositions is within the skill of the art. Human-doses can be extrapolated from animal studies (A. S. Katocs, *Remington: The Science and Practice of Pharmacy*, 19$^{th}$ Ed., A. R. Gennaro, ed., Mack Publishing Co., Easton, Pa., (1995), Chapter 30). Generally, the dosage required to provide a therapeutically effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any), and the nature and scope of the desired effect(s) (Nies et al., *Goodman & Gilman's The Pharmacological Basis of Therapeutics*, 9$^{th}$ Ed., Hardman et al., eds., McGraw-Hill, New York, N.Y., 1996, Chapter 3).

Prophylactic modalities for high risk individuals are also encompassed by the present invention. As used herein, the term "high risk individual" is meant to refer to an individual for whom it has been determined, via, e.g., individual or family history or genetic testing, living or working environment or conditions, etc., that there is a significantly higher than normal probability of being susceptible to an inflammation-based pathology or the onset or recurrence of an associated disease or disorder. For example, a patient could have a personal and/or family medical history that includes frequent occurrences of a particular disease or disorder. As another example, a patient could have had such a susceptibility determined by genetic screening according to techniques known in the art (see, e.g., U.S. Congress, Office of Technology Assessment, Chapter 5 In: *Genetic Monitoring and Screening in the Workplace*, OTA-BA-455, U.S. Government Printing Office, Washington, D.C., 1990, pages 75-99). As part of a treatment regimen for a high risk individual, the individual can be prophylactically treated to prevent inflammation-based pathologies or the onset or recurrence of the disease, disorder, sign, symptom, or condition. The term "prophylactically effective amount" is meant to refer to an amount of a pharmaceutical composition of the present invention that produces an effect observed as the prevention of infection or inflammation, or the onset or recurrence of a disease, symptom, sign, condition, or disorder. Prophylactically effective amounts of a pharmaceutical composition are typically determined by the effect they have compared to the effect observed when a second pharmaceutical composition lacking the active agent is administered to a similarly situated individual.

For therapeutic use, the immunomodulatory compounds disclosed herein can be administered to a patient suspected of suffering from an inflammation-based pathology in an amount effective to reduce the symptomology of the disease, symptom, sign, condition, or disorder. One skilled in the art can determine optimum dosages and treatment schedules for such treatment regimens by routine methods.

It should be noted that the present invention encompasses the use of both CP1 and Compound 15 in combination therapy with one another.

In the case of surgery- or trauma-related abscesses and adhesions, the methods of the present invention can be effectuated by administering multiple doses over a three week period preceding surgery, over a two week period preceding surgery, over a one week period preceding surgery, when the first dose is administered only 24 hours preceding surgery, and even when given only after exposure to bacteria. Further doses can be administered after surgery as well. Any regimen that results in an enhanced immune response to bacterial infection/contamination and subsequent abscess/adhesion formation can be used, although optimal doses and dosing regimens are those which would not only inhibit the development of abscess and/or adhesion formation, but also would result in a complete protection against abscess or adhesion formation by a particular bacterial organism or a variety of bacterial organisms. Desired time intervals for delivery of multiple doses of a particular polymer can be determined by one of ordinary skill in the art employing no more than routine experimentation.

Thus, the present invention is useful whenever it is desirable to prevent bacterial abscess or adhesion formation in a human or animal subject. This includes prophylactic treatment to prevent such conditions in planned surgical procedures, as well as in emergency situations. Elective surgeries include the following intraabdominal surgeries: right hemicolectomy; left hemicolectomy; sigmoid colectomy; subtotal colectomy; total colectomy; laparoscopic or open cholecystectomy; gastrectomy; caesarian section; etc. Emergency surgeries include those to correct the following conditions: perforated ulcer (duodenal or gastric); perforated diverticulitis; obstructive diverticulitis; acute appendicitis; perforated appendicitis; blunt abdominal trauma; penetrating abdominal trauma; second operation to drain abscess; etc. The methods of the present invention are also useful in nonintraabdominal surgeries such as cardiac surgeries and surgeries to correct wound infections. The present methods are also useful in connection with diseases that predispose a subject to abscess formation such as pelvic inflammatory disease, inflammatory bowel disease, urinary tract infections, and colon cancer. The present methods are therefore useful with abscesses of virtually any tissue or organ, including specifically, but not limited to, dermal abscesses such as acne. Those of ordinary skill in the art to which this invention pertains will readily recognize the range of conditions and procedures in which the present invention is applicable.

In another aspect, the present invention includes a method for inducing protection against postoperative surgical adhesion formation associated with many common types of surgery. The method includes the step of administering to a subject in need of such protection a pharmaceutical preparation containing an effective amount for reducing postoperative surgical adhesion formation of the immunomodulating polymer of the present invention. It is fully expected that administration of one or more such polymers at a site separate from the operative site will be effective in inducing protection against postoperative surgical adhesion formation. This is particularly surprising in view of previous observations, as discussed above.

PCT International Publication WO 00/59515 teaches that local administration of certain polymers into the surgical site is effective for reducing the incidence of postoperative surgical adhesions. In accordance with the present invention, an immunomodulatory polymer can be effective when given subcutaneously apart from the surgical site at which adhesions are likely to form.

The presently disclosed compounds can be administered in an effective amount for inducing protection against postoperative surgical adhesion formation. An effective amount for inducing protection against postoperative surgical adhesion formation as used herein is that amount of immunomodulating polymer of the present invention that will, alone or together with further doses or additional therapeutic compounds, inhibit or prevent the formation of postoperative surgical adhesion. It is believed that doses ranging from about one picogram/kilogram bodyweight to about one milligram/kilogram bodyweight, or from about one nanogram/kilogram bodyweight to about one microgram/kilogram bodyweight, will be effective, depending upon the mode of administration. The absolute amount will depend upon a variety of factors (including whether the administration is in conjunction with elective surgery or emergency surgery, concurrent treatment, number of doses, and individual patient parameters including age, physical condition, size and weight), and can be determined via routine experimentation. It is preferred generally that a maximum dose be used, that is, the highest safe dose according to sound medical judgment.

Multiple doses of the pharmaceutical compositions of the present invention are contemplated for inducing protection against postoperative surgical adhesion formation. Such multiple doses can be administered over a three day period beginning on the day preceding surgery. Further doses can be administered post surgery as well. Any regimen that results in a reduced postoperative surgical adhesion formation can be used, although optimum doses and dosing regimens are those which would not only inhibit the development of postoperative surgical adhesion formation, but would also result in complete protection against postoperative surgical adhesion formation. Desired time intervals for delivery of multiple doses of one of the present immunomodulatory polymers can be determined by one of ordinary skill in the art employing no more than routine experimentation.

Thus, the methods disclosed herein are useful whenever it is desirable to prevent postoperative surgical adhesion formation in a human or animal subject. This includes prophylactic treatment to prevent adhesion formation following planned surgical procedures, as well as following emergency operations. Elective surgeries include the following intraabdominal surgeries: right hemicolectomy; left hemicolectomy; sigmoid colectomy; subtotal colectomy; total colectomy; laparoscopic or open cholecystectomy; gastrectomy; pancreatectomy; splenectomy; liver, pancreas, small bowel, or kidney transplantation; lysis of adhesions; etc. Emergency intraabdominal surgeries include those to correct the following conditions: perforated ulcer (duodenal or gastric); perforated diverticulitis; obstructive diverticulitis; bowel obstruction; acute appendicitis; perforated appendicitis; blunt abdominal trauma; penetrating abdominal trauma; second operation to drain abscess; ruptured abdominal aortic aneurysm; etc. The methods of the present invention are also useful in the case of nonintraabdominal surgeries such as cardiac surgeries, open and endoscopic orthopedic surgeries, neurosurgeries, gynecologic and pelvic surgeries, and surgeries to correct wound infections. The present methods are also useful in connection with diseases that predispose a subject to spontaneous adhesion formation, such as pelvic inflammatory disease, inflammatory bowel disease, urinary tract infections, and colon cancer. The present methods are thus useful with inflammatory processes involving virtually any tissue or organ.

When administered to prevent postoperative surgical adhesion formation, the compounds of the present invention can be administered either distant from the operative site, including systemically, or locally into the operative site at which it is desirable to reduce the likelihood of postoperative surgical adhesion formation. The compounds of the present invention can be administered as an aqueous solution, as a crosslinked gel, or as any temporal or physical combination of aqueous solution and crosslinked gel forms.

The preparations of the present invention can be administered "in conjunction with" infection, meaning close enough in time with the surgery, trauma, or diseases that predispose the host to abscess or adhesion formation so that a protective effect against abscess or adhesion formation is obtained. The preparations can be administered long before surgery in the case of elective surgery (i.e., weeks or even months), preferably with booster administrations closer in time to (and even after) the surgery. Particularly in emergency situations, the preparations can be administered immediately before (minutes to hours) and/or after the trauma or surgery. It is important only that the preparation be administered close enough in time to the surgery so as to enhance the subject's immune response against bacterial infection/contamination, thereby increasing the chances of a successful host response and reducing the likelihood of abscess or adhesion formation.

Those of ordinary skill in the art to which this invention pertains will recognize that the present methods can be applied to a wide range of diseases, symptoms, conditions, signs, disorders, and procedures. Besides abscesses and adhesions, other inflammatory processes and pathologies to which the compounds, compositions, and methods of the present invention can be applied include: sepsis; rheumatoid arthritis; myesthenia gravis; inflammatory bowel disease; colitis; systemic lupus erythematosis; multiple sclerosis; coronary artery disease; diabetes; hepatic fibrosis; psoriasis; eczema; acute respiratory distress syndrome; acute inflammatory pancreatitis; endoscopic retrograde cholangiopancreatography-induced pancreatitis; burns; atherogenesis of coronary, cerebral, and peripheral arteries; appendicitis; cholecystitis; diverticulitis; visceral fibrotic disorders (liver, lung, intestinal); wound healing; skin scarring disorders (keloids, hidradenitis suppurativa); granulomatous disorders (sarcoidosis, primary biliary cirrhosis); asthma; pyoderma gangrenosum; Sweet's syndrome; Behcet's disease; primary sclerosing cholangitis; and cell, tissue, or organ transplantation.

Formulations

The compounds of the present invention can be administered in pharmaceutically or physiologically acceptable solutions that can contain pharmaceutically or physiologically acceptable concentrations of salts, buffering agents, preservatives, compatible carriers, and optionally, other therapeutic ingredients. The synthetic PG (Compound 15) of the present invention is soluble up to ca. 20 mg/mL in water at neutral pH. Furthermore, aqueous solutions of this compound can accommodate low (about 0.5 to about 5) weight percentages of glycerol, sucrose, and other such pharmaceutically acceptable excipient materials. CP1 and the SPA Compound 15 disclosed herein can thus be formulated in a variety of standard pharmaceutically acceptable parenteral formulations.

The pharmaceutical compositions of the present invention can contain an effective amount of CP1 or the presently disclosed SPA, optionally included in a pharmaceutically or physiologically acceptable carrier, excipient, or diluent. The term "pharmaceutically or physiologically acceptable carrier, excipient, or diluent" means one or more compatible solid or liquid fillers, dilutants, or encapsulating substances that are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the polymers of the present invention, and with each other, in a manner such that there is no interaction that would substantially impair the desired pharmaceutical efficiency of CP1 or the SPA.

Compositions suitable for parenteral administration conveniently comprise sterile aqueous preparations, which can be isotonic with the blood of the recipient. Among the acceptable vehicles and solvents are water, Ringer's solution, and isotonic sodium chloride solution. In addition, sterile, fixed oils are conventionally employed as a solvent or suspending medium. For this purpose, any bland fixed oil can be employed, including synthetic mono- or di-glycerides. In addition, fatty acids such as oleic acid are useful in the preparation of injectables. Carrier formulations suitable for subcutaneous, intramuscular, intraperitoneal, intravenous, etc. administrations can be found in Remington: The Science and Practice of Pharmacy, 19th Edition, A. R. Gennaro, ed., Mack Publishing Co., Easton, Pa., (1995). CP1 and the SPA polymer of the present invention can be delivered individually, or in a mixture comprising the two polymers.

A variety of administration routes are available. The particular mode selected will depend upon whether CP1 or the present SPA is selected, the particular condition being treated, and the dosage required for therapeutic efficacy. Generally speaking, the methods of the present invention can be practiced using any mode of administration that is medically acceptable, meaning any mode that produces effective levels of an immune response without causing clinically unacceptable adverse effects. Preferred modes of administration are parenteral routes. The term "parenteral" includes subcutaneous, intravenous, intramuscular, or intraperitoneal injection, or infusion techniques.

The compositions can be conveniently presented in unit dosage form or dosage unit form, and can be prepared by any of the methods well known in the art of pharmacy. All methods include the step of bringing CP1 or the SPA into association with a carrier that constitutes one or more accessory ingredients. In general, the compositions are prepared by uniformly and intimately bringing CP1 or the SPA into association with a liquid carrier, a finely divided solid carrier, or both, and then, if necessary, shaping the product. CP1 or the SPA can be stored lyophilized.

Other delivery systems can include time-release, delayed-release, or sustained-release delivery systems. Such systems can avoid repeated administrations of the anti-inflammatory agent, increasing convenience to the subject and the physician. Many types of release delivery systems are available and known to those of ordinary skill in the art, including polymer-based systems such as poly(lactide-glycolide), copolyoxalates, polycaprolactones, polyesteramides, polyorthoesters, polyhydroxybutyric acid, and polyanhydrides.

Microcapsules of the foregoing polymers containing drugs are described in, for example, U.S. Pat. No. 5,075,109. Delivery systems also include non-polymer systems such as: lipids, including sterols such as cholesterol, cholesterol esters, and fatty acids or neutral fats such as mono-, di-, and tri-glycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5, 736,152, and (b) diffusional systems in which an active component permeates at a controlled rate from a polymer such as described in U.S. Pat. Nos. 3,854,480, 5,133,974 and 5, 407,686. In addition, pump-based hardware delivery systems can be used, some of which are adapted for implantation.

The foregoing descriptions provide a comprehensive overview of the many aspects of the present invention. The following examples illustrate various aspects thereof and are not intended, nor should they be construed, to be limiting thereof in any way.

Example 1

A general procedure for preparing SPA precursor 14 described in PCT International Publication Number WO 01/79242. The synthetic approach used herein is outlined in Scheme I and exemplified below.

Scheme I
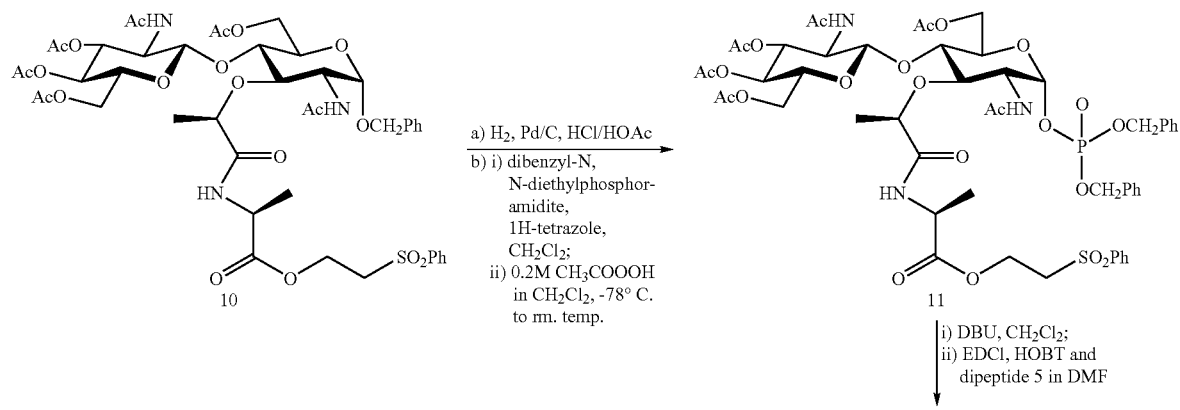
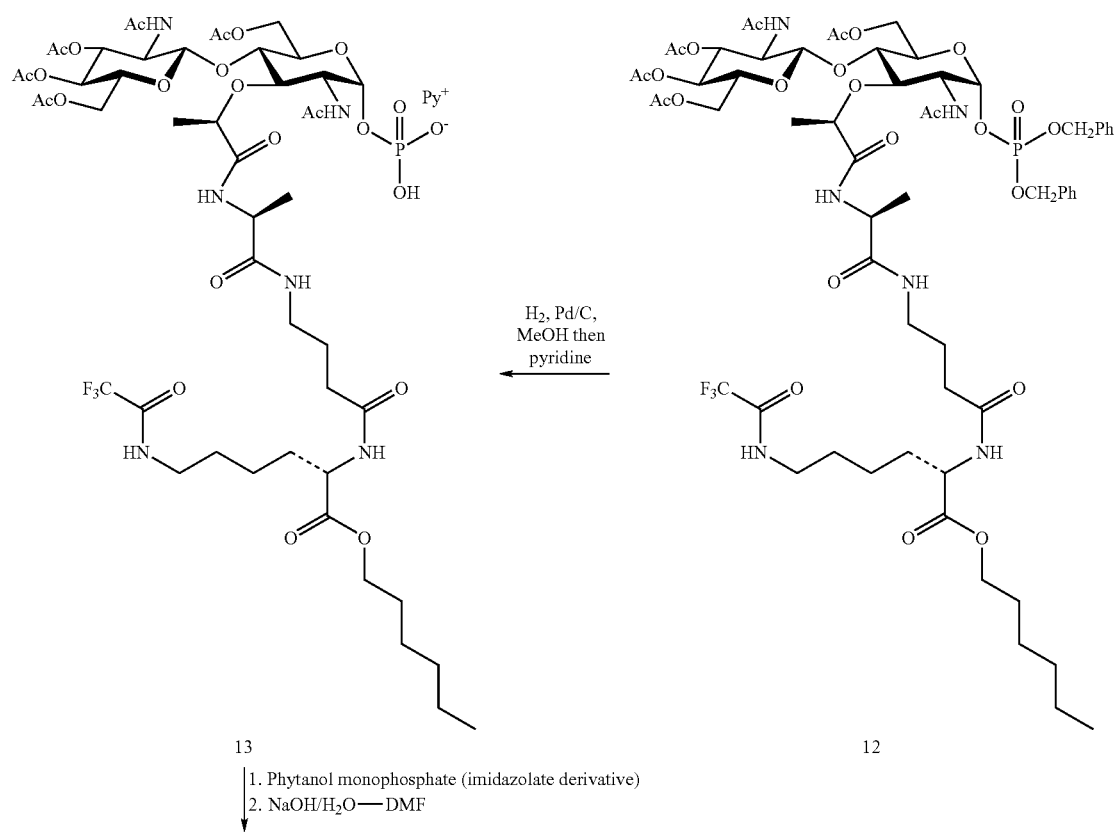

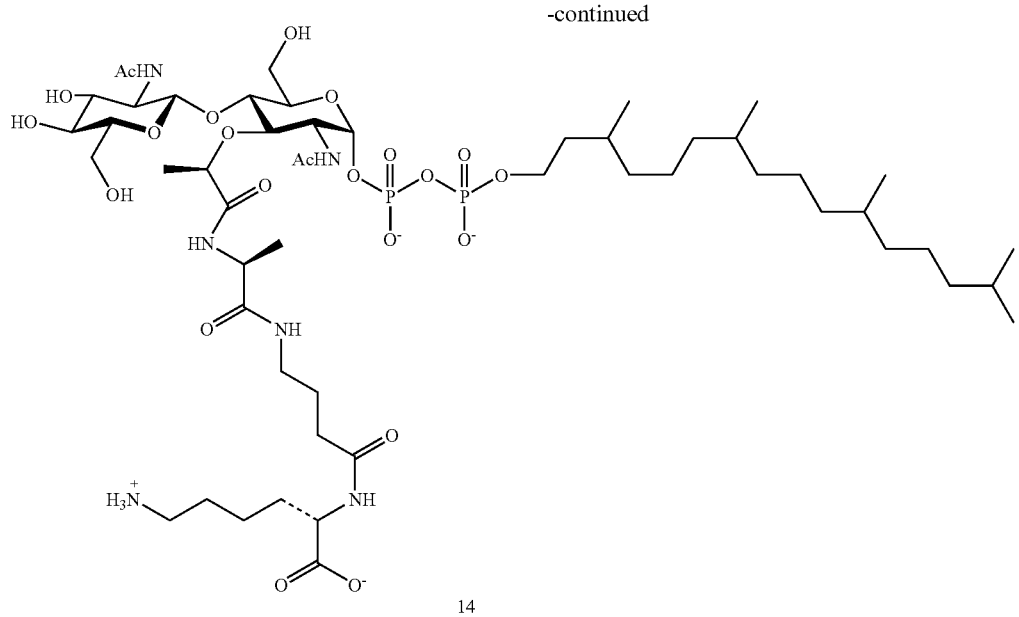

14

| Definitions | |
|---|---|
| DBU | 1,8-diazabicyclo[5.4.0]undec-7-ene |
| HOBT | N-hydroxybenzotriazole |
| EDCI | 1-[3-(dimethyamino)propyl]-3-ethylcarbodiimide hydrochloride |
| Py+ | protonated pyridine |
| Ac | acetyl |
| Ph | phenyl |
| NHS | N-hydroxysuccinimide |
| TLC | thin-layer chromatography |
| TFA | trifluoroacetic acid |
| THF | tetrahydrofuran |
| DMF | dimethyl formamide |
| RP/HPLC | reverse-phase HPLC |
| DMAP | 4-dimethylaminopyridine |
| NH(TFA) | NHC(O)CF$_3$ |

General Experimental Conditions

Reactions are carried out with continuous stirring under a positive pressure of nitrogen, except where noted. Reagents and solvents are purchased and used without further purification, except as noted. TLC is performed using 0.25 mm silica gel 60 plates from E. Merck with a 254 nm fluorescent indicator. Solvent system specifications are expressed as percents or ratios by volume. Plates are developed in a covered chamber and visualized by ultraviolet light or by treatment with 5% phosphomolybdic acid in ethanol, with ceric ammonium molybdate in aqueous sulfuric acid, or in the cases of amino acid and peptide derivatives with ninhydrin in acetic acid/n-butanol. All such visualization treatments are followed by heating. Flash chromatography is carried out with silica gel 60, 230-400 mesh (0.040-0.063 mm particle size) purchased from EM Science or with commercial Biotage pre-packaged 32-63 mμ KP-Sil cartridges. HPLC analyses and purifications are performed using Waters X-Terra C8 columns with the specified solvent system and flow rate.

NMR spectra are reported as chemical shifts in parts-per-million (ppm) downfield from a tetramethylsilane internal standard (0 ppm). $^1$H NMR spectra are recorded in the solvent indicated on a Bruker Avance spectrometer at 500.2 MHz, a Varian Mercury spectrometer at 400.21 MHz, or a GE QE-300 spectrometer at 300.2 MHz. Electrospray mass spectra (ES/MS) are recorded on a Micromass Platform LCZ spectrometer. High resolution mass spectra are recorded on a Micromass QTOF mass spectrometer.

Peptide Starting Material

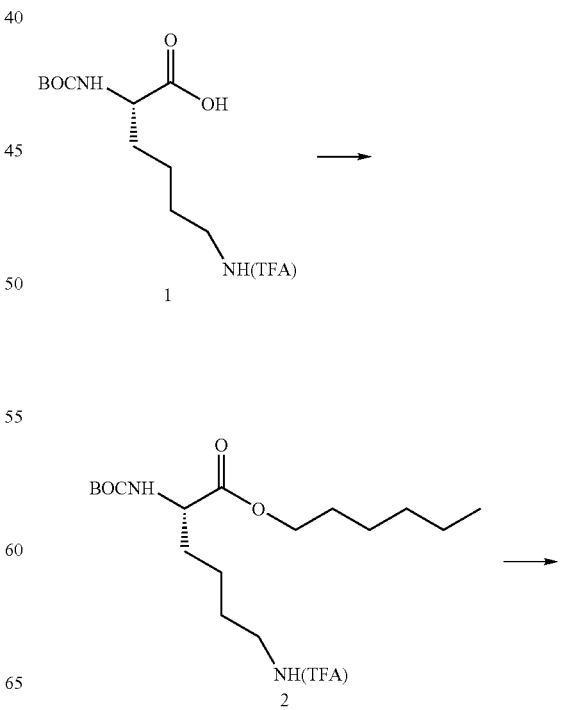

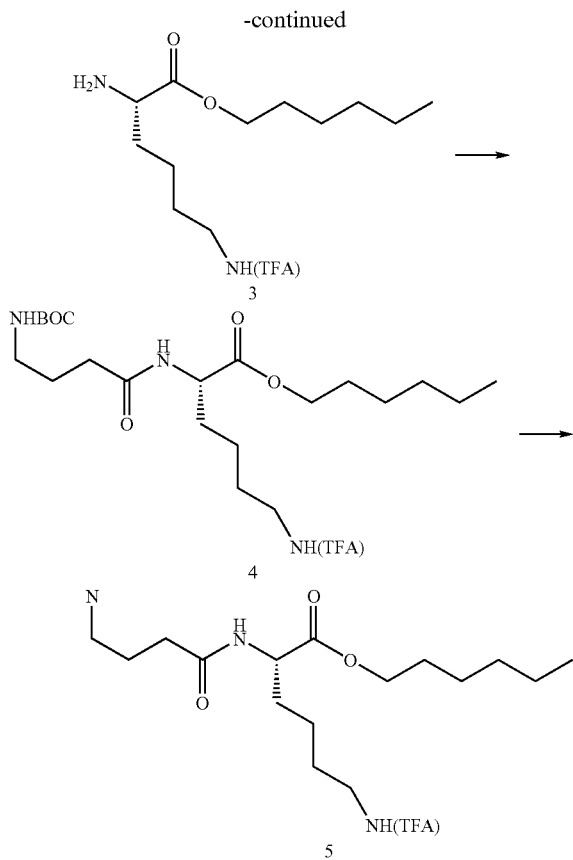

A flask is charged with DMF (117 mL) and compound 1 (20 g, 58.4 mMol). K$_2$CO$_3$ (12.1 g, 87.5 mMol) and 1-bromohexane (16.7 mL, 119 mMol) are added with vigorous stirring and the mixture is heated to 45° C. After 5 hr the reaction is complete as evidenced by TLC analysis (25% ethyl acetate in hexanes). The mixture is cooled to room temperature and diluted with ethyl acetate. The solids are filtered under suction and the filtrate is washed successively with water (1×), N HCl (3×), and 0.5M pH 7 buffer (1×). The organic phase is dried (MgSO$_4$) and concentrated in vacuo to a thick oil which solidifies on standing. The oil is taken up in dichloromethane and crystallized from hexanes and dichloromethane. The crystals are dried in vacuo to afford compound 2 (24.3 g, 97%). $^1$H NMR (400 MHz, CDCl$_3$) δ 6.51 (br s, 1H), 5.09 (d, 1H, J=7.5 Hz), 4.28 (m, 1H), 4.13 (t, 2H, J=6.8 Hz), 3.37 (m, 2H), 1.82 (m, 1H), 1.64 (m, 6H), 1.44 (s, 9H), 1.31 (m, 6H), 0.89 (t, 3H, J=7.0 Hz); ES/MS m/z=427.1 [M+H]$^+$, 425.2 [M−H]$^−$.

Trifluroracetic acid (62 mL, excess) is added to a stirred solution of compound 2 (17.1 g, 13.1 mMol) in dichloromethane (200 mL) at 0° C. The cooling bath is removed and the reaction mixture is stirred 2 hr at ambient temperature. TLC analysis (50% ethyl acetate in hexanes) indicates the absence of starting material. The reaction mixture is transferred to a beaker and layered with water. The pH is adjusted to 9 with aqueous NaOH. The organic phase is separated, and the aqueous phase extracted (2×) with dichloromethane. The organic phase is dried (MgSO$_4$), and concentrated in vacuo to afford compound 3 as a thick oil (13.7 g, 95%), which is taken directly to the coupling step. ES/MS m/z=327.2 [M+H]$^+$, 325.2 [M−H]$^−$.

EDCI {1-[3-(dimethyamino)propyl]-3-ethylcarbodiimide hydrochloride} (7.65 g, 39.9 mMol) is added to a stirred solution of N-BOC-γ-aminobutyric acid (7.95 g, 39.1 mMol) and NHS (4.59 g, 39.9 mMol) in DMF (120 mL) at room temperature. Stirring is continued overnight, at which time the reaction is judged to be complete by TLC analysis (10% methanol in chloroform). The crude compound 3 (12.8 g, 39.1 mMol) is added in DMF (75 mL), using 5 mL DMF to aid the transfer, followed by diisopropylethyl amine (7.24 mL, 43.0 mMol). After 4 hr the reaction is complete, as judged by TLC analysis (10% methanol in chloroform). The reaction mixture is diluted with ethyl acetate, then washed with water (1×), N HCl (2×), and water (1×). The combined aqueous extracts are washed with a single portion of ethyl acetate. The combined organic extracts are washed with brine, dried (Na$_2$SO$_4$), and concentrated in vacuo. The residue is chromatographed (Biotage 65M; step gradient: 1:1 ethyl acetate:hexanes followed by 5% MeOH in ethyl acetate). Appropriate fractions are combined and concentrated in vacuo to afford pure compound 4 (17.7 g, 89%). ES/MS m/z=512.1 [M+H]$^+$, 510.1 [M−H]$^−$.

Trifluoroacetic acid (5.1 mL, excess) is added to a stirred solution of compound 4 (1.69 g, 3.31 mMol) in dichloromethane (33 mL) at 0° C. The cooling bath is removed and the mixture stirred at ambient temperature for 30 min, at which time the reaction is complete as judged by TLC analysis (10% methanol in chloroform). The dichloromethane solution is transferred to a beaker, layered with water, and the pH adjusted to 9 with aqueous NaOH. The organic phase is drawn off and the aqueous phase is extracted with dichloromethane. The combined organic extracts are dried (Na$_2$SO$_4$) and concentrated in vacuo to afford compound 5 as a thick oil (quantitative yield). ES/MS m/z=412.3 [M+H]$^+$, 410.2 [M−H]$^−$.

Phytanol Phosphate Triethylammonium Salt Starting Material

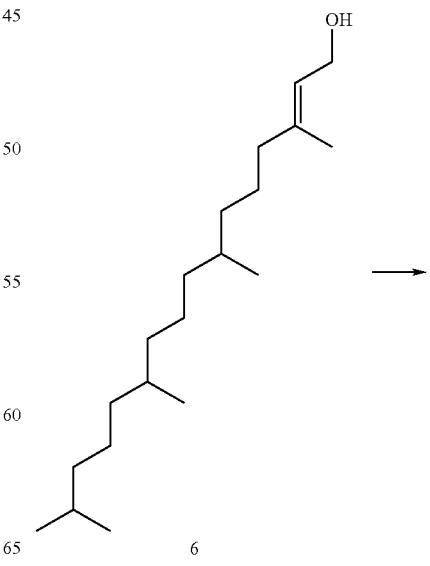

-continued

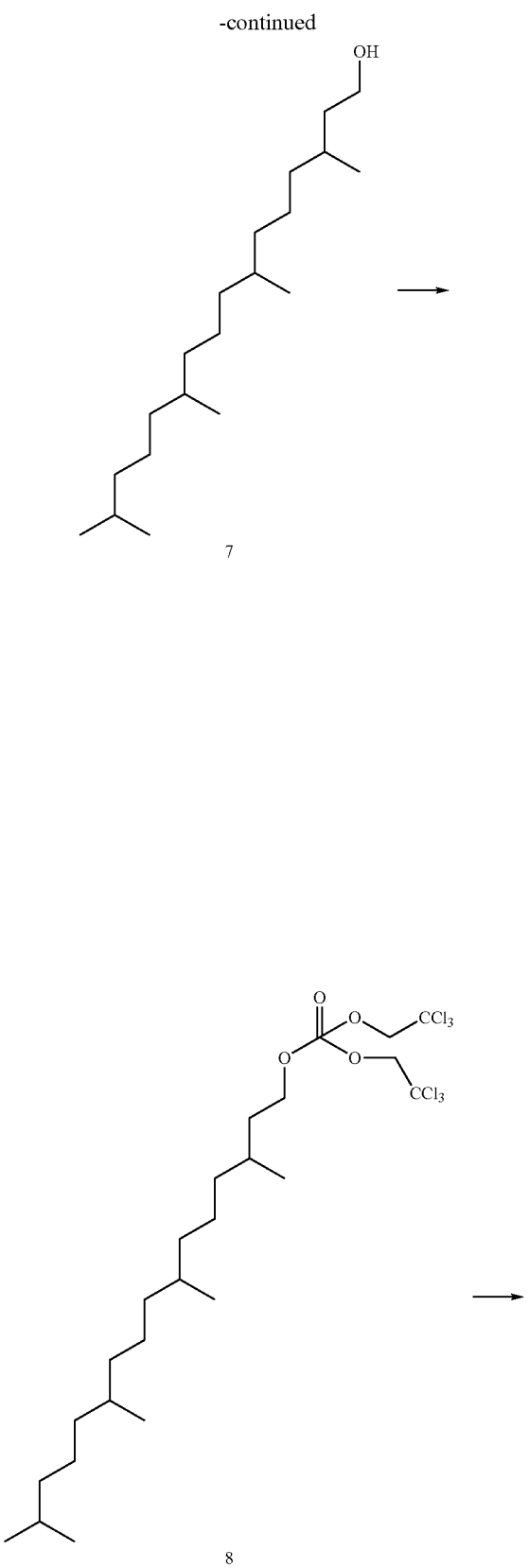

7

8

-continued

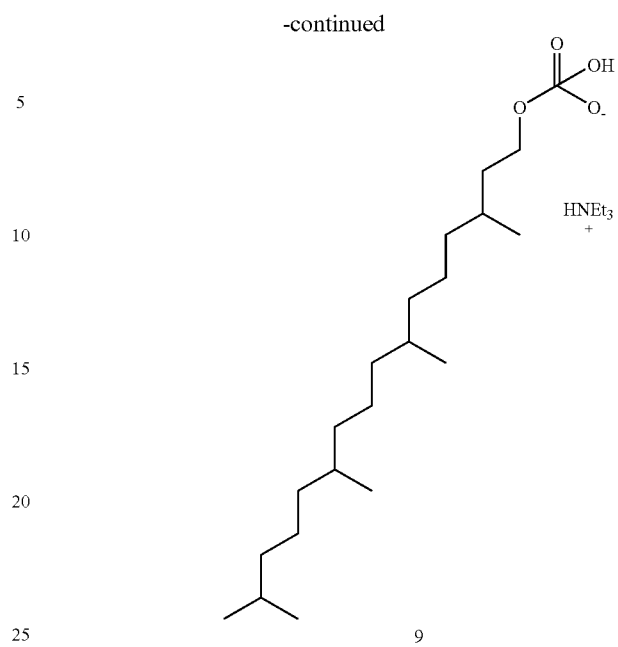

9

Phytol 6 (5.0 g, 16.9 mMol) in ethanol (20 mL) is added to a stirred slurry of Raney Ni (about 500 mg) in ethanol (10 mL). The system is brought under a hydrogen atmosphere at balloon pressure at room temperature and stirring is continued overnight. About 50 µL of reaction mixture is removed, filtered through a syringe filter, and concentrated under a nitrogen stream. $^1$H nmr analysis confirms the disappearance of the phytol vinylic hydrogen absorption. The reaction mixture is filtered through celite and concentrated in vacuo to a yellow oil. The oil is adsorbed on silica gel 60 (10 g) and flash-chromatographed over silica gel 60 (10 g) using a gradient elution (hexanes to 10% ethyl acetate in hexanes). Appropriate fractions are combined and concentrated in vacuo to afford pure phytanol 7 (4.57 g, 90.5%) as a colorless oil. $^1$H NMR (400 MHz, CDCl$_3$) δ 3.68 (m, 2H), 1.46 (m, 25H), 0.74 (m, 15H).

Bis(2,2,2-trichloroethyl)phosphorochloridate (18.7 g, 49.2 mMol) is added to a stirred solution of compound 7 (9.80 g, 32.8 mMol) and DMAP (802 mg, 6.56 mMol) in dichloromethane. After cooling the solution to 0° C., triethylamine (13.7 mL, 98.4 mMol) is added dropwise via syringe. The cooling bath is removed and the reaction mixture is stirred overnight at ambient temperature, at which point TLC analysis (10% ethyl acetate in hexanes) indicates complete reaction. The mixture is then diluted with dichloromethane, washed with N HCl (3×), and the aqueous layer is back extracted with dichloromethane. The combined organic extracts are dried (MgSO$_4$) and concentrated to an oil. The oil is chromatographed over silica gel 60 (50 g) using a gradient of hexanes to 15% ethyl acetate in hexanes. Appropriate fractions are combined and concentrated in vacuo to afford bis(2,2,2-trichloroethyl)phytanyl phosphate 8 (20.2 g, 96%) as a colorless oil. $^1$H NMR (400 MHz, CDCl$_3$) δ 4.62 (m, 4H), 4.31 (m, 2H), 1.80 (m, 1H), 1.56 (m, 4H), 1.27 (m, 20H), 0.86 (m, 15H); ES/MS m/z=641.2 [M+H]$^+$, 662.2 [M+Na]$^+$.

An HCl/THF solution is prepared by bubbling HCl(g) through anhydrous THF at 0° C. for 2 min. The HCl/THF solution (20 mL) is added portionwise to a stirred suspension of compound 8 (20.1 g, 31.3 mMol) and Zn° dust (24.5 g, 375.6 g-atom) at 0° C. in THF (300 mL). Gas evolution is evident upon each addition. After 1 hr, the Zn° forms small clods in the reaction mixture, and TLC analysis (25% ethyl acetate in hexanes) indicates complete reaction. The reaction mixture is filtered thorough celite, concentrated to about ¼ volume, and diluted with ethyl acetate. The organic solution is washed with 1N HCl (3×) and dried (MgSO$_4$). After removal of the MgSO$_4$ by suction filtration, triethylamine (4.6 mL, 32.9 mMol) is added and the system is then concentrated to a colorless foam. The product is co-distilled with dichloromethane and toluene and then evacuated (<30 Torr) at room temperature overnight to yield phytanyl phosphate triethylamine salt 9. $^1$H NMR (400 MHz, CDCl$_3$) δ 8.74 (m, 1H), 5.06 (br, 1H), 4.04 (t, 2H, J=6.5 Hz), 3.28 (dt, 6H, J=9.7, 5.5 Hz), 1.68 (m, 1H), 1.52 (m, 2H), 1.38 (t, 9H, J=7.3 Hz), 1.24 (m, 12H), 1.10 (m, 9H), 0.86 (m, 15H); ES/MS m/z=377.3 [M−H]$^-$.

Lactol Intermediate related substance impurity at about 20%. The substance is taken forward with the desired product and removed via purification of a subsequent intermediate. $^1$H NMR (400 MHz, CDCl$_3$) δ 8.22 (d, 1H, J=3.4 Hz), 7.93 (dt, 2H, J=6.3, 1.7 Hz), 7.70 (dt, 1H, J=7.4, 1.5 Hz), 7.61 (m, 2H), 7.40 (t, 1H, J=6.1 Hz), 7.17 (m, 1H), 6.05 (d, 1H, J=9.7 Hz), 5.58 (d, 1H, J=3.4 Hz), 5.10 (m, 2H), 2.35 (s, 3H), 2.14 (s, 3H), 2.05 (s, 3H), 2.03 (s, 3H), 2.02 (s, 3H), 1.96 (s, 3H), 1.37 (m, 6H); ES/MS m/z=904.4 [M+H]$^+$, 902.3 [M−H]$^-$.

Monopeptide Dibenzyl Phosphate Intermediate

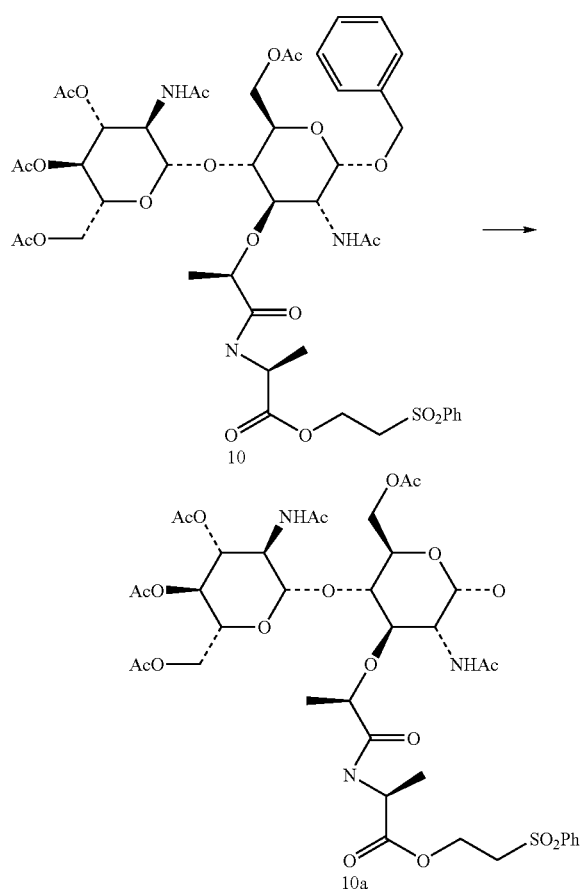

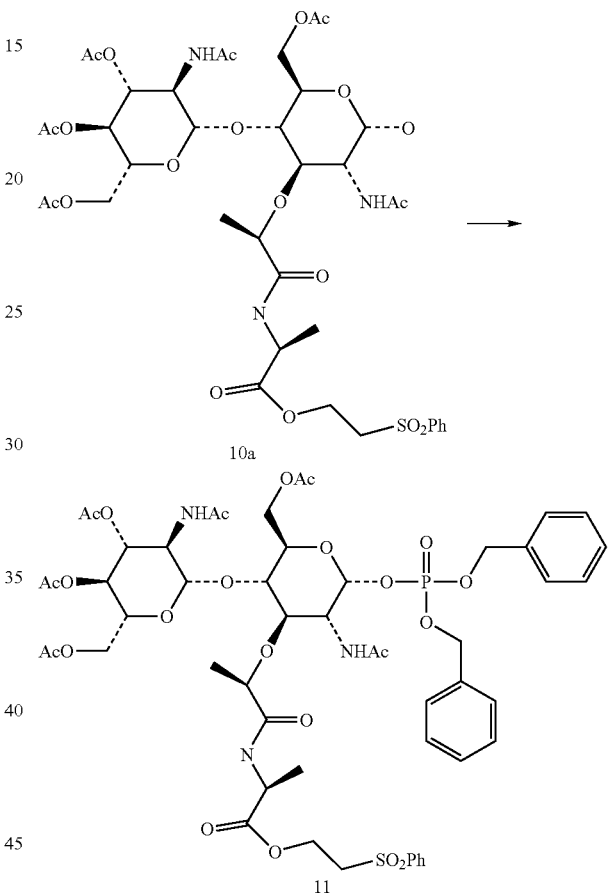

The orthogonally-protected disaccharide monopeptide 10 (Saha et al. 2001 *Organic Lett.* 3: 3575) (12.0 g, 12.1 mMol) is added to a stirred suspension of 10% Pd/C (6.0 g) in 0.23 M HCl in acetic acid (120 mL). The reaction mixture is stirred under an atmosphere of hydrogen (balloon pressure) at 25° C. for 1.5 hr. Analysis of the reaction mixture by TLC (5% MeOH/CHCl$_3$) shows complete consumption of starting material. The reaction mixture is filtered through a pad of Celite, concentrated to about ¼ volume and diluted with methylene chloride. The organic solution is washed with aqueous NaHCO$_3$ (×3) and water (×2). The aqueous extracts are combined and extracted with methylene chloride. The combined organic layers are washed with brine, dried with Na$_2$SO$_4$, and concentrated in vacuo to afford the lactol product 10a as a white solid (10.2 g, 94% by mass). Inspection of the $^1$H NMR spectrum reveals the presence of an unidentified Compound 10a (13.7 g, 15.2 mMol) in anhydrous dichloromethane (60 mL) is added rapidly via pressure-equalizing dropping funnel to a vigorously stirred suspension of tetrazole (4.0 g, 57.8 mMol) and dibenzyl N,N'-diethylphosphoramidite (10.4 mL, 29.5 mMol) in anhydrous dichloromethane (40 mL) under argon at 25° C. The reaction mixture becomes homogeneous within a few minutes. After 2 hr, TLC (5% MeOH/CHCl$_3$) shows a complete reaction. The mixture is cooled to −78° C., and 0.2M peracetic acid in methylene chloride (190 mL) is added dropwise over 10 min with vigorous stirring. After the addition is complete, the cooling bath is removed and the mixture allowed to warm to room temperature over 2 hr. TLC (5% MeOH/CHCl$_3$) shows complete reaction. The mixture is diluted with methylene chloride and extracted: ice-cold saturated Na$_2$S$_2$O$_3$ (1×), N HCl (1×) and water (1×). The combined aqueous extracts are back-extracted once with methylene chloride. The combined methylene chloride solutions are dried over MgSO$_4$ and concentrated in vacuo to a colorless oil. The crude product is adsorbed on pyridine-deactivated silica gel and chromatographed over pyridine-deactivated silica gel using a gradient elution (chloroform to 5% methanol in chloroform). Evaporation of solvent provides the pure monophosphate triester 11 (12.4 g, 70%) as a colorless solid. $^1$H NMR (400 MHz, CDCl$_3$) δ 7.88 (d, 2H, J=7.3 Hz), 7.67 (t, 1H, J=7.6 Hz), 7.57 (t, 2H, J=7.7 Hz), 7.33 (m, 10H), 7.18 (d, 1H, J=7.4 Hz), 5.98 (m, 2H), 5.14 (m, 2H), 5.05 (dd, 2H, J=8.2, 3.1 Hz), 5.00 (d, 2H, J=8.1 Hz) 4.53 (m, 2H), 4.37 (m, 3H), 4.29 (dd, 1H, J=12.3, 4.1 Hz), 4.02 (m, 8H), 3.61 (d, 1H, J=8.8 Hz), 3.52 (dd, 1H, J=10.9, 8.6 Hz), 3.33 (t, 2H, J=5.8 Hz), 2.05 (s, 3H), 2.04 (s, 3H), 2.02 (s, 3H), 2.00 (s, 3H), 1.95 (s, 3H), 1.81 (s, 3H), 1.37 (d, 3H, J=6.4 Hz), 1.33 (d, 3H, J=7.3 Hz); ES/MS m/z=1164.6 [M+H]$^+$, 1186.6 [M+Na]$^+$, 886.6 [glycosyl]$^+$, 1162.6 [M−H]$^-$.

Disaccharide Tripeptide Dibenzyl Phosphate Intermediate

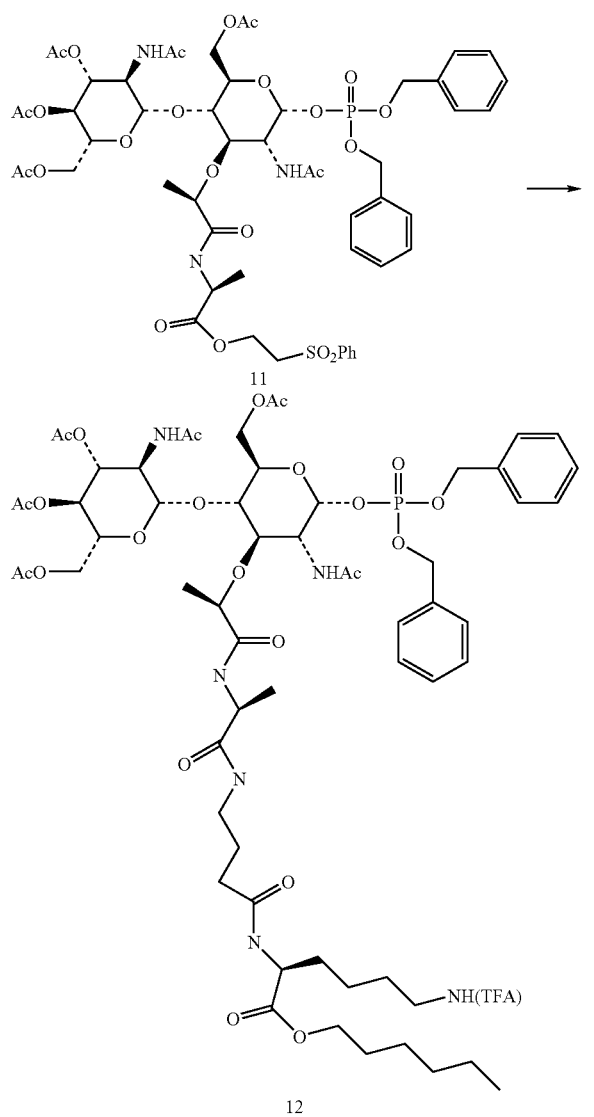

DBU (1.30 mL, 8.57 mMol) is added dropwise to a solution of monophosphate triester 11 (9.07 g, 7.79 mMol) in dichloromethane (78 mL) under an argon atmosphere. After 15 min, TLC (10% MeOH/CHCl$_3$) shows complete consumption of the starting material. The reaction solution is diluted with dichloromethane and washed twice with 1N HCl. The organic layer is dried (Na$_2$SO$_4$) and concentrated in vacuo, affording the acid analog of compound 11 as a foam (6.73 g, 87%). ES/MS m/z=1018.6 [M+Na]$^+$, 718.5 [glycosyl]$^+$, 994.6 [M−H]$^-$.

The acid analog (2.32 g, 2.33 mMol), peptide 5 (1.05 g, 2.56 mMol) and N-hydroxy-benzotriazole (315 mg, 2.33 mMol) are dissolved in anhydrous DMF (23 mL) at 0° C. EDCI (491 mg, 2.56 mMol) is added and the reaction mixture is stored at −20° C. for 48 hr. Analysis of the reaction mixture by TLC (15% MeOH/CHCl$_3$) reveals complete consumption of the starting material. The reaction mixture is concentrated in vacuo, redissolved in ethyl acetate, and washed sequentially with water (2×), N HCl (2×), water and brine. The organic solution is dried with MgSO$_4$ and concentrated to a foam. The foam is adsorbed on pyridine-deactivated silica gel and chromatographed over pyridine-deactivated silica gel using a gradient of chloroform to 4% methanol in chloroform. Evaporation of solvent affords compound 12 (2.33 g, 72%) as a white solid. $^1$H NMR (400 MHz, CDCl$_3$) δ 7.34 (m, 10H), 6.74 (t, 1H, J=5.9 Hz), 6.45 (d, 1H, J=9.3 Hz), 5.97 (dd, 1H, J=5.4, 3.2 Hz), 5.07 (m, 5H), 2.06 (s, 3H), 2.05 (s, 3H), 2.02 (s, 3H), 1.84 (s, 3H), 0.88 (t, 3H, J=7.0 Hz); ES/MS m/z=1389.8 [M+H]$^+$, 1412.8 [M+Na]$^+$, 1111.7 [glycosyl]$^+$, 1387.7 [M−H]$^-$.

Disaccharide Tripeptide Phosphate Monopyridyl Salt Intermediate

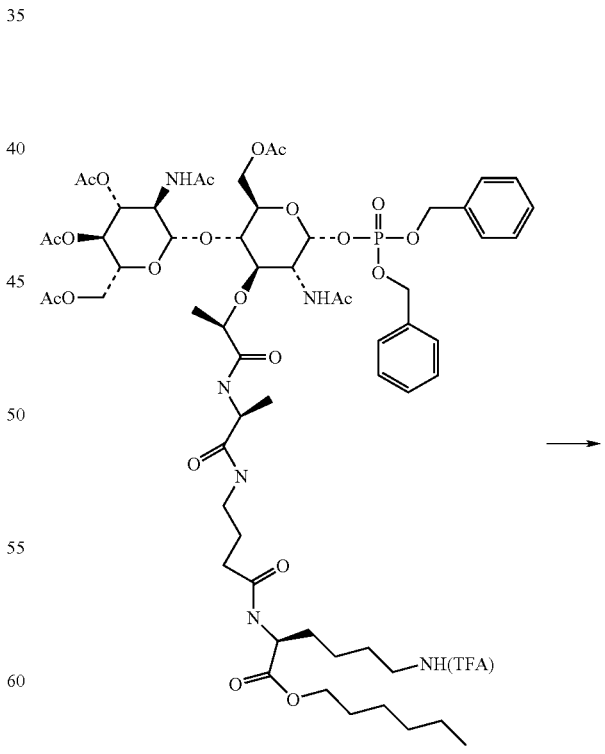

-continued

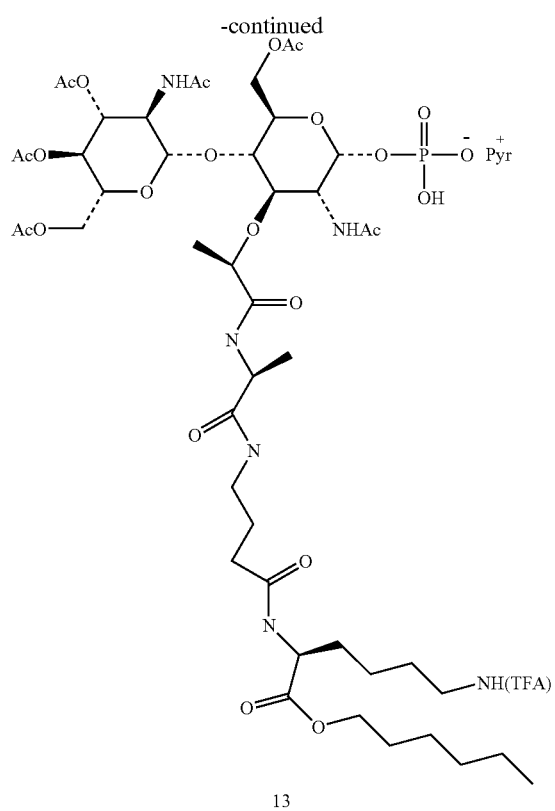

13

The disaccharide tripeptide dibenzyl phosphate 12 (7.25 g, 5.22 mMol) in methanol (30 mL) is added to a suspension of 10% Pd/C (3.63 mg) in methanol (25 mL), cooled in an ice bath to aid in degassing the reaction solution. The solution is then warmed to room temperature and hydrogenated at balloon pressure for 2 hr. The catalyst is removed by filtration through celite and the filtrate is treated with pyridine (1.0 mL). The resulting mixture is concentrated to a white solid, which is collected and dried under high vacuum for 16 hr to afford compound 13 (6.32 g, 94%). $^1$H NMR (400 MHz, CDCl$_3$) δ 8.73 (m, 2H), 7.96 (m, 1H), 7.56 (m, 2H), 5.88 (m, 1H), 2.09 (s, 3H), 2.04 (s, 3H), 2.02 (s, 3H), 2.01 (s, 3H), 1.95 (s, 3H), 1.94 (s, 3H), 0.88 (t, 3H, J=6.8 Hz).

ES/MS m/z=1209.7 [M+H]$^+$, 1232.8 [M+Na]$^+$, 1111.8 [glycosyl]$^+$, 1207.6 [M−H]$^−$ Modified Lipid II Intermediate

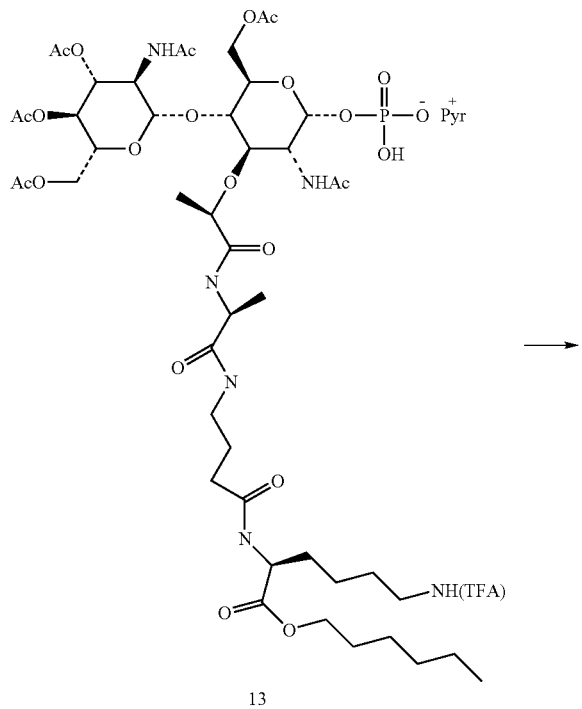

13

→

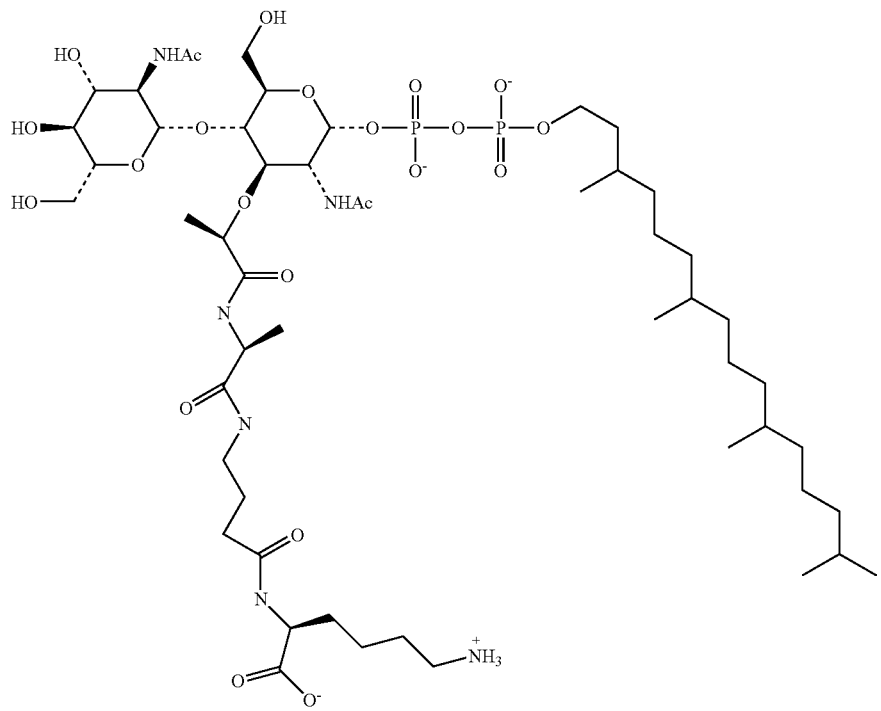

14

To a stirred solution of phytanol phosphate triethylamine salt 9 (57 mg, 0.118 mMol) in dichloromethane (1.2 mL) at room temperature is added carbonyl diimidazole (15 mg, 0.094 mMol). The reaction mixture is stirred overnight. $^1$H NMR analysis indicates an 85:15 mixture of imidazolate derivative and starting phosphate as evidenced by the chemical shifts of the protons on the oxygen-bearing carbon (phosphate at 3.993 ppm, imidazolate at 3.818 ppm). The crude imidazolate is concentrated in vacuo, taken up in THF to 0.7 mL/mequiv, and used as thus obtained.

The crude imidazolate solution (1.0 mL, 1.5 equiv) is added to a solution of monopyridyl salt 13 (450 mg, 0.349 mMol) in DMF (0.35 mL) and THF (1.5 mL) at room temperature. Vacuum dried 4,5-dicyanoimidazole (103 mg, 0.873 mMol) is added and the reaction mixture stirred at room temperature for 18 hr. Imidazolate solution (0.7 mL, 1.0 equiv) is added and stirring continued for 23 hr. The reaction is complete as evidenced by RP/HPLC analysis:

Waters Xterra C8 analytical column—(4.6 mm×250 mm×5 μm)

Gradient—1:1=50 mM aq. NH$_4$HCO$_3$/MeOH to MeOH

Rate—1 mL/min, λ=214 nm, 2 μL reaction mix

Chart—Starting Material @ 10 min, Product @ 20 min

The crude pyrophosphate product is taken on without further manipulation.

Aqueous NaOH (1.0N, 4.4 mL) is added to the stirred reaction mixture and stirring is continued while the reaction course is monitored until starting material is consumed as evidenced by RP/HPLC (vide supra). At completion, the reaction mixture is diluted with 50 mM aqueous NH$_4$HCO$_3$, transferred to a separatory funnel, and extracted with ether (3×). The aqueous phase is lyophilized to a tan solid (1.15 g). The solid is taken up in minimal 50 mM aq. NH$_4$HCO$_3$, passed through a 0.45 μm syringe filter, and chromatographed over a CG-71 resin column (2.2 cm×26 cm, 100 mL bed volume) using a nine column volume gradient from 30% MeOH in 50 mM aq. NH$_4$HCO$_3$ to 100% MeOH. Appropriate 15 mL fracions are pooled, concentrated in a rotary evaporator, and lyophilized to afford pure modified lipid II 15 as a white solid (270 mg, 61%). $^1$H NMR (400 MHz, CD$_3$CN: D$_2$O=2:1) δ 5.37 (dd, 1H, J=7.1, 3.2 Hz), 4.48 (d, 1H, J=8.3 Hz), 4.25 (q, 1H, J=6.7 Hz), 4.15 (m, 1H), 3.46 (m, 1H), 2.89 (t, 1H, J=7.6 Hz), 2.22 (t, 1H, J=8.1 Hz), 1.95 (m, 5H), 0.82 (t, 5H, J=6.4 Hz), 0.82 (t, 15H, J=6.4 Hz); ES/MS m/z=1221.9 [M+H]$^+$, 1219.9 [M−H]$^−$.

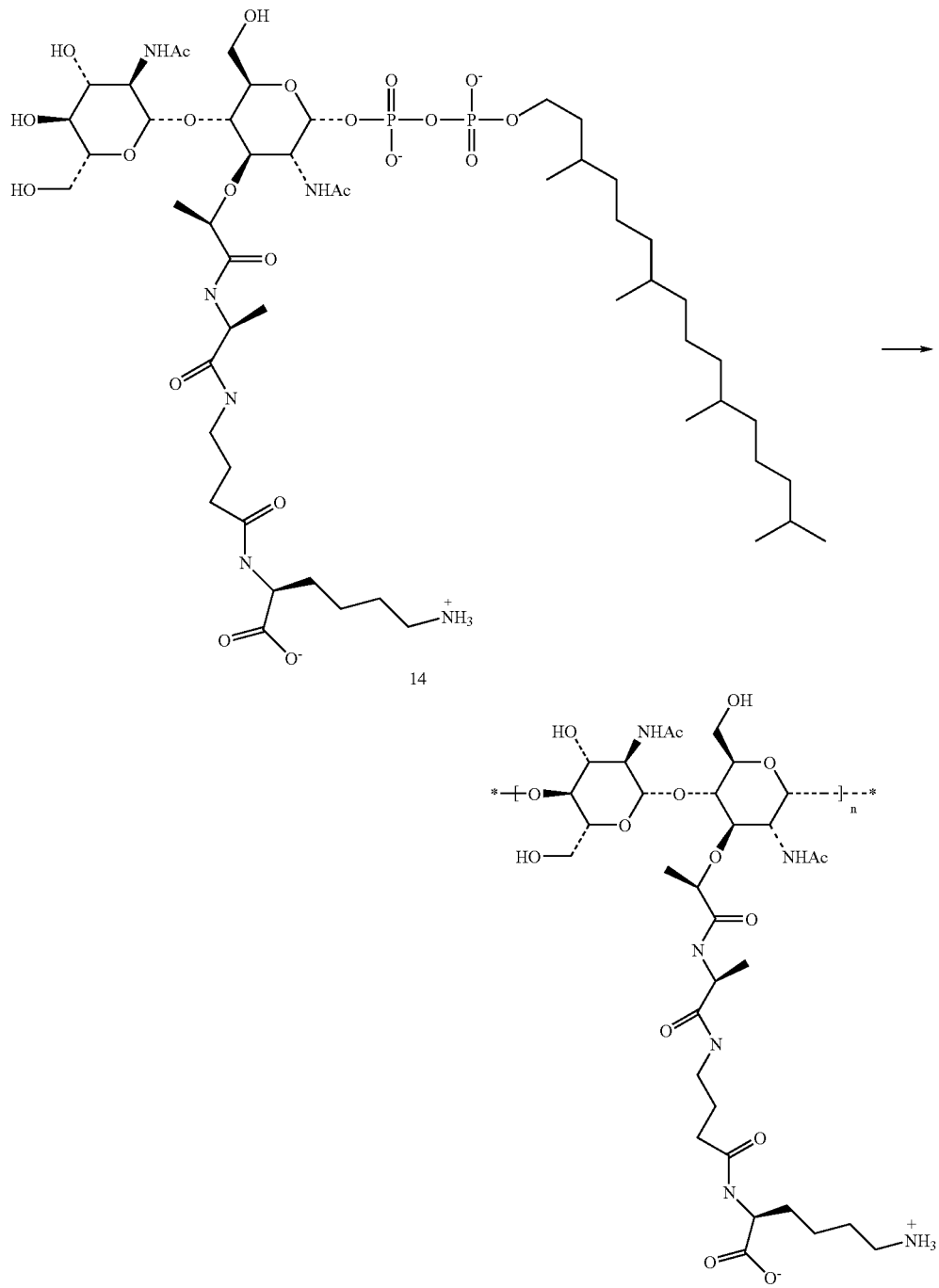

A 20 mM stock solution of 15 is prepared by dissolving the white powder (370 mg) in water (14.5 mL). To water (79.7 mL) is added PEG 8000 (28.8 mL as a 50% stock in water). To this solution is added 0.5M sodium phosphate buffer at pH 7.0 (5.8 mL), 1M aqueous magnesium chloride (3.6 mL). The resulting solution is divided equally among three conical tubes, and to each is added compound 15 stock solution (4.8 mL) with thorough mixing. The polymerization reaction is initiated by addition of 123 μM *Staphylococcus aureus* MtgA enzyme stock solution (3.9 mL). The reaction solutions are mixed well and allowed to stand undisturbed for 24 hr.

As the polymer forms, it aggregates and settles to the bottom of the tube. The supernatant is removed and centrifuged (3500 rpm, 20 min) to recover any polymer that has been adventitiously removed with the supernatant. The pellet is dissolved in 0.2M aqueous HCl (5 mL) and taken on to the next step in this form.

To each of the crude polymer suspensions that remains after decanting the supernatant is added 5M aqueous HCl (2×100 µL with mixing after each addition). The system becomes homogeneous after addition of the acid. To the yellowish solutions thus obtained are added the acidified pellet solutions from processing of the original supernatants (vide supra). These aqueous acidic solutions are incubated at 37° C. overnight, after which the tube contents are pooled to a final volume of about 30 mL. The solution is neutralized to pH 7-8 using about 1.2 mL of 5 M aqueous NaOH, at which point the homogeneous solution becomes cloudy. The cloudy solution is centrifuged twice (3500 rpm, 20 min), the pellet being washed with water each time and then discarded (final volume of retained supernatant=36 mL).

Aqueous 5M NaOH (3.6 mL) is added to bring the final concentration to 0.5M. This solution is allowed to stand at room temperature for 2 hr and is then neutralized to pH 6 with 5M aqueous HCl. The solution is divided into eight aliquots (8×5 mL, 1×3 mL), each in a 50 mL conical tube. Nine volumes of ethanol are added to each tube and the solutions are stored overnight in the −20° C. freezer. The tubes are centrifuged (3500 rpm, 20 min) and the supernatants carefully removed. After brief drying in vacuo, the pellets are dissolved in minimal aqueous NaCl (100 mM) and pooled to a final volume of 16 mL. Nine volumes of ethanol are again added and the precipitation process repeated. Finally, a third round of precipitation is executed.

The final pellet is dissolved in water (40 mL), placed in an Amicon Model 8050 stirred cell concentrator, and subjected to concentration/dilution cycles until the effluent conductance is near zero. The solution is then concentrated as much as possible, filtered through a pre-washed Millipore Steriflip filter, and lyophilized. The synthetic peptidoglycan 15 is thus isolated as a white solid (144 mg, 66%).

Verification of Synthetic Peptidoglycan Structure

The structural identity of the synthetic peptidoglycan 15 is determined by size exclusion chromatography, $^1$H NMR spectroscopy, enzymatic susceptibility and mass spectrometry. Size exclusion chromatography (3.2 mm×30 mm Pharmacia Superose 6 column, 20 mM sodium phosphate buffer at pH=7) indicates the midpoint of the size distribution to be about 150 kilodaltons based on dextran as standard (range about 75 kD to about 375 kD). $^1$H NMR (400 MHz, D$_2$O) δ 4.45 (br s, 1H), 4.32 (br s, 1H), 3.50 (br m, 13H), 2.90 (m, 2H), 2.26 (M, 2H), 1.95 (s, 3H), 1.89 (s, 3H), 1.75 (m, 3H), 1.62 (m, 3H), 1.31 (m, 6H).

Synthetic peptidoglycan 15 is rapidly degraded by lysozyme. Bacterial cell wall glycan polymer, a substructure of peptidoglycan, is the natural substrate for lysozyme. Therefore, lysozyme susceptibility represents *prima facie* evidence for the glycan substructure of 15. Finally, the lysozyme hydrolysis product of 15, N-acetylgulcos-aminyl-β-[1,4]-N-acetylmuramyl-[Ala-GABA-Lys]-peptide, is confirmed by ES/MS m/z 781.6 [M+H]$^+$, 779.5 [M−H]$^−$.

Example 2

Stimulation of IL10 Expression in Human Peripheral Blood Mononuclear Cells By Synthetic Bacterial Antigen Since natural peptidoglycans and bacterial capsular antigens have been shown to stimulate inflammatory cytokines in vitro and in vivo, we sought to determine the cytokine profile elicited from human peripheral blood mononuclear cells (PBMCs) exposed to either CP1 or synthetic PG.

Preparation of Synthetic PG (Compound 15)

For this and all succeeding examples, Compound 15 is prepared as described in Example 1.

Purification of CP1 From Pneumococcal Polysaccharide Powder (ATCC)

For this and all succeeding examples, CP1 is prepared as follows.

One gram of pneumococcal polysaccharide powder (American Type Culture Collection, Manassas, Va.; lot # 2059900, 5 bottles) is dissolved in pyrogen-free distilled water (ca. 25 mL) with intermittent shaking over the course of 8 h. The mixture is transferred to the refrigerator (4° C.) and allowed to stand overnight to complete the dissolution and then transferred to a Teflon bottle. The total volume after quantitative transfer is ca. 50 mL. Aqueous NaOH (4N, 50 mL) is added and the mixture is heated for 1 hr at 80° C. with occasional swirling. After cooling to room temperature, the solution is carefully neutralized with glacial acetic acid (11.3 mL).

The solution is dialyzed (3×, 6-8 kD molecular weight cutoff) against MilliQ water. After dialysis, the solution is filtered (sterile, pyrogen-free, 0.2µ nylon) and the filtrate is adjusted to 50 mM Tris-HCl, pH 8.0. The crude basic hydrolysis product is purified by IEC (ion exchange chromatography; stationary phase=Q-Sepharose Fast Flow, gradient elution mobile phase=50 mM Tris-HCl, pH 8.0 to 50 mM Tris-HCl, pH 8.0 and 11.0M in NaCl). The CP1 containing fractions (180 mL in total) are identified by analytical SEC (size exclusion chromatography; 3.2 mm×30 mm Pharmacia Superose 6 column, 20 mM sodium phosphate buffer at pH 8). The solution is concentrated to 100 mL.

Aqueous NaCl (0.5 M, 200 mL) is added (3× dilution) and the solution is concentrated to 100 mL using an Amicon concentrator (YM series membrane, 10 kD mw cutoff). The NaCl dilution/concentration process is repeated. The resulting solution is diluted with distilled water (200 mL) and concentrated (Amicon) to 100 mL. This process is repeated five times. The final concentration takes the solution to a volume of 30 mL at which point the conductance of the effluent is <40 µS/cm (1 mM NaCl=10 µS/cm) and the pH=6. After filtration (sterile, pyrogen-free, 0.2µ nylon) and rinsing, the final solution volume is 55 mL. The concentration is ca. 10 mg/mL as determined by SEC. The pure CP1 can be stored indefinitely in this aqueous solution form at 4° C.

The identity of the CP1 is verified from an aliquot by $^1$H nmr (Stroop et al. (2002) *Carbohydr. Res.* 337 335-344) and determined to be free from traces of protein and endotoxin by standard assay methodologies.

Human PBMCs are obtained from anonymous donors through the Eli Lilly and Company donor program. Mononuclear cells are separated by Ficoll-hypaque (Stem Cell Technologies, Vancouver, Canada) sedimentation to eliminate red blood cells and polymorphonuclear leukocytes. The mononuclear layer, consisting of T, B, and mononuclear cells, is cultured in RPMI 1640 with 10% fetal bovine serum (Gibco, BRL, Carlsbad Calif.). PBMCs ($2\times10^6$ cells/well) are cultured with several concentrations of Compound 15 or CP1 to determine the optimal response. Although the response to Compound 15 or CP1 typically varies among human donors, a concentration of 0.6 μg/ml of Compound 15 and 6.0 μg/ml of CP1 gives reproducible and consistent results and is therefore used in these experiments (FIG. 3). Following isolation, human PBMCs are treated with Compound 15 (0.6 μg/ml) or CP1 (6.0 μg/ml) and maintained in culture for eight days. Supernatants are sampled daily and analyzed for cytokine expression using a multiplex Enzyme Linked Immunosorbent Assay (Luminex, Linco Research, St. Charles, Mo.; catalog no. HCYTO-60K). The human multiplex cytokine kits employed in these experiments measure IL1, IL2, IL4, IL6, IL8, IL10, TNFα, and INFγ. In additional experiments, a custom IL12 specific antibody bead complex is added to further define the cytokine response (Luminex, Linco Research, St. Charles, Mo.). In all assays, results are normalized against untreated media controls. Data are expressed as the average of triplicate wells±the standard error of the concentration of cytokines represented. The data represent typical results from at least three experiments.

Figure 3:
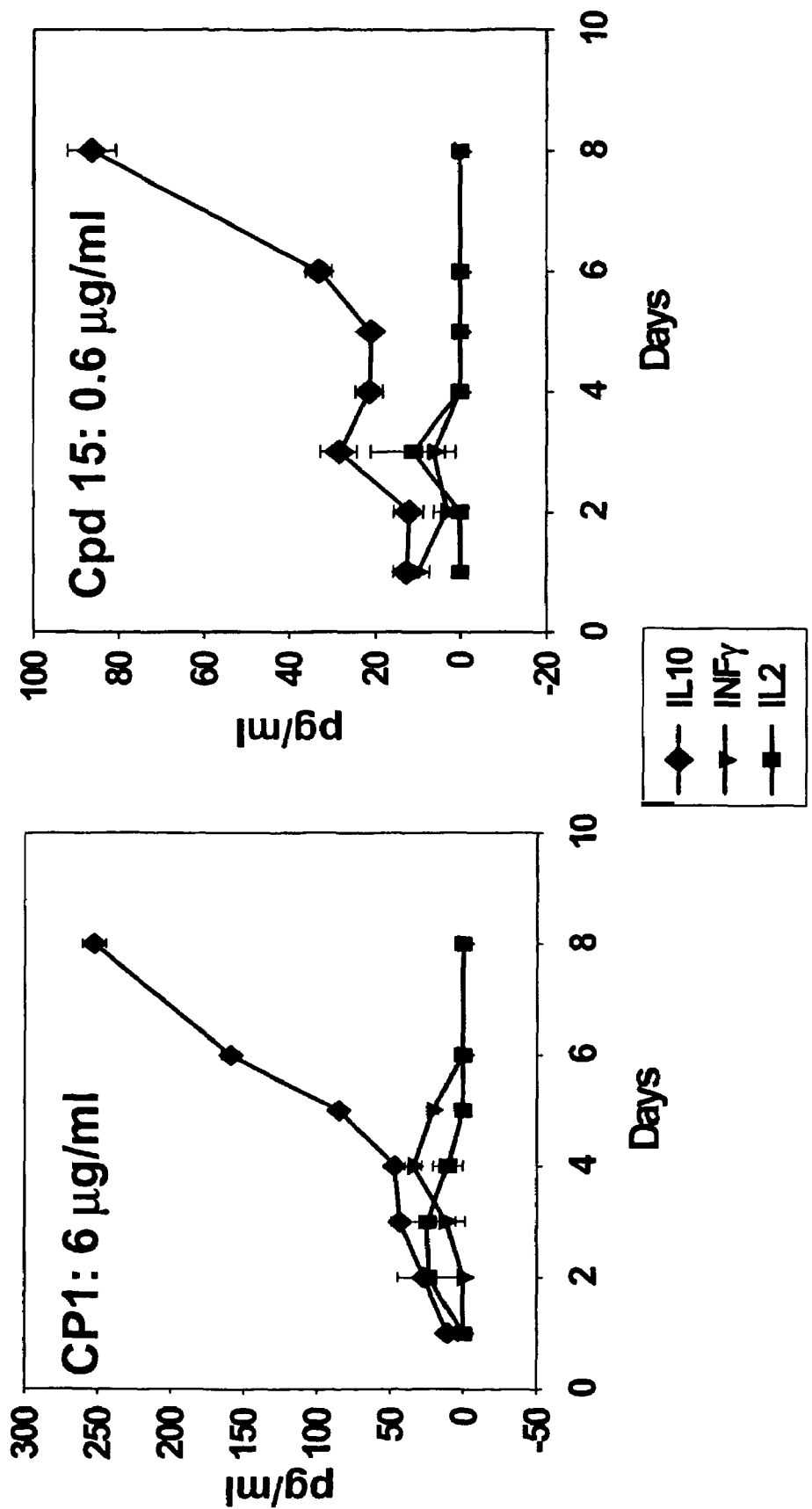
FIG. 3 shows the cytokine profile from human peripheral blood mononuclear cells (PBMCs) treated with CP1 or Compound 15 (PG). Human PBMCs in culture are treated with CP1 at 6.0 micrograms/ml (panel A) or PG at 0.6 micrograms/ ml (panel B), and the expression of cytokines is measured over the course of eight days. Results are normalized against untreated media controls. Data are expressed as the average of triplicate wells 3± the standard error of the concentration of cytokines represented. The results show that the primary response to treatment with these molecules is the expression of IL10.

As shown in FIG. 3, in several experiments, the data reveal that treatment of human PBMCs with Compound 15 or CP1 results in only minimal expression of most inflammatory cytokines represented in the kit. Surprisingly, the predominant response is the expression of the anti-inflammatory cytokine IL10. The expression of IL10 occurs late in the time course, detectable at day 5 and continuing to rise at day 8 to concentrations of approximately 80 pg/ml (Compound 15) to 250 pg/ml (CP1). IL2 and INFγ are only barely detectable early in the time course, whereas the expression of IL4, IL6, IL12 or TNF are not detected at any time point.

These results suggest that CP1 and synthetic PG selectively induce the expression of IL10 in PBMC cell cultures, and that they may be efficacious in animal models of inflammation.

Example 3

Interaction of CP1 and Synthetic PG with Toll-Like Receptor 2 (TLR2)

Toll-like receptors (TLRs) play a critical role in early innate immunity to invading pathogens by sensing the presence microorganisms within the body (Akira et al. (2001) *Nature Immunol.* 2:675-680.) These receptors recognize highly conserved structural motifs only expressed by microbial pathogens, called pathogen-associated microbial patterns (PAMPs) (Medzhitov (2001) *Nat. Rev. Immunol.* 135-145). PAMPs include various bacterial cell wall components such as lipopolysaccharides (LPS), peptidoglycan and lipopeptides, as well as flagellin, bacterial DNA, and viral double-stranded RNA. Stimulation of TLRs by PAMPs initiates a signaling cascade leading to the activation of the transcription factor NF-КB, which induces the secretion of pro-inflammatory cytokines and effector cytokines that direct the adaptive immune response (Janeway et al. (2002) *Annu. Rev. Immunol.* 20:197-216). Since natural peptidoglycan is a PAMP that activates cells via TLR-2 (Iwaki et al. (2002) *J. Biol. Chem.* 277:24315-24320), we sought to determine if synthetic peptidoglycan (Compound 15) could also activate NF-κB in vitro. In addition, since CP1 behaves in vivo like Compound 15, we investigated its ability to activate human TLR2 using an NF-κB-reporter assay in HEK293 cells.

These experiments involve transfecting HEK293 cells (American Type Culture Collection, Manassas, Va.) with two plasmid DNAs. The first plasmid, called pcDNA3.1/hygrow, contains the human TLR-2 gene. The second plasmid, pNF-κB-luc (Stratagene, La Jolla, Calif.), encodes the NF-κB gene linked to a luciferase reporter gene whose product can be followed in vitro as a direct measure of NF-κB-activation. To prepare the DNA for transfection into the cells, Fugene6 (Roche, Basel Switzerland) transfecting reagent is diluted 1:6 in OPTI-MEM (Invitrogen, Carlsbad, Calif.) growth medium. Next, 75 ng of pNF-κB-luc and 300 ng of pcDNA3.1/hygrow DNA are added to the diluted Fugene6 and the mixture is incubated at 37° C. for 30 minutes. HEK293 cells at a concentration of $10^6$ cells/ml are added to the DNA/Fugene6 mixture. After gentle mixing, the cell/DNA mixtures are aliquoted into 96 well tissue culture plates at a concentration of $10^5$ cells/well and incubated for 24 h at 37° C. in a 5% $CO_2$ environment. After incubation, varying concentrations of test compounds are added to the cells and incubation is allowed to continue for an additional 24 h. The amount of luciferase activity resulting from incubation with the compounds is evaluated by removing the growth media from the cells and replacing it with 100 μl of RLB lysis solution (Promega, Madison, Wis.). Lysis is completed by a single freeze/thaw cycle at −80° C. The luciferase activity of each cell culture is determined in a 25 μl aliquot of cell lysate in a Victor Luminometer (Perkin Elmer Life Sciences, Shelton, Conn.) according to the manufacturer's instructions. A positive control for NF-κB activation in HEK293 cells is incubation of transfected cells with TNFα (Pharmingen, Palo Alto, Calif.) at a concentration of 1 ng/ml.

Table 1 shows that, using varying concentrations of commercially-available natural peptidoglycan isolated from *Staphylococcus aureus* (Fluka, St. Louis, Mo.), up to 54.5-fold induction of NFκB activity is observed compared with that of unstimulated cultures. Another commercially available preparation of peptidoglycan and polysaccharide mixture (PG/PS; Lee Labs Inc., Grayson, Ga.) stimulates up to a 33.7-fold induction of NF-κB in HEK293 cells. The data in Table 1 show the lack of NF-κB activation by either Compound 15 or CP1 at concentrations up to 500 μg/ml.

TABLE 1

Luciferase Assay for Measurement of TLR2 Activity in HEK293 Cells

| | Compound[1]: | | | |
|---|---|---|---|---|
| Concentration (μg/ml) | *Staphylococcus aureus* peptidoglycan (Fluka) | PG/PS (Lee Labs Inc) | CP1 | Cpd 15 (PG) |
| 500 | 48.0 | 33.7 | 0 | 0 |
| 250 | 51.8 | 27.0 | 0 | 0 |
| 125 | 54.5 | 15.2 | 0 | 0 |
| 62.5 | 50.7 | 8.8 | 0 | 0 |
| 31.2 | 48.6 | 5.3 | 0 | 0 |
| 15 | 37.7 | 3.0 | 0 | 0 |
| 7.5 | 34.9 | 2.6 | 0 | 0 |
| 3.7 | 31.8 | 1.9 | 0 | 0 |
| 1.8 | 24.7 | 1.6 | 0 | 0 |
| 0.93 | 20.7 | 1.5 | 0 | 0 |
| 0.46 | 17.8 | 1.0 | 0 | 0 |

[1]Positive stimulation control: cultures incubated with 1 ng/ml TNFα yielded a 22.5-fold increase in luciferase activity compared with unstimulated cultures.

These results demonstrate that unlike natural peptidoglycan or bacterial capsular material (which are PAMPs), CP1 and synthetic PG do not induce activation of NF-κB through TLR2.

Example 4

Interaction of CP1 and Synthetic PG with Other Toll-Like Receptors (TLRs)

Concurrently with the studies investigating the interaction of CP1 and synthetic PG with TLR2, we also tested the interaction of CP1 and synthetic PG with an expanded list of TLR constructs using the same NF-κB-reporter assays described above in Example 3 (Table 1). The results are shown in Table 2.

TABLE 2

Summary of TLR activation[1] via NFκB using N/S PAs.

| | Compound | | | |
|---|---|---|---|---|
| Receptor | *Escherichia coli* LPS | CP1 | Cpd 15 (PG) | PG/PS (Lee Labs) |
| TLR2 | + | − | − | ++ |
| TLR2/CD14 | ++ | − | − | ++ |
| TLR4/CD14 | +++ | − | − | − |
| TLR5 | + | − | − | − |
| TLR7 | +/− | − | − | − |
| TLR8 | − | − | − | − |

[1] The relative positive activation of NFκB is indicated by the number of "+" signs while a lack of activation is indicated by a "−" sign.

As shown in Table 2, concentrations of either Compound 15 or CP1 between 0.001-100 µg/ml elicit no NF-κB-signaling with any of the other TLR receptors. In all of these experiments, LPS serves as a positive control for TLR4 activation and natural PG serves as a positive control for TLR2 activation.

These experiments confirm the previous observation (Example 3) that neither Compound 15 nor CP1 activates TLR2, even in the presence of a necessary adaptor molecule CD14 (Janeway et al. (2002) *Annu. Rev. Immunol.* 20:197-216), and extends this observation to five other TLRs.

Example 5

CP1 and Synthetic PG do not Stimulate Maturation of Human Dendritic Cells (DCs)

DCs are often referred to as professional antigen presenting cells and sentinels of the immune system (Banchereau et al. (2000) *Annu. Rev. Immunol.* 18:767-811). They reside in almost all peripheral tissues in an immature state (iDC), which allows them to phagocytose (or engulf) antigens so they can be processed and presented to the immune system, specifically to naïve T cells (Shortman et al. (2002) *Nat. Rev. Immunol.* 2:151-161). With their cargo of processed antigens, the dendritic cells migrate via the blood and lymphatic circulation to lymph nodes, spleen, and other lymphoid tissues. During this journey, they mature, losing their ability to take up and process antigen, and begin to display that antigen on their surfaces. By the time they reach their destinations, they have become potent stimulators of T cells and, with their multitentacled (dendritic) shape, proceed to make cell-cell contact with large numbers of T cells (Banchereau et al. (2000) *Annu. Rev. Immunol* 18:767-811).

Certain CD (cluster of differentiation) markers, which are surface-exposed proteins and glycoproteins, can be used to track the maturation state of the dendritic cells (Chakraborty et al. (2000) *Clin. Immunol.* 94:88-98). Table 3 lists the commonly used CD markers for this purpose and their relative expression levels on monocytes, immature dendritic cells (iDC), and mature dendritic cells (mDC) (Chakraborty et al. (2000) *Clin. Immunol.* 94:88-98).

TABLE 3

Cluster of Differentiation (CD) Markers used to distinguish monocytes (MO), immature-(iDC) and mature- (mDC) dendritic cells.

| | Cell Surface Marker[1]: | | | | |
|---|---|---|---|---|---|
| | CD1a | CD14 | CD83 | CD86 | HLA-DR |
| MO | − | ++ | − | − | − |
| iDC | ++ | − | − | − | − |
| mDC | ++ | − | +++ | +++ | +++ |

[1] The relative amount of each cell surface marker is indicated in the table by the number of "+" signs while the absence of the cell surface marker is indicated by a "−" sign Labeling cells with fluorescently-conjugated anti-CD antibodies permits analysis of dendritic cell maturation status via determination of mean fluorescence intensity (MFI) of the marker on the surface of a cell population. Flow cytometry is used to analyze large cell samples for the presence of cell surface markers. In vitro, iDC can be produced by isolating CD14(+) monocytes from human blood and culturing these cells for four days with a cocktail of two cytokines (Granulocyte-Macrophage Colony-Stimulating Factor (GM-CSF) and Interleukin-4 (IL-4)). Since several bacterial molecules, for example LPS (Matsunaga et al. (2002) *Scand. J. Immunol.* 56:593-601) and peptidoglycan (Michelsen et al. (2001) *J. Biol. Chem.* 276:25680-25686), can induce the differentiation of iDCs to the mDC phenotype (as would occur during activation of the innate immune system), we were interested in evaluating the potency of CP1 and synthetic PG in maturing human monocyte-derived dendritic cells.

Human PBMCs are obtained from anonymous donors through the Eli Lilly and Company donor program. Mononuclear cells are separated by Ficoll-hypaque (Stem Cell Technologies, Vancouver, Canada) sedimentation to eliminate red blood cells and polymorphonuclear leukocytes. The CD14(+) monocyte fraction is isolated from PBMCs by incubation with CD14-conjugated magnetic beads (Miltenyi Biotech Inc., Auburn, Calif.) followed by physical separation in a magnetic field using an autoMACS apparatus (Miltenyi Biotech, Inc., Auburn, Calif.). Once isolated, the CD14(+) monocytes are incubated in complete DC media consisting of RPMI 1640 containing 10% heat-inactivated Australian fetal bovine serum (FBS), non essential amino acids, sodium pyruvate, 2-mercaptoethanol, penicillin-streptomycin (as 1× solutions all from Gibco BRL, Carlsbad Calif.). In addition, some cultures are induced to differentiate into iDCs using complete DC medium containing 20 ng/ml IL-4 (Sigma, St. Louis, Mo.) and 40 ng/ml GM-CSF (Pharmingen, Palo Alto, Calif.) for four days at 37° C. with 5% $CO_2$. After the four day incubation, cells are incubated with CP1, synthetic PG, or LPS for an additional 24 h before being stained for CD marker analysis by flow cytometry. The standard staining protocol for flow cytometry involves washing the cells twice in Dulbecco's phosphate buffered saline (DPBS, Gibco BRL, Carlsbad, Calif.) containing 2% heat inactivated FBS (Gibco BLR, Carlsbad, Calif.) and 0.05% sodium azide (Sigma, St. Louis, Mo.), hereafter referred to as "flow wash solution." After washing, $10^5$ cells/sample are resuspended in 100 µl of flow wash solution and 20 µl of pre-diluted phycoerythrin-conjugated primary anti-CD marker antibody (all antibodies used are from Pharmingen, Palo Alto, Calif.) for 15 min on ice. A similarly conjugated isotype control antibody is included in all analyses. After incubation, cells are washed three times in flow wash solution. After the final wash, cells are fixed by resuspension in the flow wash solution containing 1% paraformaldehyde (Becton Dickinson, Palo Alto, Calif.). Cell samples are stored at 4° C. and protected from light until analysis using an FC500 flow cytometer (Beckman Coulter, Miami, Fla.). Once cells are correctly gated for forward and side scatter profiles, mean fluorescent intensity (the amount of marker on the cell surface) is evaluated for 10,000 cells/sample.

The results of these experiments are summarized in Table 4.

TABLE 4

Flow cytometric analysis of monocyte-derived dendritic cells after incubation with N/S PAs or LPS.

| Cell type | Cell Surface Marker[1]: | | | | |
|---|---|---|---|---|---|
| | CD1a | CD14 | CD83 | CD86 | HLA-DR |
| MO | 5.1 | 16.5 | 5.6 | 12.8 | 23.9 |
| iDC | 116.1 | 3.3 | 7.6 | 10.9 | 7.7 |
| iDC + CP1 | 122.7 | 3.3 | 7.6 | 11.4 | 8.7 |
| iDC + Cpd 15 | 109.8 | 3.4 | 9.5 | 12.1 | 9.1 |
| iDC + LPS | 124.4 | 4.1 | 46.7 | 75.4 | 29.2 |

[1]Numbers represent mean fluorescence intensity of cell surface markers in 10,000 cells/sample.

As shown in Table 4, the panel of surface markers used in this experiment confirms that the four day incubation of CD14(+) monocytes with GM-CSF and IL-4 induces the differentiation of the cells into immature dendritic cells (compare the results in Table 4 with the expected phenotype summarized in Table 3. As shown in Table 4, these immature dendritic cells are functionally capable of reaching a mature state since incubation of these cells with *E. coli* LPS (the positive control for maturation) significantly increases the staining of CD-83, -86 and HLA-DR on their cell surfaces, which is the expected phenotype of a mature DC. The data in Table 4 show that incubation with either CP1 or Compound 15 fails to change the staining profile from the iDC state, indicating that neither compound is capable of effecting the maturation of dendritic cells.

Example 6

Uptake of Synthetic PG by Immature Human Dendritic Cells (iDCs)

The inhibition of maturation of DCs induced by CP1 and synthetic PG may be due to the inability of these cells to process these molecules internally. Antigen uptake and processing (degradation) are two fundamental properties of APCs (Banchereau et al. (2000) Annu. Rev. Immunol. 18:767-811). DCs are the most potent APCs of the immune system in part because of their powerful capacity to endocytose or sample material from their environment (Shortman et al. (2002) *Nat. Rev. Immunol.* 2:151-161). To determine whether iDCs are capable of endocytosing high molecular weight immunomodulatory polysaccharide antigens such as synthetic PG, we prepared a fluorescent derivative of Compound 15 for use in uptake studies employing confocal microscopy. This imaging technique can be used to localize within cells fluorescent probes such as the Oregon-green labeled Compound 15 disclosed herein. In these experiments, we use as a control molecule fluorescently labeled (FITC) dextran polymer. Dextran (40 kDa in size) is a macromolecule commonly used for endocytosis experiments (Sallusto et al. (1995) *J. Exp. Med.* 182:389-400). Since it is a high molecular weight carbohydrate polymer, it is a useful comparator for Compound 15.

Oregon-green labeled Compound 15 is prepared as described in PCT International Publication WO 01/79242. Briefly, Oregon-green (Molecular Probes, Eugene, Oreg.)-conjugated Lipid II is included in an MtgA-polymerization reaction at a ratio of 1:4 with unlabeled Lipid 11 to produce a 25% Oregon-green labeled polymer. The polymeric material is purified and treated as previously described. For uptake studies, fluorescent Compound 15 at a final concentration of 50 μg/ml, or Lysine-fixable FITC-conjugated dextran (40 kDa size, Molecular Probes, Eugene, Oreg.) at 1 mg/ml, is incubated with human monocyte-derived iDC prepared as described in Example 5 for two minutes at 37° C. After incubation, extracellular probe is removed by washing the cells four times in ice cold complete DC medium (Example 5). Washed cells are then incubated at 37° C. and staining is stopped at two-minute intervals by washing in 1% paraformaldehyde fix diluted in flow wash solution (which also contains the metabolic poison sodium azide; protocol described in Example 5). Glass slide samples are prepared at each time interval and sealed with clear nail polish. Samples are stored at −20° C. and protected from light until analysis on a Radiance 2100 confocal microscope (BioRad Laboratories, Hercules, Calif.).

FIG. 4 shows black and white confocal images of human iDCs treated with either FITC-Dextran (40 kDa in size) or Oregon-green labeled Compound 15 (approx. 150 kDa in size) for two minutes. After incubation with the polymers, the cells are washed extensively to remove any external polymer and the internalized material is followed at two-minute intervals.

Intracellular localization of either Compound 15 or Dextran is visible as bright areas in the dark field of the cells after a two-minute incubation with the polymers (FIG. 4). Furthermore, the internalized polymers are not spread throughout the cytoplasm, but are instead localized in discrete packets or vesicles, consistent with their presence in endocytic vacuoles.

These results demonstrate that iDCs are capable of endocytosing synthetic PG.

Example 7

Kinetics of Uptake of Synthetic PG by Immature Human Dendritic Cells (iDCs)

Since there appears to be such robust uptake of Compound 15 by iDCs (FIG. 4), the fluorescent version of this molecule was used in flow cytometry to visualize the kinetics of polymer uptake.

In these experiments, human monocyte-derived dendritic cells are prepared as described in Example 5. Dendritic cells are resuspended at $5 \times 10^5$ cells/sample and incubated on ice at 37° C. At the start of each time course, cells are incubated with either fluorescent Compound 15 at a final concentration of 50 μg/ml or Lysine-fixable FITC-conjugated dextran (40 kDa size, Molecular Probes, Eugene, Oreg.) at 1 mg/ml. At 0, 2, 10, 20, 30, 40, and 50 minutes after the start of incubation, uptake is stopped by washing the cells with four washes of ice cold flow wash buffer (Example 5). The washed cells are fixed in paraformaldehyde also as described in Example 5. Stained, fixed cells are stored at 4° C. protected from light until analysis using a FC500 flow cytometer (Beckman Coulter, Miami, Fla.). Once cells are correctly gated for forward and side scatter profiles, mean fluorescent intensity of the population is evaluated for 10,000 cells/sample. FIG. 5 shows that over time, Compound 15 accumulates in the iDC cytoplasm. The same is true for the control molecule FITC-Dextran. To control for non-specific adhesion of the molecules to the cell surface (which could be read as a positive in this assay), cells are also incubated with fluorescent polymers at 0° C. At this temperature, the iDCs are viable yet unable to endocytose material, i.e., they are metabolically inactive (Sallusto et al. (1995) *J. Exp. Med.* 182:389-400). At this temperature, signal from neither the control molecule (FITC-dextran) nor Compound 15 increases over time (FIG. 5). This indicates that the uptake seen at 37° C. is a result of cellular endocytosis.

These results demonstrate that iDCs are capable of rapidly endocytosing fluorescently labeled Compound 15, and that the inability of this molecule to mature DCs is not due to recalcitrance to endocytic uptake thereof.

Example 8

CP1 and Synthetic PG Interfere with LPS-Induced Maturation of iDCs

As shown above in Table 4 (Example 5), LPS at 50 µg/ml is capable of transforming iDCs to an mDC phenotype characterized by an increase in co-stimulatory markers (CD83 and CD86) as well as class 11 Major Histocompatibility (MHC) markers (HLA-DR) (Chakraborty et al. (2000) *Clin. Immunol.* 94:88-98). We next investigated whether CP1 and synthetic PG are capable of interfering with the transformation of iDCs to mDCs. The results are shown in Table 5.

TABLE 5

Flow cytometric analysis of monocyte-derived dendritic cells matured with *E. coli* LPS in the presence of N/S PAs

| Cell type | Cell Surface Marker[1]: | | | | |
|---|---|---|---|---|---|
| | CD1a | CD14 | CD83 | CD86 | HLA-DR |
| iDC + LPS | 126.4 | 4.1 | 46.7 | 75.4 | 29.2 |
| iDC + LPS + CP1 | 132.2 | 4.3 | 51.1 | 49.0 | 31.8 |
| iDC + LPS + Cpd 15 | 120.2 | 4.1 | 52.6 | 59.2 | 31.9 |

[1]Numbers represent mean fluorescence intensity of 10,000 cells/sample.

In these experiments, CD14(+) monocytes are isolated from human PBMCs and differentiated into iDCs as described in Example 5. After differentiation, iDCs are incubated with either of two known inducers of cell maturation: *E. coli* LPS (Matsunaga et al. (2002) *Scand. J. Immunol.* 56:593-601) or a cytokine cocktail containing Tumor Necrosis Factor-α (TNF-α), Interleukin-1β (IL-1β), Prostaglandin $E_2$, and IL-6 (Dieckman et al. (2002) *J. Exp. Med.* 196:247-253) for 24 h. To some induced cultures we also add 50 µg/ml CP 1 or 100 µg/ml Compound 15 at the same time we add either LPS or cytokines. After incubation, the cells are evaluated for CD1a, CD14, CD83, CD86, and HLA-DR expression by flow cytometry as described in Example 5.

In the case of cytokine-matured iDCs, flow cytometry confirms that maturation by incubation with the cytokine cocktail occurs; however, incubation with CP1 or synthetic PG has no influence on the matured phenotype as determined by surface marker analysis (data not shown). In contrast to this, Table 5 shows that both CP1 and synthetic PG are able to interfere with LPS-induced maturation of iDCs. Specifically, surface expression of the co-stimulatory marker CD86 is decreased in the presence of these molecules, while the other markers tested are essentially unchanged. Additional experiments also demonstrate that CD80, another marker of co-stimulation, is also decreased (data not shown).

The powerful capacity of DCs to activate T cells is linked to their constitutive expression of both MHC and costimulatory markers like the family B7 markers (i.e., CD80 and CD86) (Banchereau et al. (2000) *Annu. Rev. Immunol.* 18:767-811). If these molecules are decreased or absent from the DC cell surface, the DCs are unable to participate in stimulatory cognate interactions with T cells. Schwartz (1990) *Science* 248: 1349-1356 was the first to observe that presentation of antigen on MHC molecules in the absence of costimulatory molecules induces T-cell anergy. Thus, DCs can provide both stimulatory (by virtue of being APCs) and downregulatory signals for immune reactions.

To understand fully the significance of the above findings, it is important to understand the role of DCs in immune tolerance. Tolerance is an essential property of the immune system whereby self- or auto-antigens do not trigger an immune response (Belz et al. (2002) *Immunol. Cell Biol.* 80:463-468). Others have shown that when DCs undergo an incomplete maturation (low levels of CD80 and or CD86), or have been treated with antibodies that block the B7 family of costimulatory markers (i.e., CD80 and CD86), these cells can induce antigen-specific unresponsiveness in vitro and T cell anergy in vivo (Lu et al. (1996) *J. Immunol.* 157:3577-3586; Gao et al. (1999) *Immunology* 98:159-170). Immature DCs are now understood to contribute to peripheral tolerance by inducing the differentiation of human T regulatory cells (Jonuleit et al. (2000) *J. Exp. Med.* 192:1213-1222), a group of T cells that display regulatory functions in vitro and in vivo. Activated T regulatory cells have also been shown to elicit the production of IL-10, an anti-inflammatory cytokine, through autocrine expression or induction in effector T cells (Dieckmann et al. (2002) *J. Exp. Med.* 196:247-253). Thus, the fact that Compound 15 and CP1 appear to influence the expression of costimulatory markers on the DC surface suggests a mechanism of action for these molecules in the induction of toleragenic DCs. These anergic DCs could then induce T-cell anergy directly or through the activity of a T regulatory cell population.

Example 9

CP1 and Synthetic PG Are Not Polyclonal Mitopens and Do Not Stimulate Proliferation of Lymphocytes in Human PBMC Cultures Mitogens are substances that nonspecifically induce DNA synthesis and cell division in lymphocytes. LPS is a B-cell specific mitogen (Moller et al. (1973) *J. Infect. Dis.* 128:52-56), while phytohaemagglutinin (PHA) specifically induces T cells to divide (Boldt et al. (1975) *J. Immunol.* 114:1532-1536). Peptidoglycan is another T cell mitogen (Levinson et al. (1983) *Infect. Immun.* 39:290-296). We were therefore interested in determining whether CP1 or Compound 15 could stimulate human peripheral blood mononuclear lymphocytes (PBMCs) to divide in culture, particularly since Compound 15 is a completely synthetic peptidoglycan. Cell division is measured in these experiments by uptake of radiolabeled nucleotide base into the DNA of the proliferating cells. The radioactive counts per minute (cpm) of the culture, measured by scintillation counting, are a direct measure of cellular proliferation.

In this experiment, PBMCs are isolated from a healthy human volunteer as described in Example 2. Isolated PBMCs are aliquoted into round-bottomed 96-well tissue culture plates (Falcon Brand, Becton Dickinson, Palo Alto, Calif.) at density of $10^5$ cells/well. Some cells are also incubated with 50 µg/ml of CP1, 100 µg/ml Compound 15, or 25 µg/ml PHA (Sigma, St. Louis, Mo.) as a positive control for T cell proliferation. Cells are incubated at 37° C. in a 5% $CO_2$ atmosphere for up to four days. At 30, 54, and 78 hours post inoculation, some cultures are pulsed with 1 µCi/well of [$^3$H]-thymidine (Specific Activity 6.7 Ci/mmol; ICN Inc, Costa Mesa, Calif.) and returned to 37° C. incubation for a further 18 hours before being harvested onto filter plates (Packard Instruments, Shelton, Conn.) using a Filtermate harvester (Packard Instruments, Shelton, Conn.). Filterplates are dried after harvesting, prior to the addition of 20 µl/well of Microscint-O scintillation cocktail (Packard Instruments, Shelton, Conn.). Scintillation counting is performed with a MicroBeta TriLux liquid scintillation counter (Perkin Elmer, Shelton, Conn.).

FIG. 6 shows the typical proliferation response of human PBMCs to the polyclonal T cell activator PHA. The incorporation of [$^3$H]-thymidine into PHA-treated cells is close to 100,000 times that of untreated cells after two days exposure, and proliferation rates increase up to four days. In contrast, neither CP1— nor Compound 15—treated cells respond by DNA proliferation and expansion (FIG. 6). Therefore, these molecules do not appear to behave like polyclonal mitogens in human PBMC cultures.

Example 10

CP1 Stimulates an Increase in CD4+CD25+ T Cells

As CP1 and Compound 15 do not behave like mitogens (Example 9), we hypothesized that the lack of proliferation is due T regulatory cell suppression. This experiment examines the possibility that these compounds stimulate an increase in T regulatory cell numbers as defined by the surface markers CD4 and CD25.

In these experiments, human PBMCs are isolated and cultured at a density of $10^5$ cells/well in 96-well tissue culture plates as described in Example 2. Some cultures also receive 0.6 or 6.0 µg/ml of CP1 immediately after being aliquoted into the tissue culture plates. Cell cultures are incubated at 37° C. in a 5% $CO_2$ atmosphere for up to six days. Each day during culture, cell samples are removed and stained for the co-expression of CD4 and CD25 on the cell surface by flow cytometry. Samples are stained using the standard staining protocol outlined in Example 5. Antibodies for human CD4, CD25, as well as an isotype control antibody, are obtained from Pharmingen (Palo Alto, Calif.).

FIG. 7 shows the percentage of CD4+/CD25+ cells in CP1-treated PBMC cultures sampled each day over the course of six days. The percentage of CD4+/CD25+ cells in untreated PBMCs is highest after two days of culture, and accounts for up to 2% of total cells in the culture. Incubation of human PBMCs with 0.6 or 6.0 µg/ml CP1 increases the percentage of CD4+/CD25+ cells to 4.5% and 9.0%, respectively, in these cultures (FIG. 7).

These data suggest that treatment of human PBMCs with a polysaccharide immunomodulator such as CP1 induces an increase in the number of cells possessing a T regulatory phenotype.

Example 11

CP1 and Synthetic PG Suppress the αCD3 Antibody-Induced Proliferation of Lymphocytes in Human PBMCs When an antigen (Ag) is presented to a naïve T cell in the context of MHCII on the surface of an antigen presenting cell (APC), there is engagement of the MHC-Ag complex with the T cell receptor (TCR)/CD3 complex on the surface of the T cell (Weiss et al. (1986) *Annu. Rev. Immunol.* 4:593-619). This interaction, together with an amplification signal generated by CD28-B7 (CD80, CD86) interaction on these two cell types leads to T cell activation, cytokine stimulation, and cell division (Weiss et al. (1986) *Annu. Rev. Immunol.* 4:593-619. In the absence of Ag or APC, T lymphocytes can become activated and proliferate in vitro by incubation with plate-bound anti-CD antibodies (van Lier et al. (1989) *Immunol.* 68:45-50). Mimicking the activation by antigens, the binding of CD3 antibodies to T cells results in the activation of tyrosine kinase, a rise in the intracellular calcium concentration, generation of diacylglycerol, and activation of protein kinase C. Both calcium and protein kinase C serve as intracellular messengers for the induction of gene activation (van Lier et al. (1989) *Immunol.* 68:45-50). As shown in FIG. 6 of Example 9, anti-CD3 antibody-mediated T cell proliferation is also measured by the incorporation of [$^3$H]-thymidine into the DNA of dividing cells.

Since proliferation of PBMCs is not observed following treatment with either CP1 or Compound 15 (FIG. 6), we hypothesized that these molecules may stimulate T regulatory cells as suggested by the results shown in FIG. 7. The present experiment is performed to investigate whether these molecules induce suppression of lymphocyte proliferation.

In these experiments, human PBMCs are isolated and cultured as described in Example 2 and plated at $10^6$ cell/ml in T-25 tissue culture flasks (Corning Inc., Corning, N.Y.) for 24 h at 37° C. in a 5% $CO_2$ atmosphere. Cultures are exposed to either CP1 at 50 µg/ml or PG at 100 µg/ml during this period. One day prior to the incubation of cells on antibody coated plates, anti-human CD3 antibody (Clone UCHT1, Pharmingen, Palo Alto, Calif.) or an isotype-matched control antibody (Pharmingen, Palo Alto, Calif.) is diluted in Dulbecco's phosphate buffered saline (DPBS) (Gibco, BRL, Carlsbad, Calif.), and the wells of a 96-well tissue culture plate are coated with 100 µl aliquots of diluted antibody. Plates are coated overnight at 4° C. and washed three times in DPBS before use. Human PBMCs, exposed to CP1, Compound 15, or not exposed to either compound, are plated into antibody-coated wells at a density of $10^5$ cells/well. Tissue culture plates are incubated at 37° C. in a 5% $CO_2$ atmosphere for 30 or 54 hours before 1 µCi/well of [$^3$H]-thymidine (Specific Activity 6.7 Ci/mmol; ICN Inc, Costa Mesa, Calif.) is added to each well. Cells are then returned to 37° C. incubation for an additional 18 h before the cells are harvested as described in Example 9. The liquid scintillation counting procedure is also as described Example 9. The data for this experiment are presented both as raw counts per minute (cpm) of radioactivity and as a stimulation index (SI), which is the ratio of the cpm of cells in αCD3 antibody-coated wells to the cpm of cells in isotype (control) antibody-coated wells.

FIG. 8 shows that either 48 or 72 hours exposure to αCD3 antibody causes human PBMCs to proliferate as shown by the uptake of [$^3$H]-thymidine (FIG. 8, triangles). Furthermore, the amount of proliferation is directly correlated to the amount of αCD3 antibody in the well, with the highest proliferation seen in cells exposed to 0.4 μg/ml αCD3 antibody. FIG. 8 also shows that pre-incubation of human PBMCs with either 50 μg/ml of CP1 or 100 μg/ml PG for 24 h prior to incubation with αCD3 antibody causes a decrease in the amount subsequent proliferation (FIG. 8, diamonds for CP1 and squares for PG Compound 15).

These results demonstrate that N/S PAs inhibit anti-CD3-induced lymphocyte proliferation.

Example 12

Micro-Array Analysis of Human CD3+ Cells Following Treatment with N/S PAs and αCD3 Antibody The results demonstrating cytokine expression shown in FIG. 3 are corroborated and extended by measurement of cytokine modulation using microarray technology.

PBMCs are isolated as described in Example 2 and added to 6-well tissue culture plates in a medium containing RPMI with 10% fetal bovine serum (Gibco BRL, Carlsbad, Calif.), 50 μM β-mercaptoethanol, and 500 μg/ml penicillin/streptomycin (complete medium). T cell density is 2.5×10$^6$ cells per well. Either 50 μg/ml CP-1,100 μg/ml Compound 15, or complete medium is added to each well of the appropriate plate. Incubation is at 37° C. for 24 hours. Simultaneously, 6-well tissue culture plates are treated with either 0.2 μg/ml αCD3 in sterile Phosphate-Buffered Saline (PBS, Gibco BRL, Carlsbad, Calif.), 5 ml/well, or an equal volume of sterile PBS. The uninoculated plates are incubated overnight at 4° C. Following incubation, cells treated with CP1 or synthetic PG, or untreated control cells, are gently resuspended and added to plates that have either been coated with αCD3 or not, and incubation is continued at 37° C. for an additional 48 hours.

PBMCs are then processed with a Pan T Cell Isolation Kit (Miltenyi Biotec, cat. #130-053-001; Auburn, Calif.) in substantial accordance with the manufacturer's instructions. This kit is a magnetic labeling system designed to isolate untouched T cells from peripheral blood. Non-T cells are removed by magnetic separation from unlabeled CD3+ cells using an autoMACS (Miltenyi Biotec Inc, Auburn, Calif.). The isolated T cells are stored at −80° C.

Total RNA is isolated from the cells using Trizol (Gibco-BRL, Carlsbad, Calif.) followed by chloroform extraction and subsequent alcoholic precipitation following procedures specified by the manufacturer. The RNA is quantitated spectrophotometrically, and its integrity assessed by gel analysis. All RNA preparations are stored at −80° C. until needed.

Total RNA serves as the template for the synthesis of biotin-labeled cDNA. This labeled cDNA is subsequently used as a probe for commercially available directed microarrays. Specifically, a GEArray Q Series Human Common Cytokine Kit, cat. # HS-003N (SuperArray Bioscience Corporation, Frederick, Md.) is employed. Probe synthesis and microarray processing are performed as suggested by the manufacturer. A Typhoon 8600 Imager (Amersham Pharmacia Biotech, Piscataway, N.J.) is used in chemiluminescent mode to capture and store images that are then analyzed using ImageQuant software (Amersham Pharmacia Biotech, Piscataway, N.J.). Data are exported to Microsoft Excel, and image intensity is corrected for background and normalized between experiments using GEArray Analyzer software (SuperArray Bioscience Corporation, Frederick, Md.).

Analysis of the data reveals a cytokine modulation pattern that is consistent with that seen using the multiplex Enzyme Linked Immunosorbent Assay as shown in FIG. 3. Table 6 shows that cells exposed to CP1 consistently demonstrate an up-regulation of IL10 and IL19, which is a homolog of IL10, and a down-regulation of IL17. IL17 is thought to be expressed mainly by activated T cells, and functions to initiate and maintain an inflammatory response. Cells that are exposed to αCD3 are activated and therefore show an up-regulation of IL17, TNF-β, and other cytokines known to participate in the inflammatory process. Anti-CD3-treated cells also show decreases in both IL10 and IL19. When either CP1 or Compound 15 is added to cells that are subsequently exposed to αCD3, there is a dramatic increase in IL10 levels, accompanied by concomitant decreases in IL17 and TGF-β.

TABLE 6

Cytokine Response in T Cells Exposed to Various Stimuli

| Stimulus | Up-Regulation* | Down-Regulation* |
| --- | --- | --- |
| CP-1 (50 μg/ml) | IL19 | IL17 |
| α-CD3 (0.2 μg/ml) | IL17 | IL10 |
|  | TNF-β | IL19 |
| α-CD3 (0.2 μg/ml) + | IL10** | IL17 |
| CP-1 (50 μg/ml) | IL19 | TNF-β |

*Change from untreated cells of at least 5-fold
**Also seen with Compound 15 @ 100 μg/ml The up-regulation of IL10 expression in CD3+ T cells induced by both CP1 and Compound 15 in these microarray experiments corroborates the results observed in Example 2, and in animal models, and suggests that this cytokine can be used as a biological marker to monitor the biological/immunological activity of both CP1 and synthetic PG in vitro and in vivo. The data also suggest that directed microarrays can be used to monitor not only the biological activity of the present compounds, but also the biological activity of derivative compounds to determine the effects of structural differences on immunodulatory potency.

Example 13

N/S PAs Protect Against the Formation of Intra-Abdominal Abscesses

Since CP1 and synthetic PG induce T regulatory cells with suppressive function in vitro as well as the late production of IL10 from human PBMCs (Examples 10 and 11, and Example 2, respectively), we were interested in assessing the ability of these polymer antigens to protect animals against the inflammatory formation of abscesses in vivo. A rat intraabdominal abscess model is used to address this question.

The rat model of abscess formation employed in these studies is a modification of that described by Onderdonk et al. ((1977) *J. Infect. Dis.* 136:82-87) and Tzianabos et al. ((1993) *Science* 262:416-419). Male Lewis rats (Charles River Laboratories, Wilmington, Mass.), weighing between 135-175 grams, are used for all experiments. Rats are housed in microisolator cages and given chow (Ralston Purina, St. Louis, Mo.) and water ad libitum. Upon arrival, animals are allowed to acclimate for 24 hours. Intra-abdominal abscesses are induced by a single intraperitoneal injection of prepared inoculum containing *Bacteroides fragilis* (ATCC 23745; American Type Culture Collection, Manassas, Va.) (10$^8$ colony forming units per animal) mixed at a 1:6 dilution with an adjuvant solution containing sterile rat cecal contents. *B. fragilis* is maintained at −80° C. in brain heart infusion broth. Cultures are grown anaerobically in brain heart infusion broth to log phase and diluted for use with rat sterile cecal contents (rSCC). rSCC is prepared from rat cecal pellets that are solubilized in brain heart infusion broth, autoclaved, and then filtered. Animals are euthanized at six days post-inoculation and assessed for abscess formation. Animals with one or more fully formed abscesses are scored as positive. Animals with no abscesses yield a negative score. Individuals scoring the results are blinded to the identity of the experimental groups.

Animals (10 rats/group) are dosed subcutaneously with three doses of Compound 15 or CP1 at twenty four hour intervals the day before, the day of, and the day after challenge with *B. fragilis*/rSCC (Tzianabos et al. *J. Clin. Invest.* 96:2727 (1995)). Challenge with the inoculum is carried out by the intraperitoneal route. Animals are administered log dilutions of Compound 15 or CP1 at 100, 10, and 1 μg (×3)/animal. Results are expressed as the percent protection (number of animals with no abscesses/treatment group), and statistical significance is calculated using the Fishers Exact Probability Test.

As shown in Table 7, both CP1 and Compound 15 produce considerable protection against the formation of abscesses at both the 100 μg and 10 μg doses when compared to that of saline controls. Protection is assessed as the complete absence of abscesses as compared to control animals with one or more abscess. Protected animals show no deleterious effects of antigen administration, with few, if any, signs of fever or lethargy, which are common symptoms of inflammation. Nor do these animals display symptoms of sepsis.

TABLE 7

Activity of N/S PAs in the Rat Abscess Model

| Treatment Group | Animals with Abscesses/group | % of Animals with Abscesses | % Protection |
| --- | --- | --- | --- |
| CP1 100 μg × 3 SC | 1/8 | 12.5 | 87.5 |
| CP1 10 μg × 3 SC | 2/8 | 25 | 75 |
| CP1 1.0 μg × 3 SC | 3/8 | 37.5 | 62.5 |
| Saline 0.1 ml × 3 SC | 6/8 | 75 | 25 |
| Cpd 15 100 μg × 3 SC | 1/8 | 12.5 | 87.5 |
| Cpd 15 10 μg × 3 SC | 1/8 | 12.5 | 87.5 |
| Cpd 15 1.0 μg × 3 SC | 2/8 | 25 | 75 |
| Saline 0.1 ml × 3 SC | 6/8 | 75 | 25 |

Taken together with the data shown in Examples 2-12, these data suggest that protection against the inflammatory processes required for the formation of abscesses in response to bacterial challenge in this model is inhibited by the presence of immature dendritic cells, which can directly inhibit T cell activation or induce the generation of a T regulatory population. Direct inhibition of inflammatory cells by T regulatory cell contact can further stimulate the expression of IL-10. In total, one or more of these events may orchestrate the inhibition of inflammation seen in the in vivo abscess model.

Example 14

N/S PAs Reduce the Incidence and Severity of Post-Surgical Adhesions

Exogenous IL10 has been shown to limit the formation of post-surgical adhesions (Holschneider et al. (1997) *J. Surg. Research* 70:138-143). Further, T regulatory cells have potent anti-inflammatory activity and have been shown to limit inflammation in in vivo models (Maloy et al. (2001) *Nat. Immunol.* 2:816-822; Shevach (2002) *Nat. Rev. Immunol.* 2389-400). T regulatory cells have also been shown to elicit the production of IL10 from their target inflammatory T cells (Diekman et al. (2002) *J. Exp. Med.* 196:247-253). As variously shown in Examples 2, 10, 11, 12, and 13, above, CP1 and Compound 15 stimulate the production of IL10 from PBMCs, an increase in T regulatory cell numbers and function in vitro, and afford protection from the formation of abscesses in vivo. Since the inflammatory responses that lead to fibrin deposition and the formation of abscesses is similar to the pathologies involved in adhesion formation, we hypothesized that treatment with CP1 or Compound 15 in an adhesion model would likewise stimulate the activity of T regulatory cells and ultimately the endogenous production of IL10 that may result in reduction in the formation of post-surgical adhesions.

To test this hypothesis, male Lewis rats (Charles River Laboratories, Wilmington, Mass.) are dosed subcutaneously with three injections of Compound 15 or CP1 at twenty four hour intervals the day before, the day of, and the day after surgical induction of adhesions (Tzianabos et al. (1995) *J. Clin. Invest.* 96:2727-2731). Rats are administered log dilutions of each compound at 100 μg, 10 μg, and 1 μg (×3) in 0.2 ml saline/animal. Control groups are administered saline in 0.2 ml volumes at the same dosing schedule. Peritoneal adhesions are induced following the methods of Kennedy et al. ((1996) *Surgery* 120:866-871) and Tzianabos et al. (PCT International Publication WO 00/59515) with minor modifications. Briefly, rats are anesthetized with 2-5% isoflurane in oxygen to a surgical plane of anesthesia. A one to two cm midline incision is made into the abdominal cavity to expose the cecum. The cecum is aseptically removed from the peritoneal cavity and abraded with surgical gauze to induce visible microhemorrhages. The cecum is then re-inserted into the peritoneal cavity. The left and right lateral abdominal walls are inverted aseptically and also abraded in the manner described above. Following this procedure, 0.2-0.3 ml of rat sterile cecal contents (rSCC), prepared as described in Example 13, are added to the peritoneal cavity as an inflammatory adjuvant (Onderdonk et al. (1982) *J. Clin. Invest.* 69:9-14). The peritoneum is closed with 3-0 silk followed by skin closure with tissue adhesive (3M Animal Care Products, St. Paul, Minn.). Animals are sacrificed one week following surgical manipulation and evaluated for the formation of adhesions. Adhesions are scored on a scale of 0-5 using the method described by Kennedy et al ((1996) *Surgery* 120:866-871): 0=no adhesions; 1=thin filmy adhesion; 2=more than one thin adhesion; 3=thick adhesion with focal point; 4=thick adhesion with planar attachment; and 5=very thick vascularized adhesions or more than one planar adhesion. This scoring system approximates the system used in human medicine, enumerates adhesions present, and indicates the severity of the adhesion pathology; higher scores indicate greater severity in inflammation and adhesion formation. The results are shown in Table 8.

TABLE 8

Activity of N/S PAs in the Rat Adhesion Model

| Treatment Group | Range of Adhesion Scores/Individual Scores | Mean Adhesion Score | Median |
|---|---|---|---|
| CP1 100 µg × 3 SC | 0-4 (0, 1, 2, 24) | 1.8 | 2.0 |
| CP1 10 µg × 3 SC | 1-4 (1, 1, 3, 3, 4) | 2.4 | 3.0 |
| CP1 1.0 µg × 3 SC | 1-4 (1, 1, 3, 3, 4) | 2.6 | 3.0 |
| Saline 0.1 ml × 3 SC | 3-4 (3, 3, 4, 5, 5) | 4 | 4 |
| Cpd 15 100 µg × 3 SC | 0-4 (0, 0, 2, 2, 4) | 1.6 | 2 |
| Cpd 15 10 µg × 3 SC | 0-4 (0, 1, 3, 3, 4) | 2.2 | 3.0 |
| Cpd 15 1.0 µg × 3 SC | 0-4 (0, 1, 3, 3, 4) | 2.2 | 3 |
| Cpd 15 0.1 µg × 3 SC | 1-4 (1, 3, 3, 4, 4) | 3 | 3 |
| Saline 0.1 ml × 3 SC | 3-4 (3, 3, 4, 4, 4) | 3.6 | 4 |

The data shown in Table 8 demonstrate that adhesion formation in rats treated with 100 µg of Compound 15 or CP1 is significantly limited (median score=2.0) when compared to that in saline controls (median score=4.0). These data demonstrate that these polysaccharide antigens effectively protect rats from the formation of severe surgically induced adhesions, and suggest that these polymers induce an anti-inflammatory effect in vivo.

Example 15

N/S PAs Inhibit Delayed Type Hypersensitivity Reactions in a Guinea Pig Model

Clinical evaluation of the safety and efficacy of immune modulators such as CP1 and Compound 15 requires a convenient biomarker. This is necessary because safety and dose determination are usually determined in healthy volunteers, where a defined inflammatory process is not measured. Furthermore, such a biomarker would be useful in later stage trials as abscesses and/or adhesions cannot be readily observed and graded for therapeutic efficacy in a non-invasive manner following therapy with immune modulators. Consequently, we developed a delayed type hypersensitivity (DTH) animal model (Gray et al. (1994) Curr. Opin. Immunol. 6:425-437). This assay can also be used in humans as a biomarker for clinical efficacy studies using the present immune modulators. Clinically, DTH skin tests are of significant value in the overall assessment of immunocompetence in humans (Gray et al. (1994) Curr. Opin. Immunol. 6:425-437; Kuby et al. (2000) Immunology, W. H. Freeman and Co). Such tests including the administration of candin as described below are commonly used to test immuno-competence in AIDS patients.

A Guinea pig model is used to demonstrate the utility of a DTH response as a biomarker. A localized DTH response in an animal model represents an important source of information with regard to T cell function. Direct measurements of the DTH response can be readily observed and measured in humans and animals. Flares, wheals, and/or indurations can be observed and readily measured quantitatively on the surface of the skin.

For this purpose, female Hartley Guinea pigs (Charles River Laboratories, Wilmington, Mass.) weighing 250-299 grams are used for all DTH experiments. Guinea pigs are housed in microisolator cages and given chow (Ralston Purina, St. Louis, Mo.) and water ad libitum. Upon arrival, the animals are allowed to acclimate for 24 hours. Hair is then clipped from the back of the animal in an area approximately 2×2 inches. The area is scrubbed with povidone-iodine (H&P Industries/Triad Medical Inc., Mukwonago, Wis.) followed by an alcohol scrub. Next, the animal is sensitized to *Candida albicans* antigens by injecting a 0.2 ml saline suspension of *Candida albicans* A26 (ATCC 90234) intradermally on the dorsal side of the neck region. Cultures of *Candida albicans* A26 are maintained at −80° C. in a glycerol and lactose freezing solution, and are grown aerobically on Sabourauds and dextrose agar slants (DIFCO, Detroit, Mich.) at 35° C. for 24 hours. Cultures are then suspended in sterile saline and adjusted spectrophotometrically to a predetermined optical density equivalent to approximately $2.0 \times 10^7$ cells/ml before use.

Three days following sensitization, the animals are treated with the immunomodulator CP1 formulated in sterile water for injection (Abbott Laboratories, North Chicago, Ill.) at 100, 10 and 1.0 ng per 0.2 ml. The animals are injected subcutaneously on the dorsal side of the neck with 0.2 ml. A third group of animals dosed with the water vehicle serves as the positive control group.

Four days following sensitization, the animals are shaved and scrubbed as described above. Four equally spaced areas in the shaved region are injected intradermally with 0.1 ml of Candin (Allermed Laboratories, Inc., San Diego, Calif.), which serves as a recall antigen for T cells that have been previously sensitized to *C. albicans*. The animals are observed daily over three days for erythema, wheals, and indurations at these four sites. Two traverse (vertical and horizontal) diameters of the flares are recorded for each site. These are averaged and a mean of the flare area ($mm^2$) is calculated. Treated animals are compared to untreated controls in order to assess therapeutic efficacy. The results are shown in Table 9.

TABLE 9

The Activity of CP1 in a Model of Delayed Type Hypersensitivity (DTH) Area of Flare ($mm^2$)

| $H_2O$ Control | CP1 1.0 ng × 1 (SC) | CP1 10 ng × 1 (SC) | CP1 100 ng × 1 (SC) |
|---|---|---|---|
| 76.26 ± 5.52 | 63.34 ± 9.64 | 50.92 ± 4.26 | 43.99 ± 5.56 |

The data shown in Table 9 demonstrate a significant reduction in the flare area in animals treated with CP1 as compared to that of control animals.

These findings demonstrate that a DTH skin assay is an appropriate biomarker for clinical use and evaluation of polysaccharide immunomodulators such as CP1 and synthetic PG Compound 15.

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

We claim:

1. A synthetic polymeric antigen having the structure shown in Formula I:

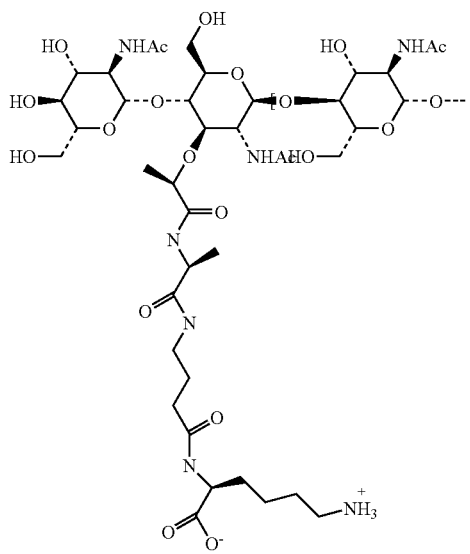
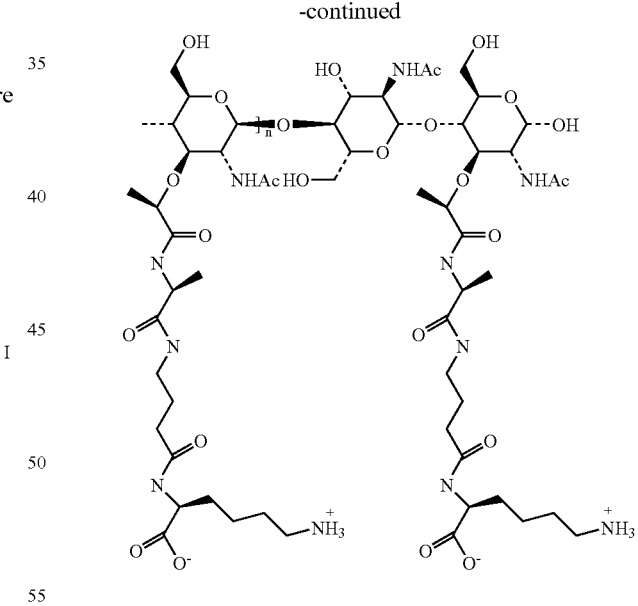

where n is an integral in the range of from about 375 to about 75, or a pharmaceutically acceptable salt thereof.

2. A composition, comprising said synthetic polymeric antigen or pharmaceutically acceptable salt thereof of claim 1, and a buffer, carrier, diluent, or excipient.

3. A pharmaceutical composition, comprising said synthetic polymeric antigen or pharmaceutically acceptable salt thereof of claim 1, and a pharmaceutically acceptable buffer, carrier, diluent, or excipient.

4. A solution comprising said synthetic polymeric antigen or pharmaceutically acceptable salt thereof of claim 1, and a solvent.

5. A method of inhibiting the maturation of an antigen presenting that is a dendritic cell, comprising contacting in vitro said antigen presenting cell and an effective amount of the synthetic polymeric antigen or pharmaceutically acceptable salt thereof of claim 1, for a time and under conditions effective to inhibit maturation of said antigen presenting cell.

6. The method of claim 5, wherein inhibition of maturation of said antigen presenting cell is accompanied by a reduction in the level of expression of one or more surface markers selected from the group consisting of CD80 and CD86 by said antigen presenting cell.

7. The method of claim 5, wherein inhibition of maturation of said antigen presenting cell is accompanied by a reduction in the level of expression of one or more cytokines selected from the group consisting of IL6, IL12, interferon alpha, and interferon gamma by said antigen presenting cell.

8. A method of increasing the expression of interleukin 10 (IL10) in a mammal in need thereof, comprising:

(a) isolating peripheral blood mononuclear cells, or a monocyte-containing fraction thereof, from said mammal;

(b) contacting in vitro said isolated peripheral blood mononuclear cells or monocytes and a composition containing an effective amount of cytokines that differentiate monocytes to immature dendritic cells for a time and under conditions effective to generate immature monocyte-derived dendritic cells;

(c) contacting in vitro said immature monocyte-derived dendritic cells and an effective amount of the synthetic polymeric antigen or pharmaceutically acceptable salt thereof of claim 1, for a time and under conditions effective to prevent maturation of said immature monocyte-derived dendritic cells; and (d) administering said immature monocyte-derived dendritic cells to said mammal, thereby increasing the expression of IL10 in said mammal.

9. The method of claim 8, wherein said cytokine composition of step (b) comprises granulocyte-macrophage colony-stimulating factor and IL4.

* * * * *